United States Patent
Du et al.

(10) Patent No.: US 11,591,301 B2
(45) Date of Patent: Feb. 28, 2023

(54) INDOLEAMINE-2,3-DIOXYGENASE INHIBITOR, PREPARATION METHOD THEREFOR AND USE THEREOF

(71) Applicant: HINOVA PHARMACEUTICALS INC., Sichuan (CN)

(72) Inventors: Wu Du, Sichuan (CN); Wen Ren, Sichuan (CN); Haibin Lv, Sichuan (CN); Haibo Li, Sichuan (CN); Kun Wen, Sichuan (CN); Jinyun He, Sichuan (CN); Dekun Qin, Sichuan (CN); Xinghai Li, Sichuan (CN); Yuanwei Chen, Sichuan (CN)

(73) Assignee: HINOVA PHARMACEUTICALS INC., Sichuan (CN)

( * ) Notice: Subject to any disclaimer, the term of this patent is extended or adjusted under 35 U.S.C. 154(b) by 177 days.

(21) Appl. No.: 16/967,077

(22) PCT Filed: Jan. 31, 2019

(86) PCT No.: PCT/CN2019/074274
§ 371 (c)(1),
(2) Date: Nov. 3, 2020

(87) PCT Pub. No.: WO2019/149255
PCT Pub. Date: Aug. 8, 2019

(65) Prior Publication Data
US 2021/0047281 A1    Feb. 18, 2021

(30) Foreign Application Priority Data

Feb. 2, 2018 (CN) .......................... 201810107237.8

(51) Int. Cl.
*C07D 271/08* (2006.01)
*C07D 413/12* (2006.01)

(52) U.S. Cl.
CPC ......... *C07D 271/08* (2013.01); *C07D 413/12* (2013.01)

(58) Field of Classification Search
CPC .................. C07D 271/08; C07D 413/12
See application file for complete search history.

(56) References Cited

FOREIGN PATENT DOCUMENTS

| CN | 102164902 A | 8/2011 |
|---|---|---|
| CN | 105646389 A | 6/2016 |
| CN | 107033097 A | 8/2017 |
| CN | 107176933 A | 9/2017 |
| CN | 108863986 A | 11/2018 |
| WO | 2007075598 A2 | 7/2007 |
| WO | 2010005958 A | 6/2010 |
| WO | 2013174947 A1 | 11/2013 |
| WO | 2014066824 A1 | 5/2014 |
| WO | 2016155545 A1 | 10/2016 |

OTHER PUBLICATIONS

Zhao, Guisen et al.; Basis of New Drug Design and Development; Shandong University Press, Nov. 30, 2015, pp. 139-140.

*Primary Examiner* — Kamal A Saeed
(74) *Attorney, Agent, or Firm* — Novick, Kim & Lee, PLLC; Allen Xue

(57) ABSTRACT

A compound is represented by formula (I). A pharmaceutical composition contains the compound of formula (I). The compound is used in the preparation of an indoleamine-2,3-dioxygenase (IDO) inhibitor drug. The compound exhibits inhibition effect on IDO protease and metabolizes stably in the body. The compound or pharmaceutical composition thereof can be used for preparing an IDO inhibitor drug, and can also be used for preparing a drug for preventing and/or treating diseases having IDO-mediated tryptophan metabolic pathway pathological features.

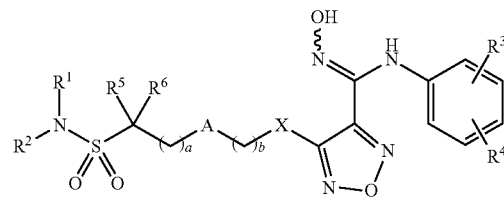

(I)

14 Claims, No Drawings

INDOLEAMINE-2,3-DIOXYGENASE INHIBITOR, PREPARATION METHOD THEREFOR AND USE THEREOF

TECHNICAL FIELD

The present invention belongs to the field of pharmaceutical chemistry, and relates to an indoleamine-2,3-dioxygenase inhibitor, the preparative method and the use thereof.

BACKGROUND ART

Malignant tumor is one of the major diseases threatening human health and life. According to the statistics of the National Health Commission, the incidence of tumor in China's mainland is about 235/100000, and the mortality rate is about 144.3/100000.

Due to the unlimited growth, invasion and metastasis of malignant tumors, three conventional treatment methods (surgery, radiotherapy, and chemotherapy) currently used in clinical can not allow to completely remove or kill tumor cells, so tumor metastasis or recurrence often occurs. Tumor biotherapy is a new therapeutic method that uses modern biotechnology and its related products for prevention and treatment of tumors. Because of its characteristics such as safety, effectiveness, low side effects, and so on, biotherapy has become the fourth mode of tumor treatment except for surgery, radiotherapy, and chemotherapy. It can achieve the anti-tumor effect by inspiring the natural defense mechanism of the host or giving the naturally produced substances with strong targeting.

Indoleamine-2,3-dioxygenase (IDO) is a kind of heme-containing monomer protein, and consisted of 403 amino acid residues, including two folded α-helix domains. The large domain contains catalytic pocket, and the substrate can have hydrophobic and other interactions with IDO in the catalytic pocket. Except for liver, IDO is the only rate-limiting enzyme which can catalyze tryptophan metabolism and make it decompose to a series of metabolites including quinolinic acid by the kynurenine pathway. Another kind of enzymes catalyzing tryptophan metabolism are tryptophan-2,3-dioxygenase, which have similar heme activity sites with IDO, but only about 10% of the amino acid sequences of both enzymes are same. About 95% of free L-tryptophan in human body can be metabolized by the kynurenine pathway, and many kinds of biologically active metabolites are produced, including kynurenine, kynuric acid, 3-hydroxykynurenine, 3-hydroxy-2-aminobenzoic acid, picolinic acid, quinolinic acid, and oxidized coenzyme A, etc. The expression level of IDO was lower in normal state, and increased significantly in the process of inflammation or infection. In addition, lipopolysaccharide and cytokines and so on could induce the expression of IDO. In vitro study indicates that except for kynurenine, the intermediate metabolites of tryptophan, 3-hydroxy-2-aminobenzoic acid and quinolinic acid, can also induce apoptosis of T-lymphocyte in in vitro mouse thymocytes. Tumor cells can induce local immunity by consuming local tryptophan and producing metabolites. Meanwhile, the level of local infiltrative T-lymphocytes in tumor decreases significantly. In short, IDO can inhibit the local immunity of tumor via the following ways: (1) Tryptophan depletion mechanism: it is clear that by making IDO overexpress and resulting in the lack of tryptophan necessary for T cell proliferation, the effective proliferation of T cells is affected and leads to the apoptosis of cells; (2) Toxic mechanism of tryptophan metabolites: the metabolites produced by the degradation of tryptophan catalyzed by IDO can inhibit the function of activated T cells and even induce apoptosis of T cells; (3) IDO can inhibit the immune function of activated T cells by inducing the proliferation of regulatory T cells. Therefore, IDO is a potential target for tumor immunotherapy.

The disclosed patent applications of inhibitors for selective inhibition of IDO include WO2010005958, WO2013174947, WO2014066834, WO2016155545, CN201610059454.5, CN2017100610.4, etc.

1-Methyltryptophan is an oral small molecular IDO inhibitor developed by Newlink Genetics, which is used to treat metastatic breast cancers and solid tumors. It is currently in the phase II clinical trial that has continued for a long time. In addition, for a series of oral IDO small molecular inhibitors being developed by Incyte company, INCB-24360 is also undergoing phase III clinical trials, which is mainly used to treat a variety of cancers including myelodysplastic syndrome. However, there is a certain of toxic and stable problems for drug metabolism in clinical trials.

Therefore, in order to realize better effect and purpose of tumor treatment and better meet the market demand, it is urgently needed to develop a new generation of high-efficient and low toxic selective IDO inhibitors.

CONTENT OF THE INVENTION

In order to solve the above technical problems, the present invention provides an indoleamine-2,3-dioxygenase inhibitor, the preparative method and the use thereof.

The present invention provides compounds of formula (I), or optical isomers thereof, or cis- and trans-isomers thereof, or isotope compounds thereof, or solvates thereof, or pharmaceutically acceptable salts thereof, or pro-drugs thereof, or tautomers thereof, or mesomers thereof, or racemates thereof, or enantiomers thereof, or diastereoisomers thereof, or mixtures thereof, or metabolites thereof, or metabolic precursors thereof:

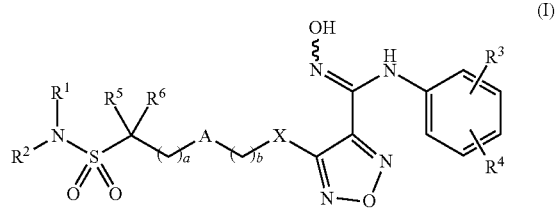

Wherein, a and b are independently of each other selected from an integer of 0~5;

X is selected from O, S, —O—NH—, —NH—, and —NH—O—;

A is selected from none, —$NR_{11}$—, O, S,

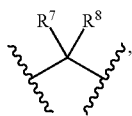

sulfuryl, sulfoxide, $C_3$-$C_7$ cycloalkyl, substituted $C_3$-$C_7$ cycloalkyl, $C_3$-$C_7$oxacycloalkyl, substituted $C_3$-$C_7$oxacycloalkyl, $C_3$-$C_7$azacycloalkyl, substituted $C_3$-$C_7$azacycloalkyl,

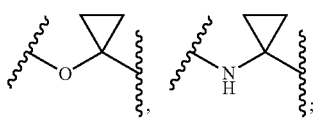

$R_{11}$ is selected from H, $C_1$-$C_6$ alkyl;

$R^1$ and $R^2$ are independently of each other selected from the group consisting of H, hydroxyl, amino, aryl, $C_1$-$C_6$ alkyl, substituted $C_1$-$C_6$ alkyl, $C_3$-$C_7$ cycloalkyl, substituted $C_3$-$C_7$ cycloalkyl, $C_3$-$C_7$ heterocyclyl, substituted $C_3$-$C_7$ heterocyclyl, $C_1$-$C_6$ alkoxyl, substituted $C_1$-$C_6$ alkoxyl, $C_1$-$C_6$ alkylamino, substituted $C_1$-$C_6$ alkylamino;

Or $R^1$ and $R^2$ are linked to form 3-8 membered heterocycle; or $R^1$ and $R^2$ are linked to form substituted 3-8 membered heterocycle;

$R^3$ and $R^4$ are independently of each other selected from the group consisting of H, halogen, cyano, trifluoromethyl, sulfuryl, sulfoxide, $C_1$-$C_6$ alkyl, substituted $C_1$-$C_6$ alkyl, $C_3$-$C_7$ cycloalkyl, substituted $C_3$-$C_7$ cycloalkyl, $C_1$-$C_6$ alkoxyl, substituted $C_1$-$C_6$ alkoxyl;

$R^5$, $R^6$, $R^7$, $R^8$ are independently of each other selected from the group consisting of H, deuterium, halogen, hydroxyl, amino, $C_1$-$C_6$ alkyl, $C_3$-$C_6$ cycloalkyl, $C_1$-$C_6$ alkoxyl, $C_1$-$C_6$ alkylamino;

Or any two of $R^5$, $R^6$, $R^7$, and $R^8$ are linked to form a 3-8 membered carbocyclic ring.

Further, a and b are independently of each other selected from the integers of 0~5;

X is selected from S, —NH—;

A is selected from none, O, —NR$_{11}$—, sulfuryl,

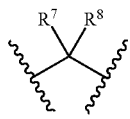

$C_3$ cycloalkyl,

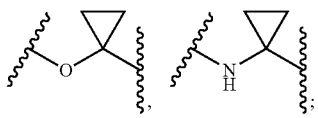

$R_{11}$ is selected from H, methyl;

$R^1$ and $R^2$ are independently of each other selected from the group consisting of H, hydroxyl, $C_1$-$C_3$ alkyl, substituted $C_1$-$C_3$ alkyl, $C_3$-$C_6$ cycloalkyl, methoxyl, substituted $C_1$ alkylamino; or $R^1$ and $R^2$ are linked to form 4-6 membered heterocycle; or $R^1$ and $R^2$ are linked to form substituted 4-6 membered heterocycle;

The substituents in said substituted $C_1$-$C_3$ alkyl are deuterium, hydroxyl, methyl-substituted $C_1$ alkylamino, amino, halogen; the substituent in said substituted $C_1$ alkylamino is methyl; the heteroatoms in said 4-6 membered heterocycle are N, O, and the number of said heteroatom is 1, 2; the heteroatom in said substituted 4-6 membered heterocycle is N, and the number of said heteroatom is 1, 2; The substituents in said substituted 4-6 membered heterocycle are methyl, hydroxyl, halogen;

$R^3$ and $R^4$ are halogen;

$R^5$, $R^6$, $R^7$, $R^8$ are independently of each other selected from the group consisting of H, deuterium, halogen, hydroxyl, amino; or any two of $R^5$, $R^6$, $R^7$, and $R^8$ are linked to form a 3-4 membered carbocyclic ring.

Further, said compound of formula (I) has the structure of formula (II):

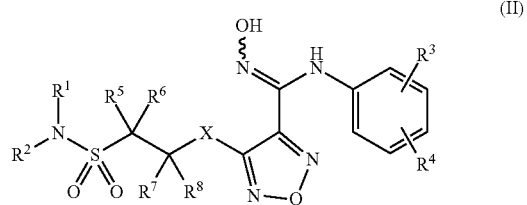

(II)

Wherein, X is selected from S, —NH—;

$R^1$, $R^2$ are independently of each other selected from the group consisting of H, hydroxyl, $C_1$-$C_3$ alkyl, substituted $C_1$-$C_3$ alkyl, $C_3$-$C_6$ cycloalkyl, methoxyl, substituted $C_1$ alkylamino; or $R^1$ and $R^2$ are linked to form 4-6 membered heterocycle; or $R^1$ and $R^2$ are linked to form substituted 4-6 membered heterocycle;

The substituents in said substituted $C_1$-$C_3$ alkyl are deuterium, hydroxyl, methyl-substituted $C_1$ alkylamino, amino, halogen; the substituent in said substituted $C_1$ alkylamino is methyl; the heteroatoms in said 4-6 membered heterocycle are N, O, and the number of said heteroatom is 1, 2; the heteroatom in said substituted 4-6 membered heterocycle is N, and the number of said heteroatom is 1, 2; The substituents in said substituted 4-6 membered heterocycle are methyl, hydroxyl, halogen;

$R^3$ and $R^4$ are halogen;

$R^5$, $R^6$, $R^7$, $R^8$ are independently of each other selected from the group consisting of H, deuterium, halogen, hydroxyl, amino; or any two of $R^5$, $R^6$, $R^7$, and $R^8$ are linked to form a 3-4 membered carbocyclic ring.

Further, said compound of formula (I) has the structure of formula (III):

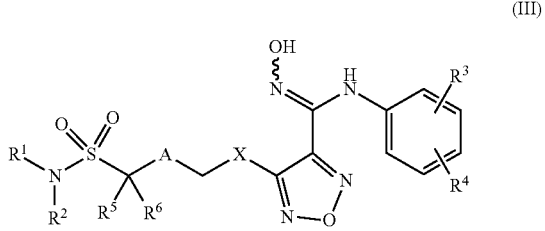

(III)

Wherein, X is selected from S, —NH—;

$R^1$ and $R^2$ are independently of each other selected from the group consisting of H, hydroxyl, $C_1$-$C_3$ alkyl, substituted $C_1$-$C_3$ alkyl, $C_3$-$C_6$ cycloalkyl, methoxyl, substituted $C_1$ alkylamino; or $R^1$ and $R^2$ are linked to form 4-6 membered heterocycle; or $R^1$ and $R^2$ are linked to form substituted 4-6 membered heterocycle;

The substituents in said substituted $C_1$-$C_3$ alkyl are deuterium, hydroxyl, methyl-substituted $C_1$ alkylamino, amino, halogen; the substituent in said substituted $C_1$ alkylamino is methyl; the heteroatoms in said 4-6 membered heterocycle are N, O, and the number of said heteroatom is 1, 2; the heteroatom in said substituted 4-6 membered heterocycle is N, and the number of said heteroatom is 1, 2; The substitu ents in said substituted 4-6 membered heterocycle are methyl, hydroxyl, halogen;

$R^3$ and $R^4$ are halogen;

A is selected from none, O, —$NR_{11}$—, sulfuryl, $$\begin{array}{c} R^7 \; R^8 \\ \diagdown\!\!\diagup \\ \text{\scriptsize{$\sim$}} \quad \text{\scriptsize{$\sim$}} \end{array},$$

$C_3$ cycloalkyl, (cyclopropane with O), (cyclopropane with NH);

$R_{11}$ is selected from H, methyl;

$R^5$, $R^6$, $R^7$, $R^8$ are independently of each other selected from the group consisting of H, deuterium, halogen, hydroxyl, amino; or any two of $R^5$, $R^6$, $R^7$, and $R^8$ are linked to form a 3-4 membered carbocyclic ring.

Further, said compound of formula (I) has the structure of formula (IV):

(IV)

Wherein, X is selected from S, —NH—;

$R^1$, $R^2$ are independently of each other selected from the group consisting of H, hydroxyl, $C_1$-$C_3$ alkyl, substituted $C_1$-$C_3$ alkyl, $C_3$-$C_6$ cycloalkyl, methoxyl, substituted $C_1$ alkylamino; or $R^1$ and $R^2$ are linked to form 4-6 membered heterocycle; or $R^1$ and $R^2$ are linked to form substituted 4-6 membered heterocycle;

The substituents in said substituted $C_1$-$C_3$ alkyl are deuterium, hydroxyl, methyl-substituted $C_1$ alkylamino, amino, halogen; the substituent in said substituted $C_1$ alkylamino is methyl; the heteroatoms in said 4-6 membered heterocycle are N, O, and the number of said heteroatom is 1, 2; the heteroatom in said substituted 4-6 membered heterocycle is N, and the number of said heteroatom is 1, 2; the substituents in said substituted 4-6 membered heterocycle are methyl, hydroxyl, halogen;

$R^3$ and $R^4$ are halogen;

A is selected from none, O, —$NR_{11}$—, sulfuryl, $$\begin{array}{c} R^7 \; R^8 \\ \diagdown\!\!\diagup \\ \text{\scriptsize{$\sim$}} \quad \text{\scriptsize{$\sim$}} \end{array},$$

$C_3$ cycloalkyl, (cyclopropane with O), (cyclopropane with NH);

$R_{11}$ is selected from H, methyl;

$R^5$, $R^6$, $R^7$, $R^8$ are independently of each other selected from the group consisting of H, deuterium, halogen, hydroxyl, amino; or any two of $R^5$, $R^6$, $R^7$, and $R^8$ are linked to form a 3-4 membered carbocyclic ring.

Further, said compound of formula (I) has the structure of formula (V):

(V)

Wherein, X is selected from S, —NH—;

$R^1$, $R^2$ are independently of each other selected from the group consisting of H, hydroxyl, $C_1$-$C_3$ alkyl, substituted $C_1$-$C_3$ alkyl, $C_3$-$C_6$ cycloalkyl, methoxyl, substituted $C_1$ alkylamino; or $R^1$ and $R^2$ are linked to form 4-6 membered heterocycle; or $R^1$ and $R^2$ are linked to form substituted 4-6 membered heterocycle;

The substituents in said substituted $C_1$-$C_3$ alkyl are deuterium, hydroxyl, methyl-substituted $C_1$ alkylamino, amino, halogen; the substituent in said substituted $C_1$ alkylamino is methyl; the heteroatoms in said 4-6 membered heterocycle are N, O, and the number of said heteroatom is 1, 2; the heteroatom in said substituted 4-6 membered heterocycle is N, and the number of said heteroatom is 1, 2; the substituents in said substituted 4-6 membered heterocycle are methyl, hydroxyl, halogen;

$R^3$ and $R^4$ are halogen;

A is selected from none, O, —$NR_{11}$—, sulfuryl, $$\begin{array}{c} R^7 \; R^8 \\ \diagdown\!\!\diagup \\ \text{\scriptsize{$\sim$}} \quad \text{\scriptsize{$\sim$}} \end{array},$$

$C_3$ cycloalkyl, (cyclopropane with O), (cyclopropane with NH);

$R_{11}$ is selected from H, methyl;

$R^5$, $R^6$, $R^7$, $R^8$ are independently of each other selected from the group consisting of H, deuterium, halogen, hydroxyl, amino; or any two of $R^5$, $R^6$, $R^7$, and $R^8$ are linked to form a 3-4 membered carbocyclic ring.

Further, said compound of formula (I) has the structure of formula (VI):

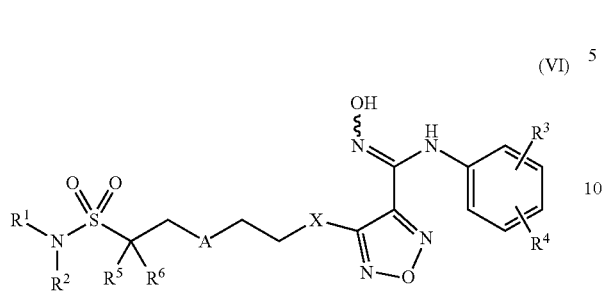

(VI)

Wherein, X is selected from S, —NH—;

R¹ and R² are independently of each other selected from the group consisting of H, hydroxyl, $C_1$-$C_3$ alkyl, substituted $C_1$-$C_3$ alkyl, $C_3$-$C_6$ cycloalkyl, methoxyl, substituted $C_1$ alkylamino; or R¹ and R² are linked to form 4-6 membered heterocycle; or R¹ and R² are linked to form substituted 4-6 membered heterocycle;

The substituents in said substituted $C_1$-$C_3$ alkyl are deuterium, hydroxyl, methyl-substituted $C_1$ alkylamino, amino, halogen; the substituent in said substituted $C_1$ alkylamino is methyl; the heteroatoms in said 4-6 membered heterocycle are N, O, and the number of said heteroatom is 1, 2; the heteroatom in said substituted 4-6 membered heterocycle is N, and the number of said heteroatom is 1, 2; the substituents in said substituted 4-6 membered heterocycle are methyl, hydroxyl, halogen;

R³ and R⁴ are halogen;

A is selected from none, O, —NR₁₁—, sulfuryl,

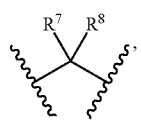

$C_3$ cycloalkyl,

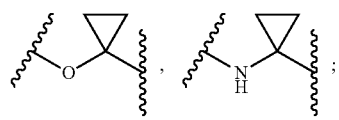

R₁₁ is selected from H, methyl;

R⁵, R⁶, R⁷, R⁸ are independently of each other selected from the group consisting of H, deuterium, halogen, hydroxyl, amino; or any two of R⁵, R⁶, R⁷, and R⁸ are linked to form a 3-4 membered carbocyclic ring.

Further, said compound of formula (I) has the structure of formula (VII):

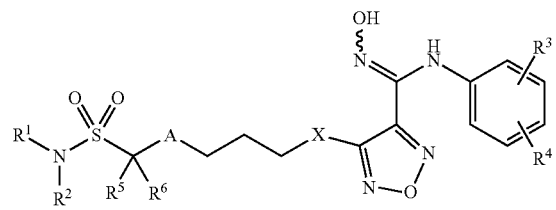

(VII)

Wherein, X is selected from S, —NH—;

R¹ and R² are independently of each other selected from the group consisting of H, hydroxyl, $C_1$-$C_3$ alkyl, substituted $C_1$-$C_3$ alkyl, $C_3$-$C_6$ cycloalkyl, methoxyl, substituted $C_1$ alkylamino; or R¹ and R² are linked to form 4-6 membered heterocycle; or R¹ and R² are linked to form substituted 4-6 membered heterocycle;

The substituents in said substituted $C_1$-$C_3$ alkyl are deuterium, hydroxyl, methyl-substituted $C_1$ alkylamino, amino, halogen; the substituent in said substituted $C_1$ alkylamino is methyl; the heteroatoms in said 4-6 membered heterocycle are N, O, and the number of said heteroatom is 1, 2; the heteroatom in said substituted 4-6 membered heterocycle is N, and the number of said heteroatom is 1, 2; the substituents in said substituted 4-6 membered heterocycle are methyl, hydroxyl, halogen;

R³ and R⁴ are halogen;

A is selected from none, O, —NR₁₁—, sulfuryl,

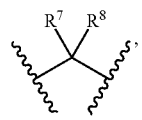

$C_3$ cycloalkyl,

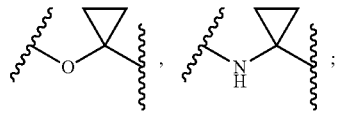 [SMILES: *OC1(*)CC1 ; *NC1(*)CC1]

R₁₁ is selected from hydrogen, methyl;

R⁵, R⁶, R⁷, R⁸ are independently of each other selected from the group consisting of H, deuterium, halogen, hydroxyl, amino; or any two of R⁵, R⁶, R⁷, and R⁸ are linked to form a 3-4 membered carbocyclic ring.

Further, said compound of formula (I) is one of the following:

1

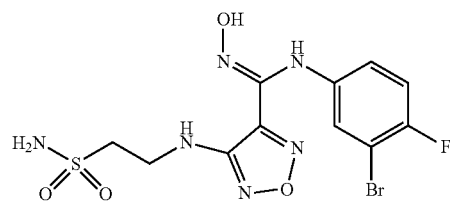

| | |
|---|---|
| 2 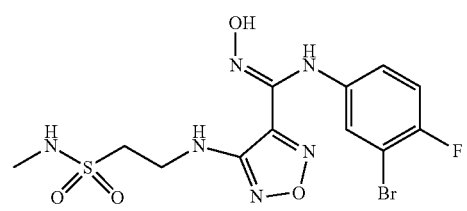 | 9 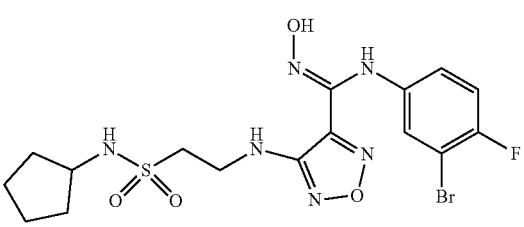 |
| 3 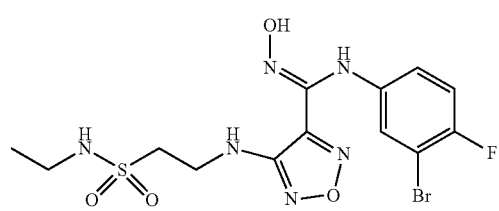 | 10 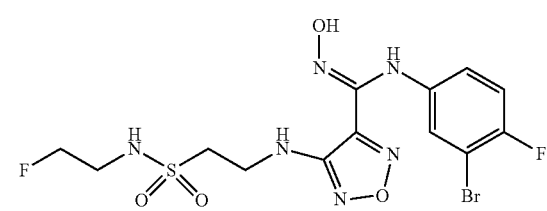 |
| 4 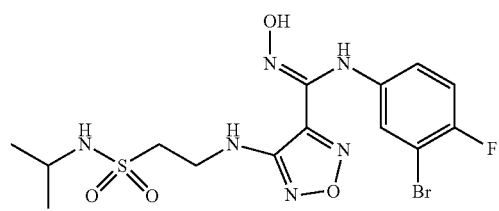 | 11 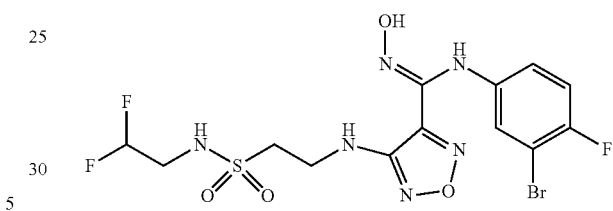 |
| 5 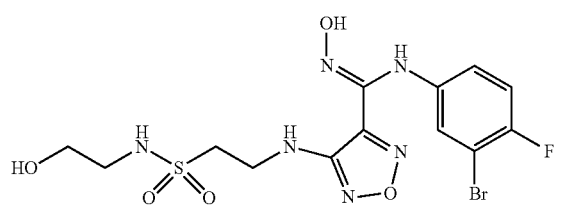 | 12 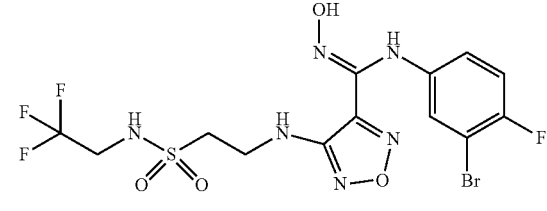 |
| 6 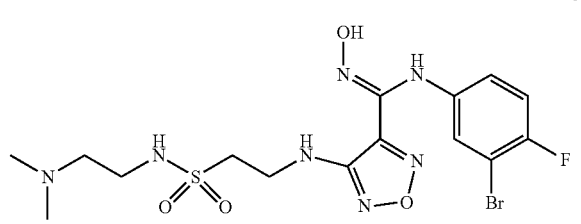 | 13 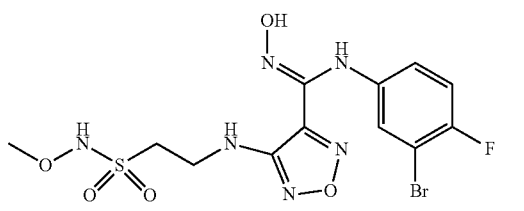 |
| 7 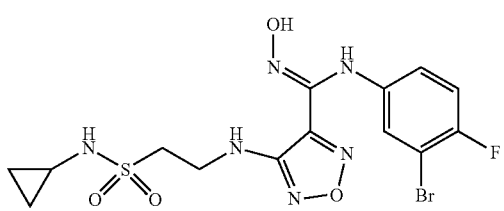 | 14 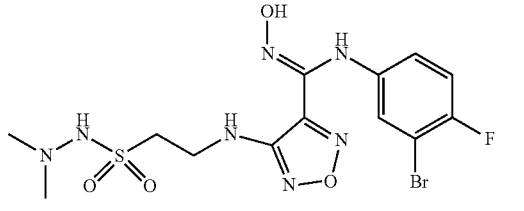 |
| 8 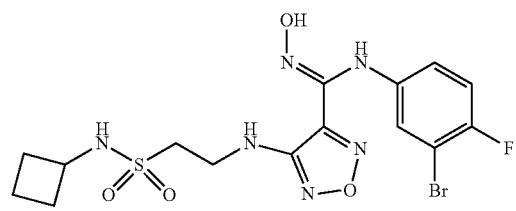 | 15 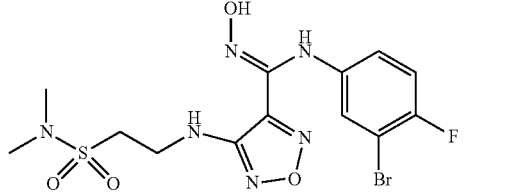 |

16
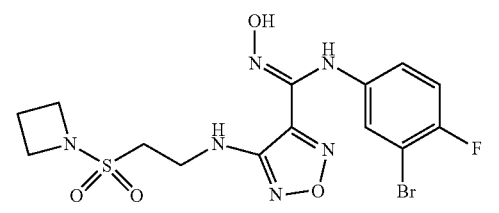
17
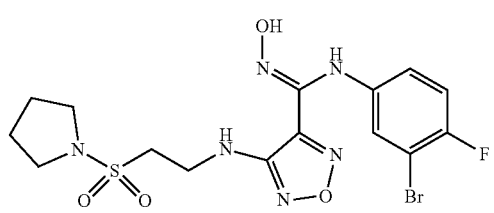
18
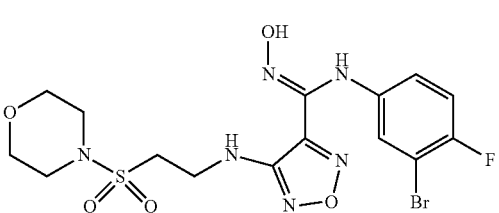
19
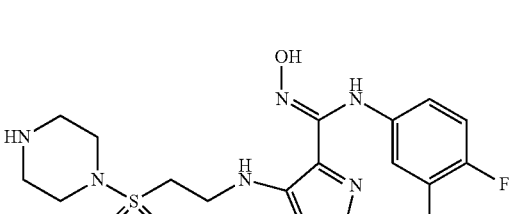
20
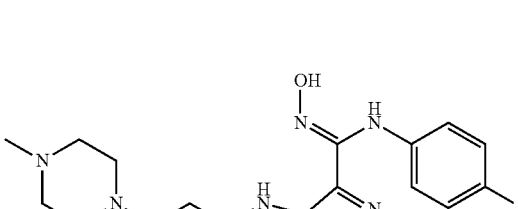
21
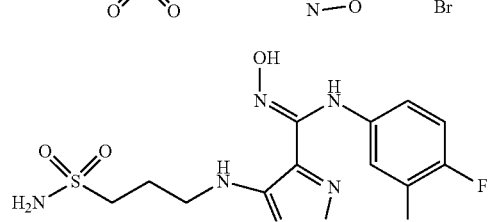
22
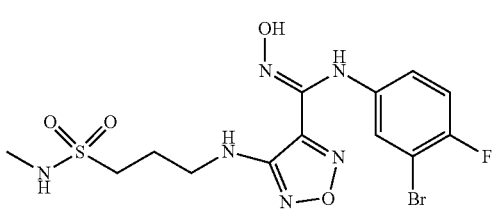
23
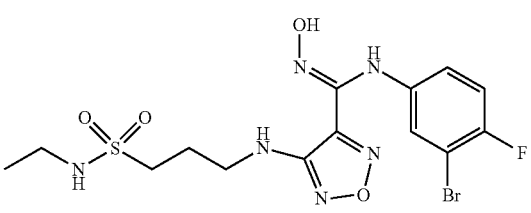
24
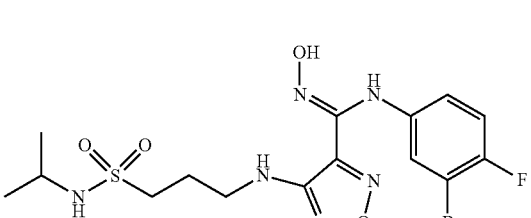
25
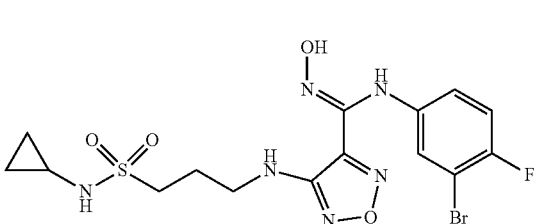
26
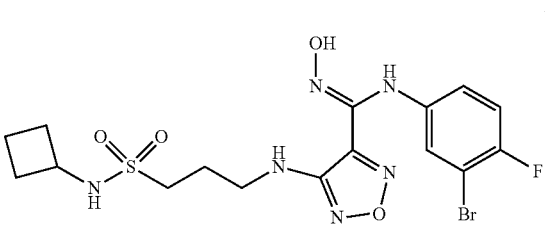
27
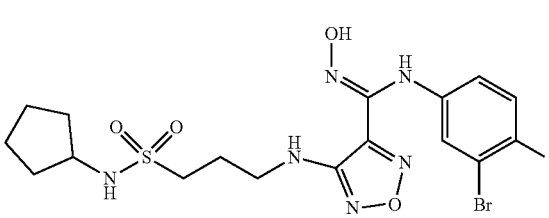
28
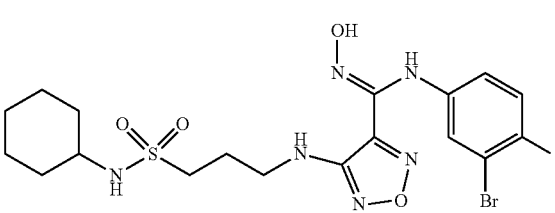
29
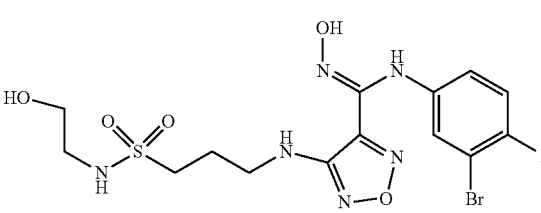

-continued
30
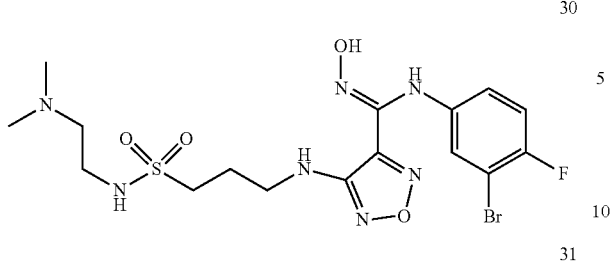
31
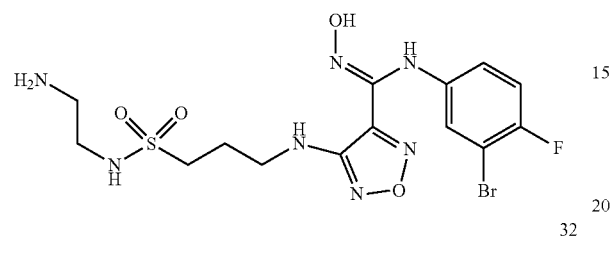
32
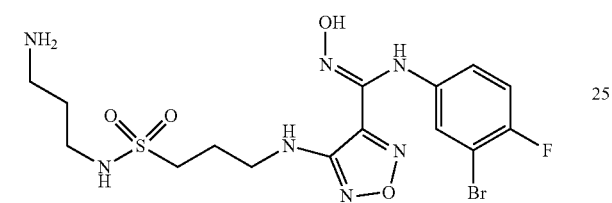
33
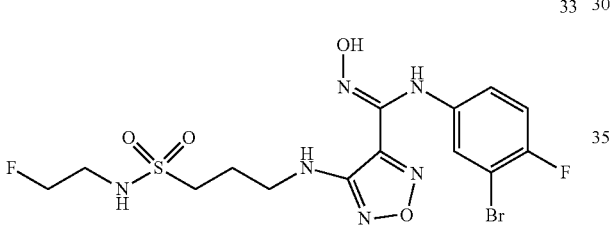
34
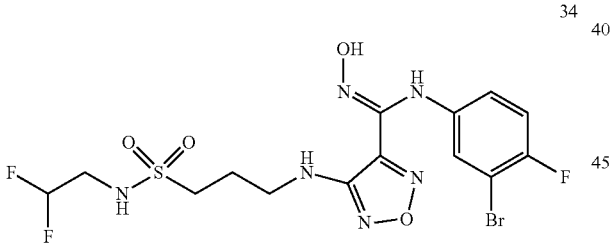
35
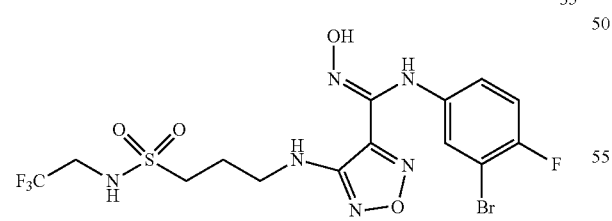
36
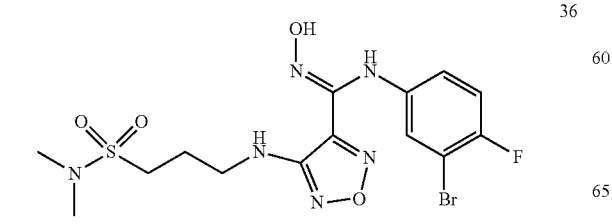
-continued
37
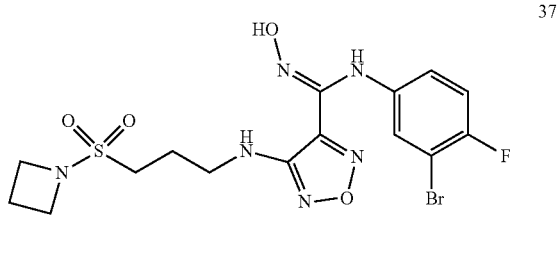
38
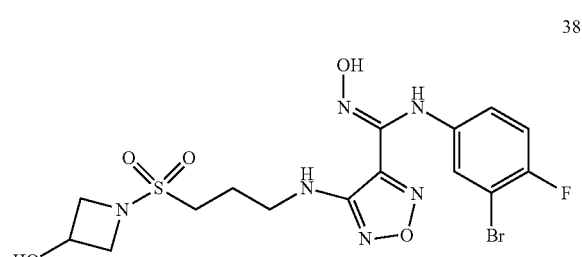
39
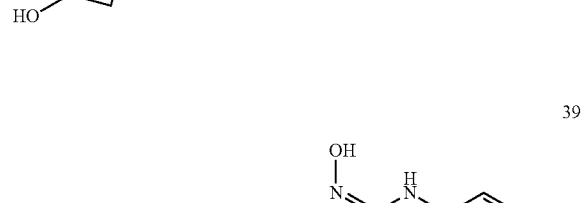
40
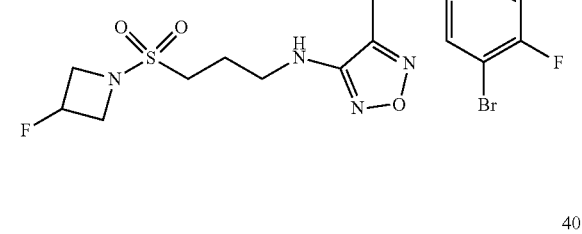
41
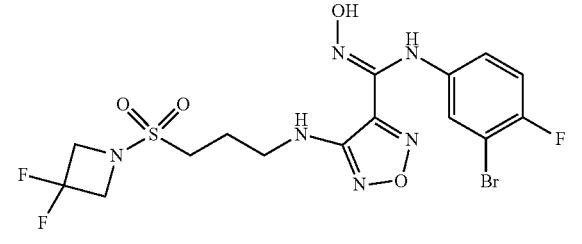
42
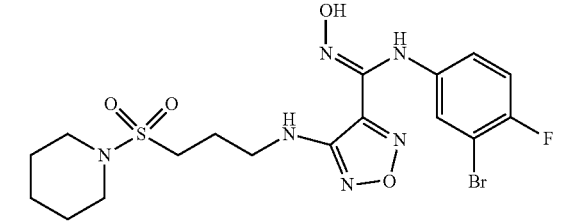

-continued
43
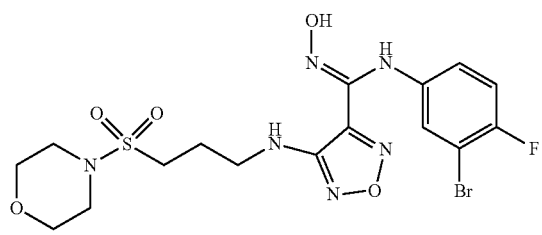
44
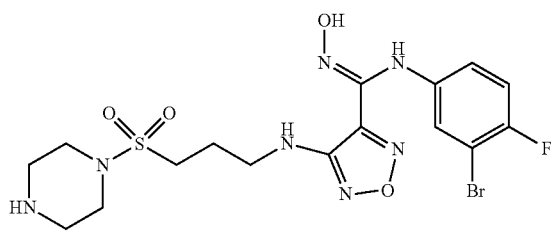
45
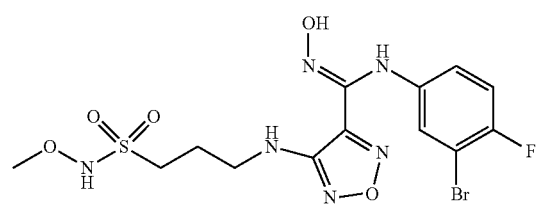
46
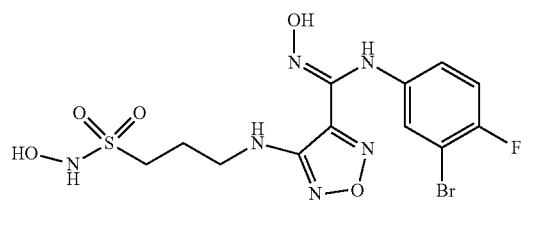
47
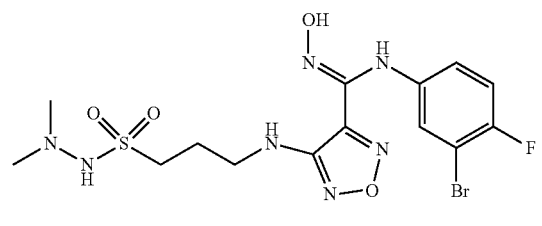
48
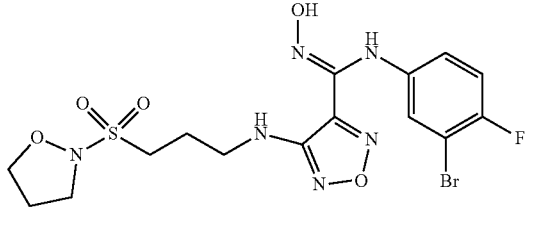
49
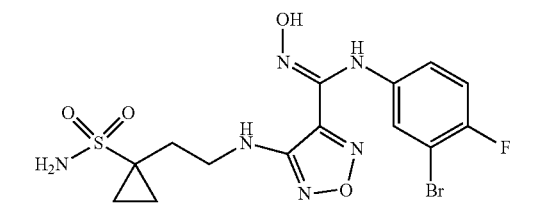
-continued
50
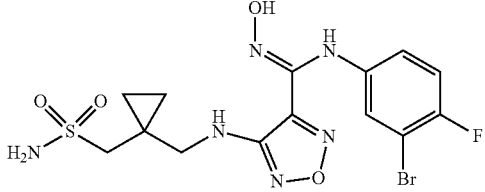
51
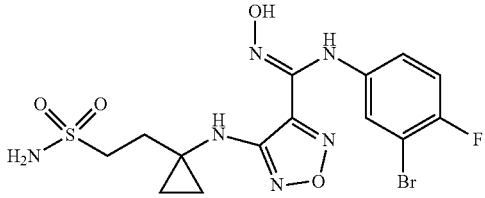
52
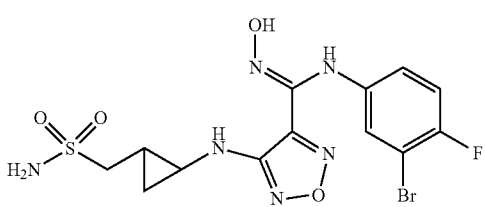
53
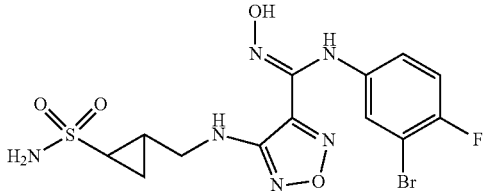
54
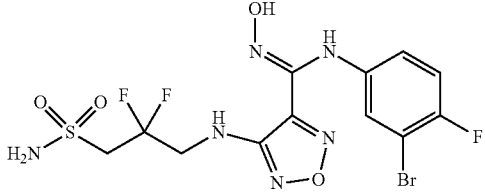
55
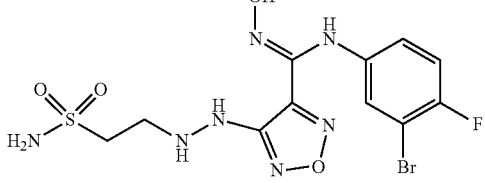
56
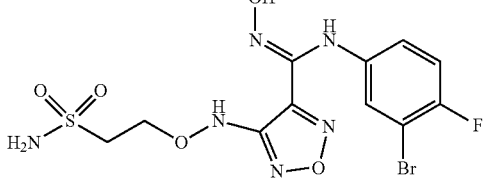

| | |
|---|---|
| 57 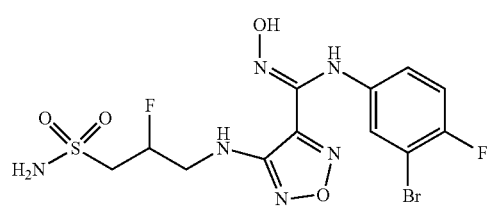 | 64 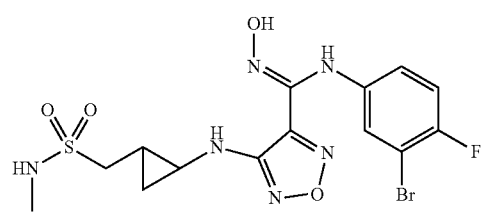 |
| 58 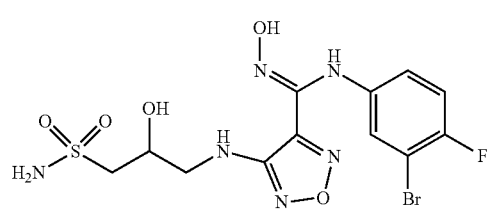 | 65 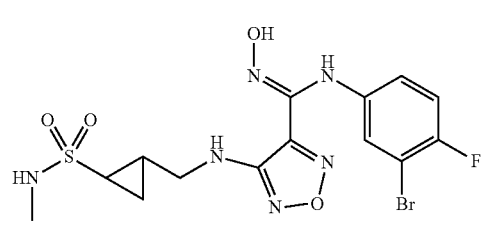 |
| 59 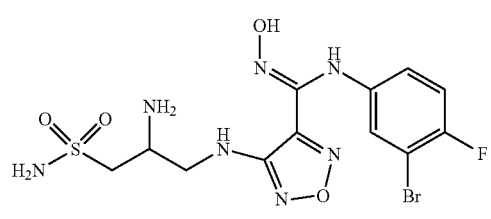 | 66 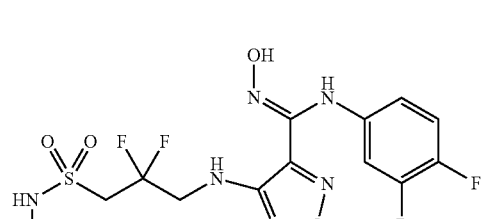 |
| 60 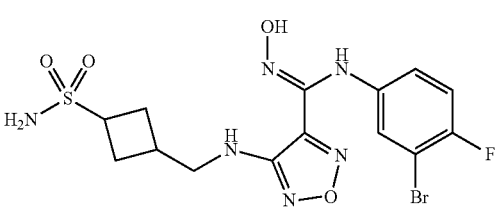 | 67 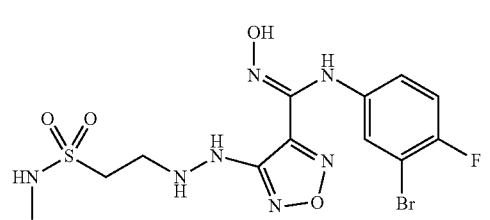 |
| 61 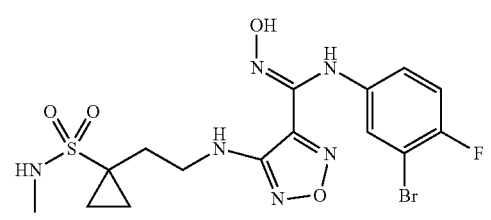 | 68 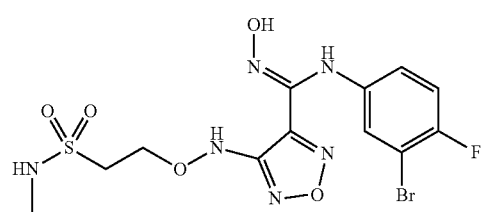 |
| 62 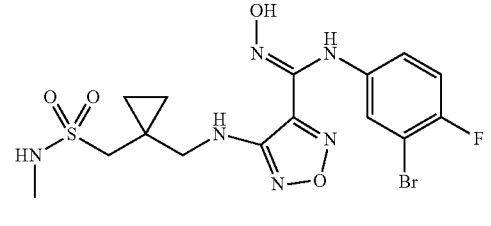 | 69 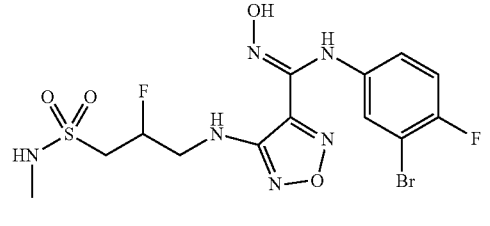 |
| 63 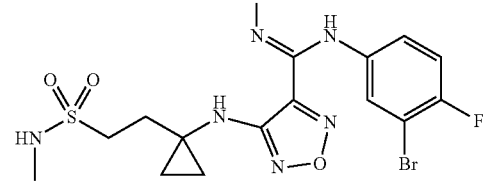 | 70 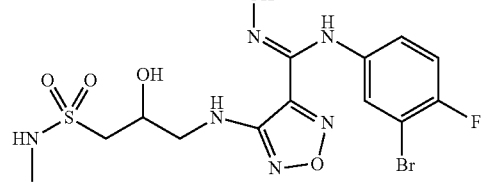 |

| | |
|---|---|
| 71 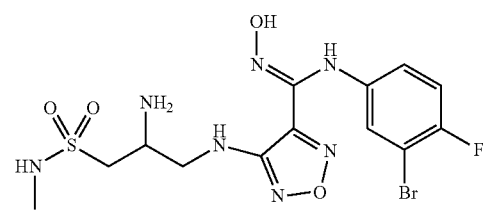 | 78 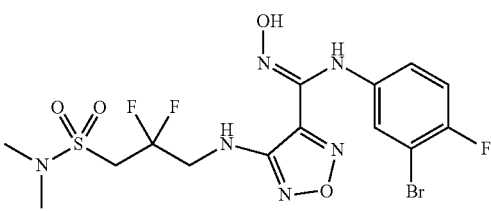 |
| 72 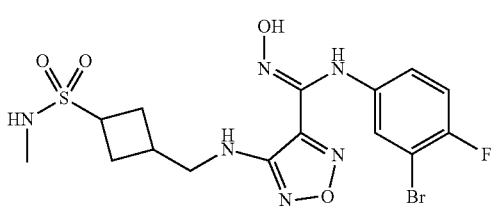 | 79 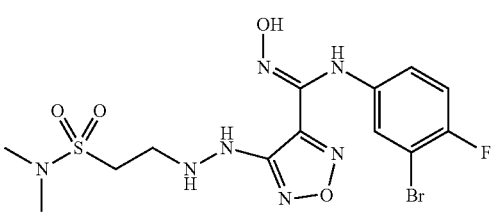 |
| 73 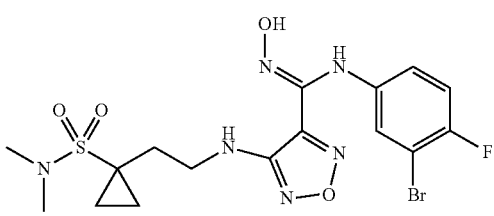 | 80 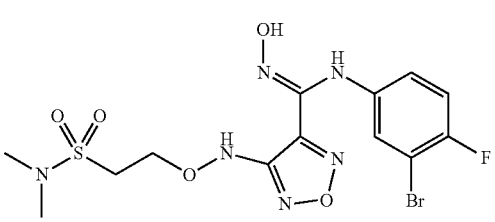 |
| 74 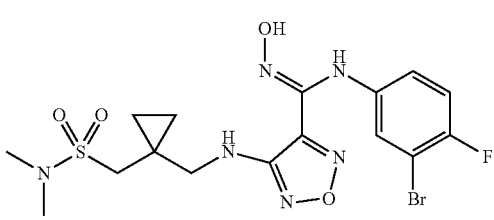 | 81 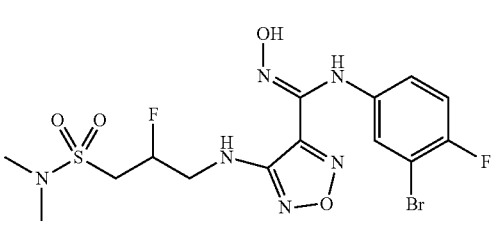 |
| 75 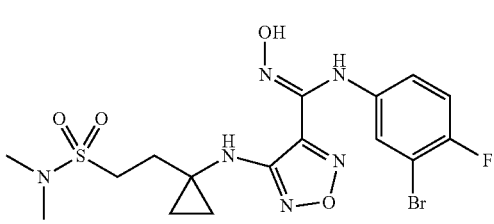 | 82 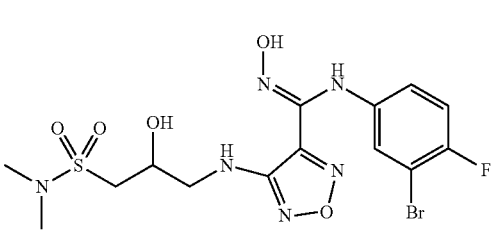 |
| 76 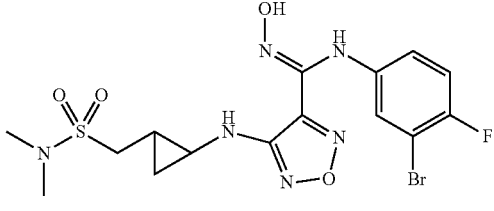 | 83 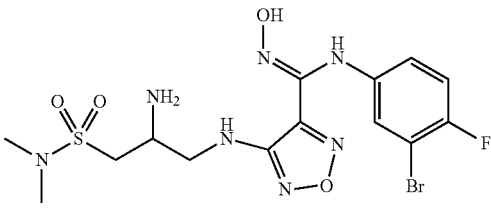 |
| 77 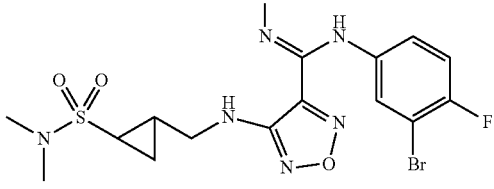 | 84 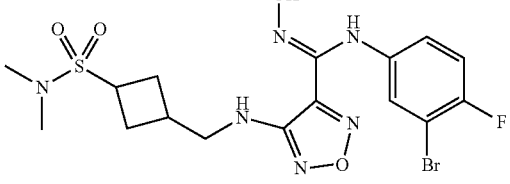 |

85
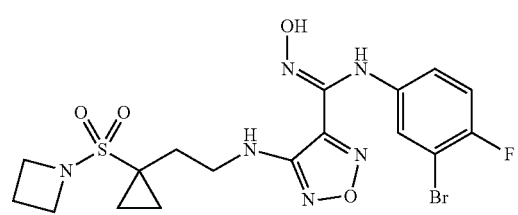
86
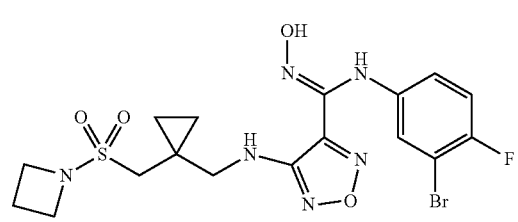
87
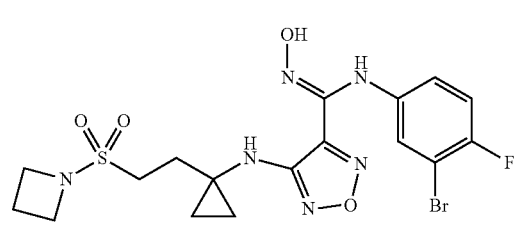
88
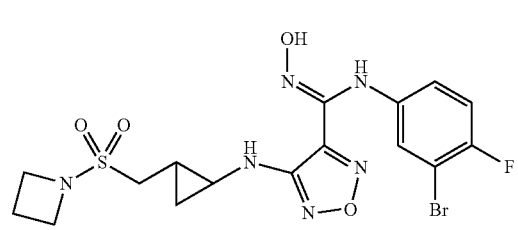
89
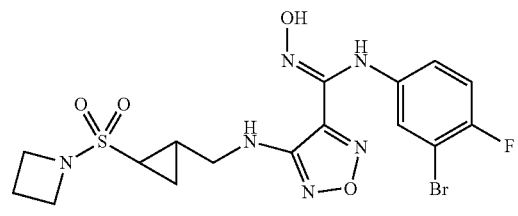
90
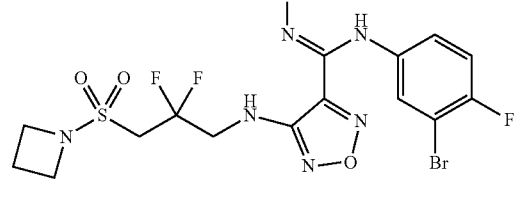
91
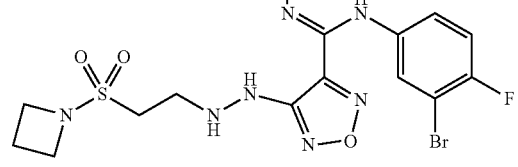
92
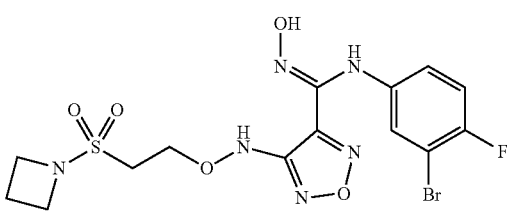
93
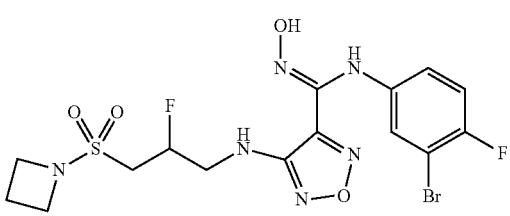
94
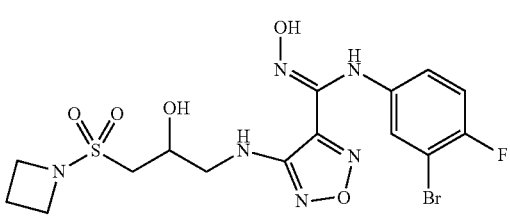
95
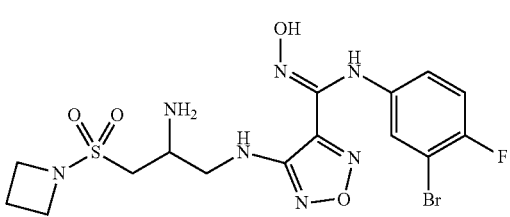
96
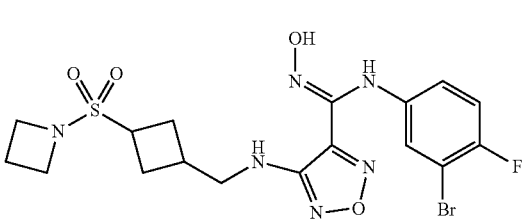
97
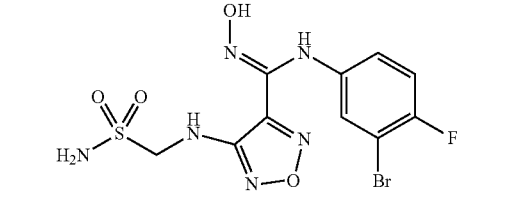
98
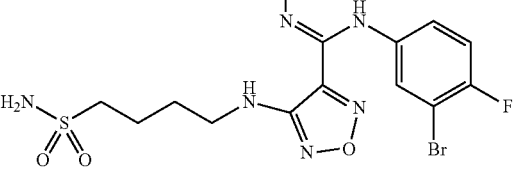

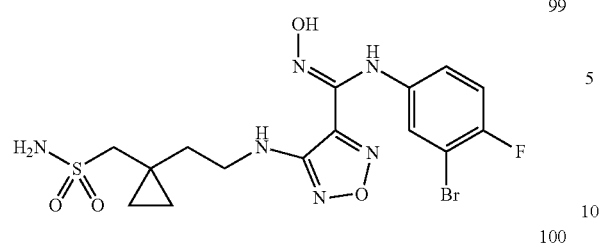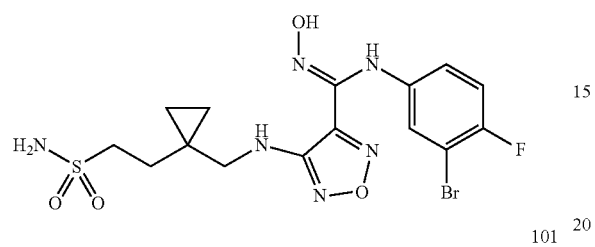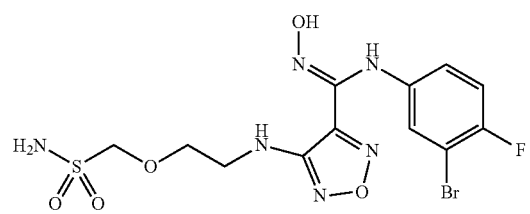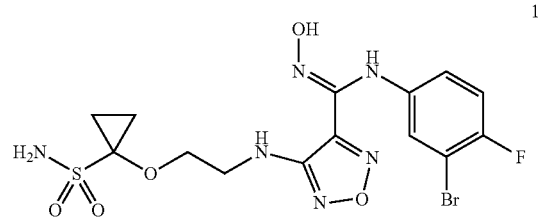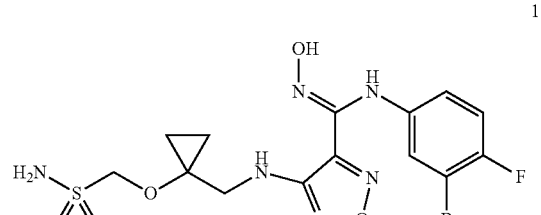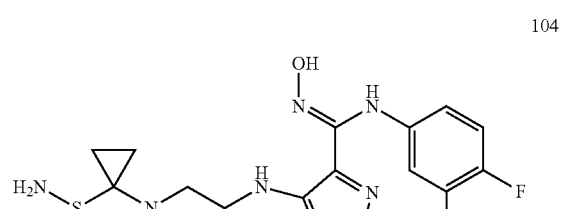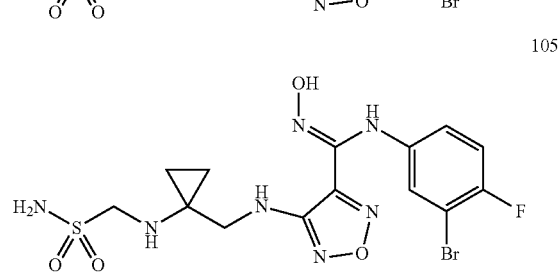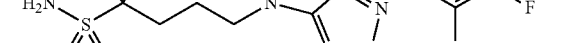

113
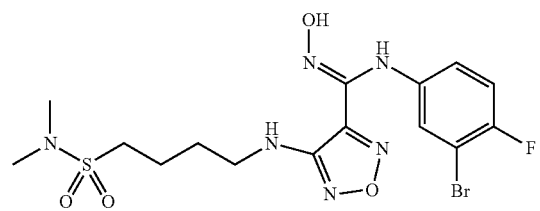
114
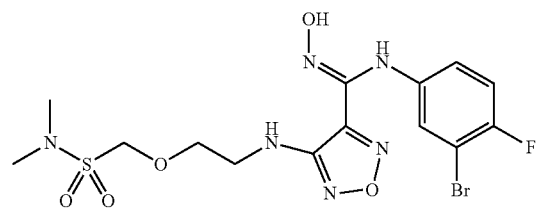
115
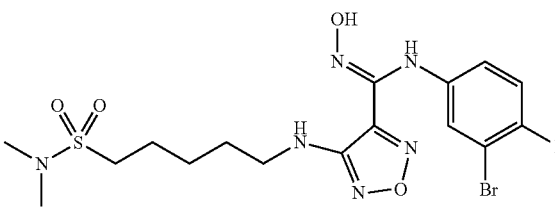
116
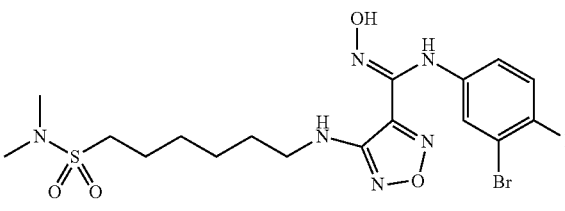
117
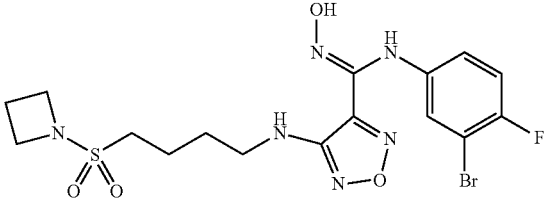
118
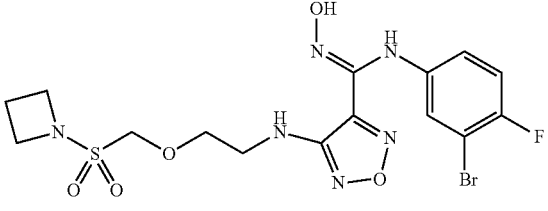
119
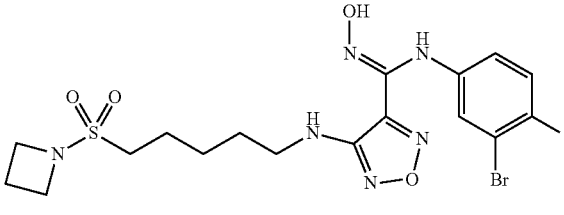
120
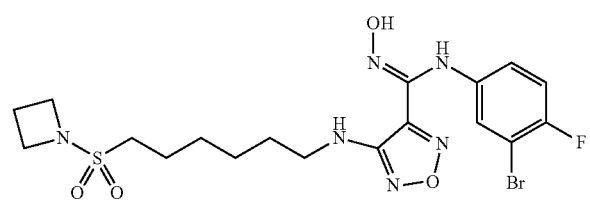
121
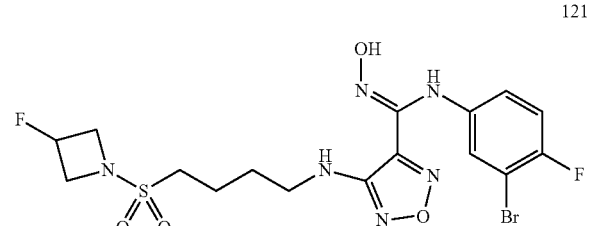
122
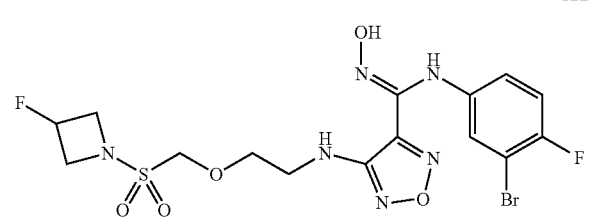
123
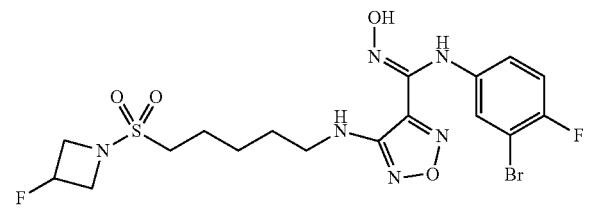
124
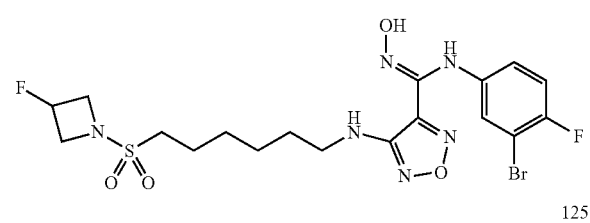
125
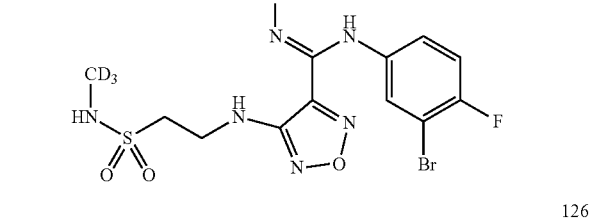
126
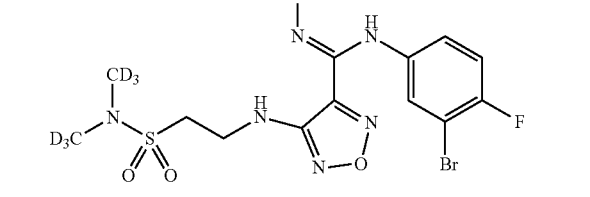

127
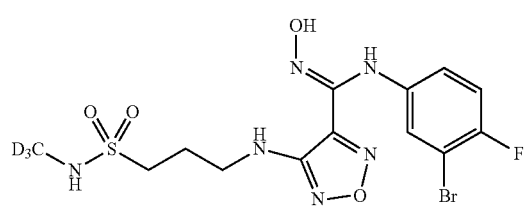
128
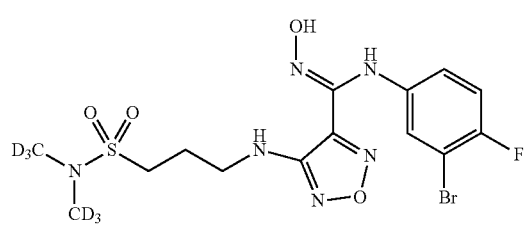
129
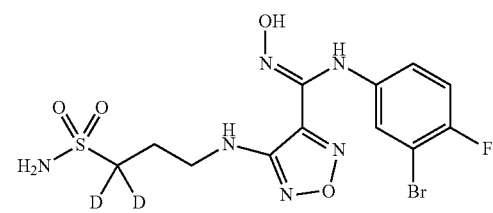
130
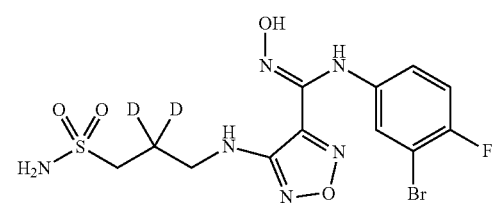
131
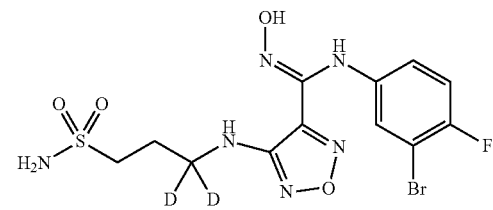
132
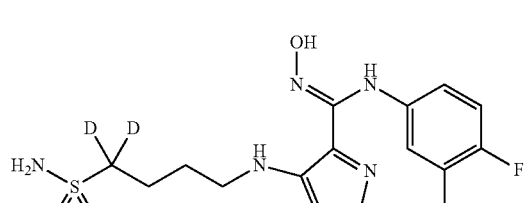
133
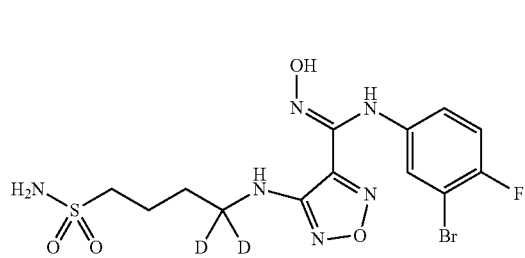
134
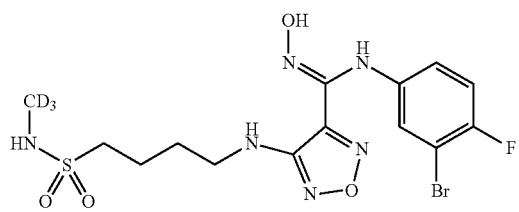
135
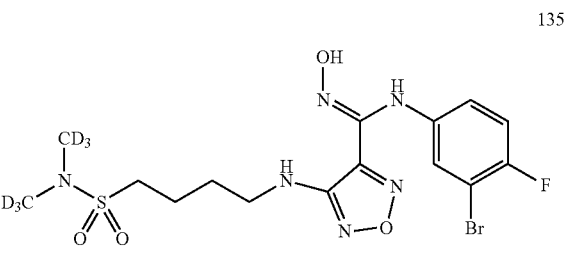
136
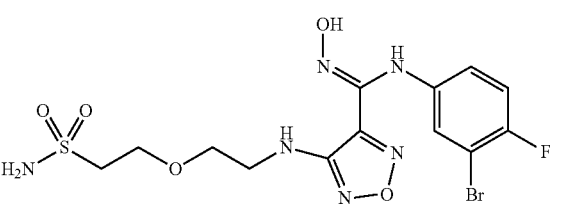
137
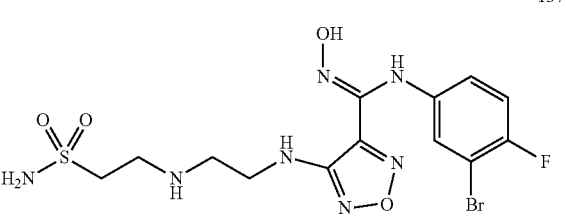
138
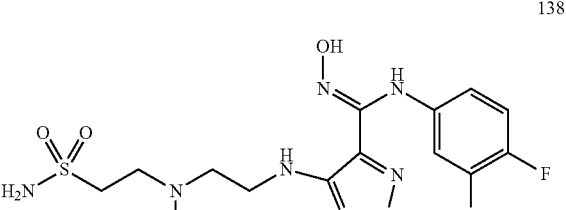
139
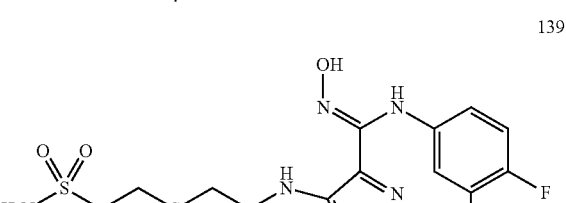
140
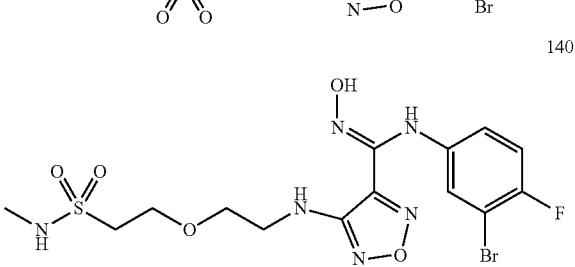

141
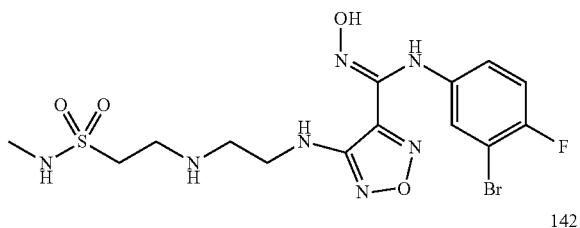

142
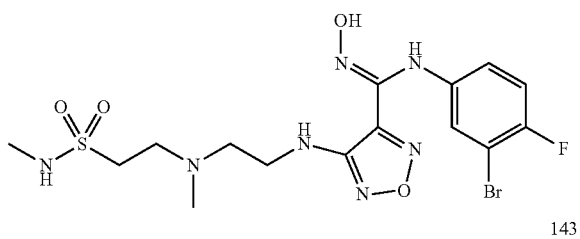

143
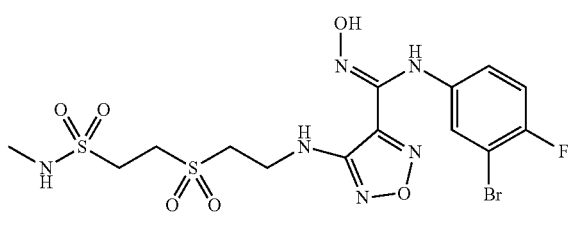

144
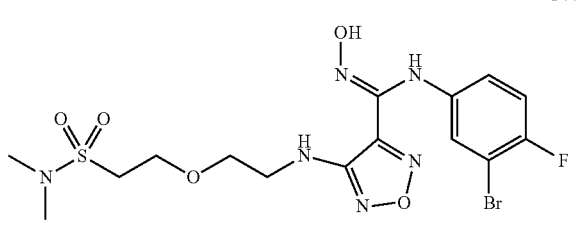

145
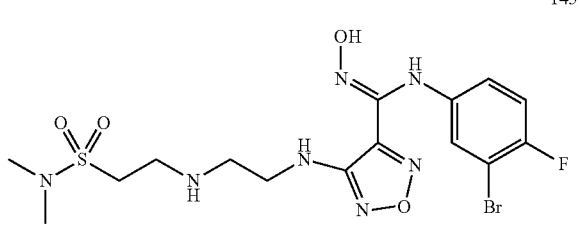

146
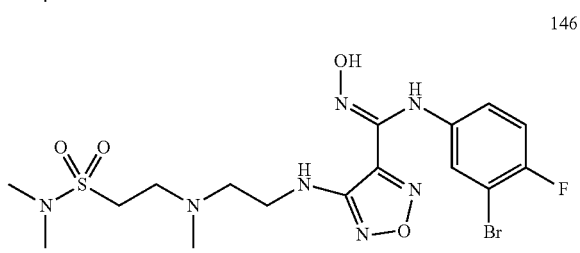

147
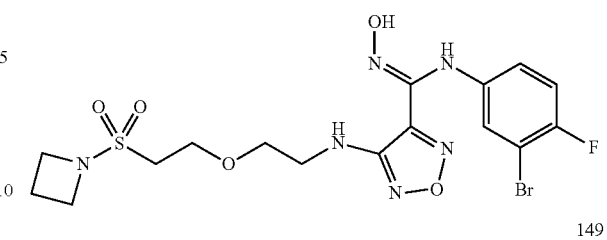

148
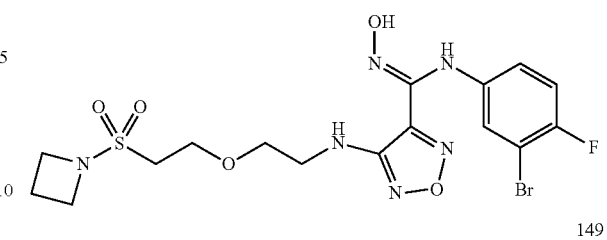

149
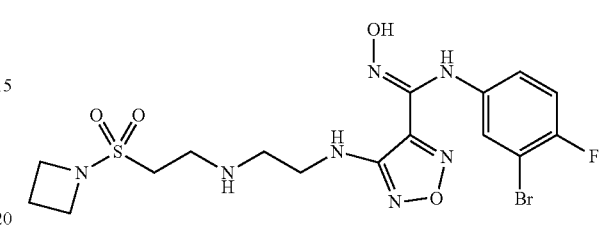

150
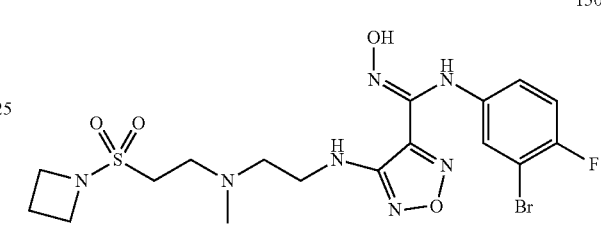

151
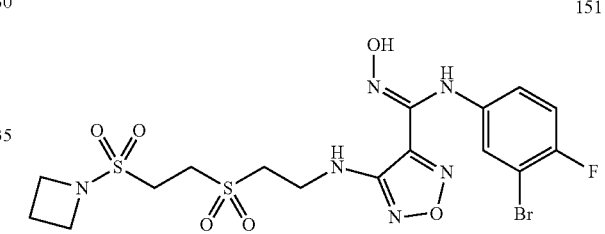

152
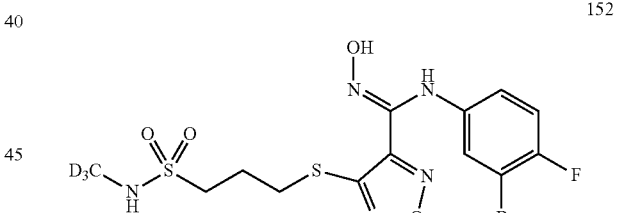

153
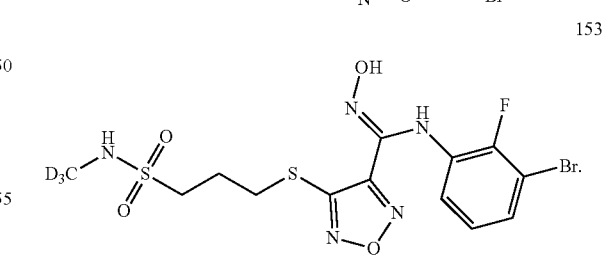

The present invention also provides the use of said compounds, or optical isomers thereof, or cis- and trans-isomers thereof, or isotope compounds thereof, or solvates thereof, or pharmaceutically acceptable salts thereof, or pro-drugs thereof, or tautomers thereof, or mesomers thereof, or racemates thereof, or enantiomers thereof, or diastereoisomers thereof, or mixtures thereof, or metabolites thereof, or metabolic precursors thereof in the preparation of drugs for the prevention and/or treatment of diseases with pathological characteristics of IDO mediated tryptophan metabolism pathway.

Further, said diseases with pathological characteristics of IDO mediated tryptophan metabolism pathway are selected from cancer, myelodysplastic syndrome, Alzheimer's disease, autoimmune disease, depression, anxiety disorder, cataract, psychological disorder and AIDS; in which said cancer is preferably breast cancer, cervical cancer, colon cancer, lung cancer, gastric cancer, rectal cancer, pancreatic cancer, brain cancer, skin cancer, oral cancer, prostate cancer, bone cancer, kidney cancer, ovarian cancer, bladder cancer, liver cancer, fallopian tube tumor, ovarian tumor, peritoneal tumor, stage IV melanoma, solid tumor, glioma, neuroglioblastoma, hepatocyte cancer, and mastoid nephroma.

The present invention further provides a drug combination, that is prepared by using said compounds, or optical isomers thereof, or cis- and trans-isomers thereof, or isotope compounds thereof, or solvates thereof, or pharmaceutically acceptable salts thereof, or pro-drugs thereof, or tautomers thereof, or mesomers thereof, or racemates thereof, or enantiomers thereof, or diastereoisomers thereof, or mixtures thereof, or metabolites thereof, or metabolic precursors thereof as active ingredients, with the addition of pharmaceutically acceptable adjuvants.

The present invention further provides the use of said drug combination in the preparation of drugs for the prevention and/or treatment of diseases with pathological characteristics of IDO mediated tryptophan metabolism pathway.

Further, said diseases with pathological characteristics of IDO mediated tryptophan metabolism pathway are selected from cancer, myelodysplastic syndrome, Alzheimer's disease, autoimmune disease, depression, anxiety disorder, cataract, psychological disorder and AIDS; in which said cancer is preferably breast cancer, cervical cancer, colon cancer, lung cancer, gastric cancer, rectal cancer, pancreatic cancer, brain cancer, skin cancer, oral cancer, prostate cancer, bone cancer, kidney cancer, ovarian cancer, bladder cancer, liver cancer, fallopian tube tumor, ovarian tumor, peritoneal tumor, stage IV melanoma, solid tumor, glioma, neuroglioblastoma, hepatocyte cancer, and mastoid nephroma.

For the definitions of terms used in the present invention: unless otherwise specified, the initial definitions of groups or terms provided herein are applicable to the groups or terms throughout the specification; for terms not specifically defined herein, it should be given the meaning that those skilled in the art can give them based on the disclosure and context.

"Substitution" means that the hydrogen atom in the molecule is replaced by other different atoms or molecules.

The minimum and maximum values of carbon atom content in the hydrocarbon group are indicated by a prefix, for example, the prefix $(C_a\sim C_b)$ alkyl indicates any alkyl group having "a"~"b" carbon atoms. Therefore, for example, $(C_1\sim C_4)$alkyl means an alkyl containing 1~4 carbon atoms.

$C_1\sim C_6$ alkyl denotes $C_1$, $C_2$, $C_3$, $C_4$, $C_5$, $C_6$ alkyl, that is linear or branched alkyl having 1-6 carbon atoms, such as methyl, ethyl, propyl, isopropyl, butyl, isobutyl, tert-butyl, sec-butyl, pentyl, hexyl, etc. $C_1$-$C_6$ alkoxyl, $C_3$-$C_7$ cycloalkyl, and $C_3$-$C_7$heterocycloalkyl also have the meaning corresponding to the group. For example, the $C_3$-$C_6$ cycloalkyl denotes $C_3$, $C_4$, $C_5$, $C_6$ cycloalkyl, i.e. a cycloalkyl having 3~6 carbon atoms, such as cyclopropyl, cyclobutyl, cyclopentyl, cyclohexyl, etc.

The term "pharmaceutically acceptable" means that carriers, vectors, diluents, excipients and/or salts formed are chemically or physically compatible with other components consisting of a pharmaceutical dosage, and physiologically compatible with the receptor.

The terms "salts" and "pharmaceutically acceptable salts" denote acid and/or basic salts of above-mentioned compounds or their stereoisomers formed with inorganic and/or organic acids and bases, and also include zwitterionic salts (internal salt), and further include quaternary ammonium salts, such as alkyl ammonium salts. These salts can be directly obtained in the final isolation and purification of the compound. It can also be obtained by mixing above-mentioned compound or its stereoisomer with a certain amount of acid or base appropriately (for example, equivalent). These salts may precipitate in the solution and be collected by filtration, or recovered after evaporation of the solvent, or prepared by freeze-drying after reaction in an aqueous medium.

The salt in the present invention can be hydrochloride, sulfate, citrate, benzenesulfonate, hydrobromide, hydrofluoride, phosphate, acetate, propionate, succinate, oxalate, malate, succinate, fumarate, maleate, tartrate or trifluoroacetate.

The isotopic compound of the present invention is the one in which one or more elements are substituted with their corresponding isotopes, including but not limited to hydrogen (H) being substituted with deuterium (D) or tritium (T).

Staying overnight in the present invention is 12 h-16 h.

The compounds prepared in the present invention have significant inhibitory activity against IDO protease, and the in vivo metabolism is stable, showing good pharmacokinetics. Especially, the metabolic stability via human liver microsomes is better than that of the similar compound INCB024360, which has entered the clinic, indicating that the compound of the present invention may have better clinical pharmacokinetics. The compound of the present invention or the pharmaceutical composition can be used to prepare IDO inhibitory drugs, and can also be used to prepare drugs for preventing and/or treating diseases with pathological characteristics of IDO-mediated tryptophan metabolism pathway, with wide application value.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

General synthetic method of compound according to the present invention is as follows:

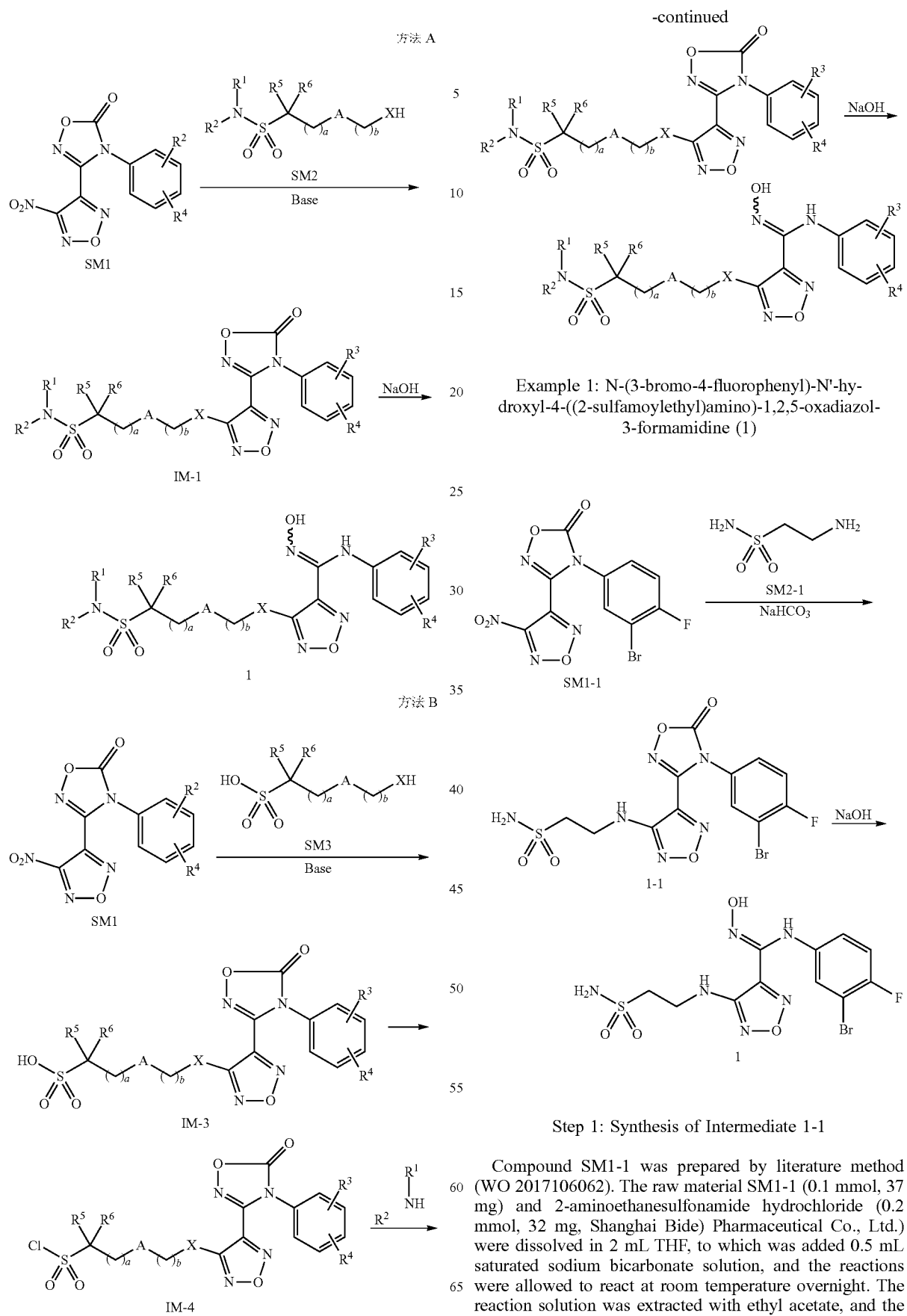

Example 1: N-(3-bromo-4-fluorophenyl)-N'-hydroxyl-4-((2-sulfamoylethyl)amino)-1,2,5-oxadiazol-3-formamidine (1)

Step 1: Synthesis of Intermediate 1-1

Compound SM1-1 was prepared by literature method (WO 2017106062). The raw material SM1-1 (0.1 mmol, 37 mg) and 2-aminoethanesulfonamide hydrochloride (0.2 mmol, 32 mg, Shanghai Bide) Pharmaceutical Co., Ltd.) were dissolved in 2 mL THF, to which was added 0.5 mL saturated sodium bicarbonate solution, and the reactions were allowed to react at room temperature overnight. The reaction solution was extracted with ethyl acetate, and the organic phase was successively washed with 0.5N hydrochloric acid and saturated brine. After separating the organic phase, the organic layer was concentrated under reduced pressure. The obtained crude product was purified by thin-layer chromatography to obtain 22 mg white solid (intermediate 1-1), with a yield of 48%.

Step 2: Synthesis of Compound 1

Intermediate 1-1 (22 mg, 0.05 mmol) was dissolved in 2 mL THF, and 0.5 mL of 2N NaOH was added, then the mixture was stirred at room temperature for 0.5 h. The reaction solution was extracted with ethyl acetate, and the organic phase was washed with distilled water and then with saturated brine. After the organic phase was separated, it was rotatory dried by rotatory evaporator under reduced pressure to obtain 20 mg off-white solid (compound 1) with a yield of 95%.

MS m/z(ESI): 423.0 [M+H]$^+$ $^1$H NMR (400 MHz, DMSO-d$_6$) δ11.46 (s, 1H), 8.88 (s, 1H), 7.18 (t, J=8.8 Hz, 1H), 7.10 (dd, J=6.0, 2.7 Hz, 1H), 6.97 (d, J=16.2 Hz, 2H), 6.80-6.72 (m, 1H), 6.48 (dd, J=13.2, 7.2 Hz, 1H), 3.71-3.55 (m, 2H), 3.29 (t, J=6.8 Hz, 2H).

Example 2: N-(3-bromo-4-fluorophenyl)-N'-hydroxyl-4-((2-(N-methylsulfamoyl)ethyl)amino)-1,2,5-oxadiazol-3-formamidine(2)

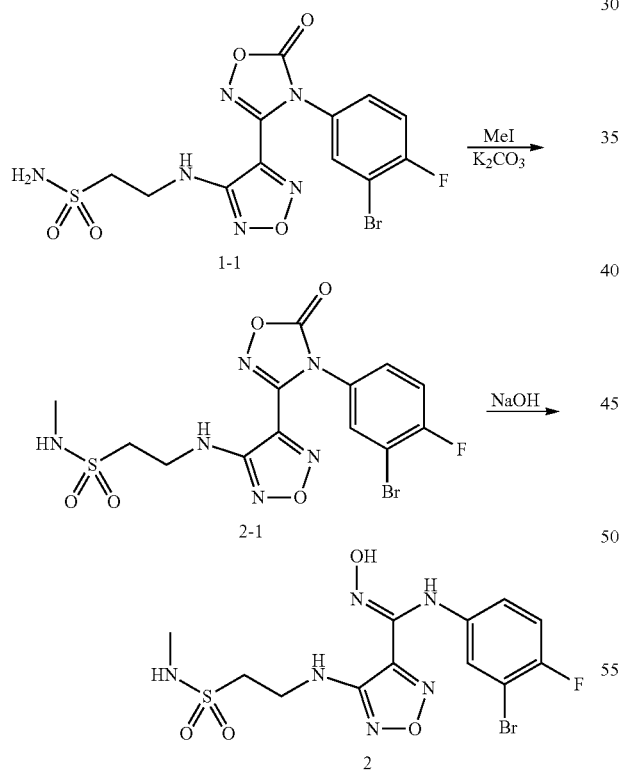

Step 1: Synthesis of Intermediate 2-1

Intermediate 1-1 (113 mg, 0.25 mmol) and potassium carbonate (70 mg, 0.5 mmol) were sequentially added to DMF (5 mL), then methyl iodide (36 mg, 0.25 mmol) was slowly added, and the mixture was stirred overnight at room temperature. TLC was used to monitor the reaction till the raw materials disappeared. 10 mL water was added, and the mixture was extracted with 20 mL ethyl acetate. The organic layer was washed with saturated brine, dried with anhydrous sodium sulfate, and purified by prep-TLC, using ethyl acetate/n-hexane=1/1 as development solvents, to obtain 20 mg intermediate 2-1. Yield: 17%.

Intermediate 2-1 (20 mg, 0.04 mmol) was added to 5 mL tetrahydrofuran, then 1.5 mL of sodium hydroxide (2N) solution was added, and the reaction was stirred at room temperature for 30 minutes. TLC was used to monitor the disappearance of raw materials. 10 mL water was added, and the reaction mixture was extracted with 10 mL ethyl acetate. The organic layer was washed with saturated brine, dried with anhydrous sodium sulfate, and concentrated under reduced pressure to obtain 15 mg white solid (compound 2), yield: 85%.

MS (ESI) m/e 437.0 (M+H)+.

Example 3: N-(3-bromo-4-fluorophenyl)-N'-hydroxyl-4-((2-(N-ethylsulfamoyl)ethyl)amino)-1,2,5-oxadiazol-3-formamidine(3)

Compound 3 was prepared by a synthetic method similar to Example 1 using SM1-1 and SM2-3 as starting materials.

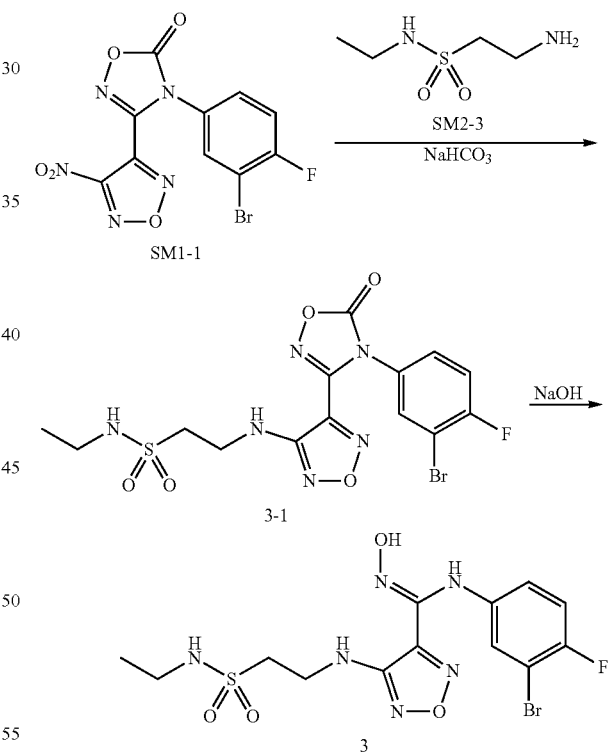

Step 1: Synthesis of SM2-3

Ethylamine hydrochloride (81.5 mg, 1.0 mmol) was dissolved in 5 mL DCM, then triethylamine (303 mg, 3.0 mmol) was added, and 2-phthalimidoethanesulfonyl chloride (273 mg, 1.0 mmol) was slowly added on ice bath, and the mixture was allowed to react for 15 min. TLC was used to monitor the reaction until the raw material disappeared. 10 mL water was added, then extracted with 10 mL DCM.

The organic layer was washed with saturated brine, dried over anhydrous sodium sulfate, concentrated to dryness under reduced pressure, and purified by thin layer chromatography (DCM/MeOH=10:1) to obtain 65 mg white solid product. Yield: 23%.

The white solid product (65 mg, 0.23 mmol) was dissolved in 5 mL ethanol, to which was added hydrazine hydrate (17.7 mg, 0.29 mmol), and the mixture was stirred under reflux for 3 h till white solid precipitated out. The reactions were naturally cooled to room temperature, filtered, and the filtrate was concentrated to dryness under reduced pressure, to provide 28 mg white solid (SM2-3), with a yield of 80%.

Step 2: Synthesis of Intermediate 3-1

SM1-1 (34 mg, 0.09 mmol) was dissolved in 5 mL tetrahydrofuran, to which were sequentially added SM2-3 (28 mg, 0.18 mmol) and saturated NaHCO₃ aqueous solution (0.1 mL) under stirring, then the reaction was further stirred at room temperature for 30 min. TLC was used to monitor the reaction until the raw material disappeared. 10 mL water was added, and extracted with 10 mL ethyl acetate. The organic layer was washed twice with saturated brine, concentrated under reduced pressure to dryness, and purified by thin layer chromatography (PE/Ea=1:1), to provide 28 mg white solid (intermediate 3-1), with a yield of 65%.

Step 3: Synthesis of Compound 3

Intermediate 3-1 (28 mg, 0.059 mmol) was dissolved in 1 mL THF, then 0.3 mL of 2 N NaOH was added, and the reaction was stirred at room temperature for 30 minutes. TLC was used to monitor the disappearance of raw materials. 10 mL water was added, and the reaction mixture was extracted with 10 mL ethyl acetate. The organic layer was washed with saturated brine twice, dried with anhydrous sodium sulfate, and concentrated under reduced pressure to dry, to provide 20 mg target compound as white solid, with a yield of 75%.

MS (ESI) m/z 451 [M+H]⁺

¹H NMR (400 MHz, DMSO) δ 11.47 (s, 1H), 8.91 (s, 1H), 7.25-7.15 (m, 2H), 7.10 (dd, J=6.0, 2.6 Hz, 1H), 6.76 (dd, J=7.5, 4.4 Hz, 1H), 6.44 (t, J=6.0 Hz, 1H), 3.59 (dd, J=12.8, 6.4 Hz, 2H), 3.31-3.26 (m, 2H), 2.98 (dt, J=14.1, 7.1 Hz, 2H), 1.09 (t, J=7.2 Hz, 3H).

Example 4: N-(3-bromo-4-fluorophenyl)-N'-hydroxyl-4-((2-(isopropylsulfamoyl)ethyl)amino)-1,2,5-oxadiazol-3-formamidine(4)

Compound 4 was prepared by a synthetic method similar to Example 1 using SM1-1 and SM2-4 as starting materials.

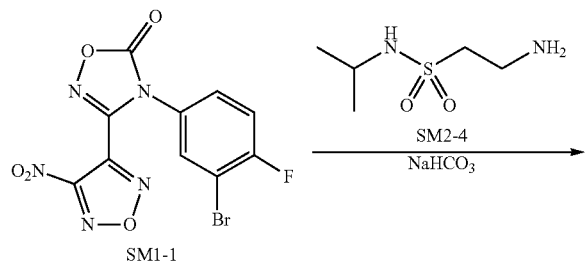

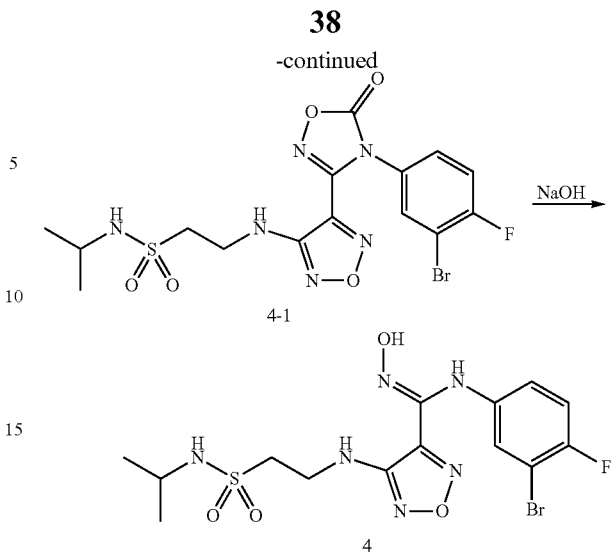

Step 1: Synthesis of 5SM2-4

2-Phthalimidoethanesulfonyl chloride (273 mg, 1.0 mmol) was dissolved in 3 mL DCM, to which was added isopropylamine (177 mg, 3.0 mmol) under stirring, and the mixture was allowed to react at room temperature for 30 min. The reaction was monitored by TLC until the starting material disappeared. 10 ml water was added and then extracted with 10 ml DCM. DCM layer was washed with saturated brine and dried over anhydrous sodium sulfate. After filtration, the filtrate was dried by rotatory evaporator under reduced pressure to remove the solvent, and 202 mg product was obtained as white solid. Yield: 68%.

The white solid (98 mg, 0.33 mmol) was dissolved in 5 mL ethanol, to which was added hydrazine hydrate (22 mg, 0.36 mmol), and the mixture was stirred under reflux for 3 h till white solid precipitated out. The reactions were naturally cooled to room temperature, filtered, and the filtrate was concentrated to dryness under reduced pressure, to provide 45 mg white solid (SM2-4), with a yield of 82%.

Step 2: Synthesis of Intermediate 4-1

SM1-1 (82 mg, 0.135 mmol) was dissolved in 5 mL tetrahydrofuran, to which were sequentially added SM2-4 (45 mg, 0.27 mmol) and saturated NaHCO₃ aqueous solution (0.14 mL) under stirring, then the reaction was further stirred at room temperature for 30 min. TLC was used to monitor the reaction until the starting material disappeared. 10 mL water was added, and extracted with 10 mL ethyl acetate. The organic layer was washed twice with saturated brine, concentrated under reduced pressure to dryness, and purified by thin layer chromatography (PE/Ea=2:1), to provide 40 mg product as white solid (intermediate 4-1), with a yield of 60%.

Step 3: Synthesis of Compound 4

Intermediate 4-1 (40 mg, 0.08 mmol) was dissolved in 1 mL THF, then 2 N NaOH (0.4 ml, 0.8 mmol) was added, and the reaction was stirred at room temperature for 30 minutes. TLC was used to monitor the disappearance of starting materials. 10 mL water was added, and the reaction mixture was extracted with 10 mL ethyl acetate. The organic layer was washed with saturated brine twice, dried with anhydrous sodium sulfate, and concentrated under reduced pressure to dry, to provide 32 mg target compound as white solid, with a yield of 84.5%.

MS (ESI) m/e 465 (M+H)+

$^1$H NMR (400 MHz, DMSO) δ 11.46 (s, 1H), 8.90 (s, 1H), 7.23-7.15 (m, 2H), 7.10 (dd, J=6.0, 2.7 Hz, 1H), 6.79-6.73 (m, 1H), 6.45 (t, J=6.0 Hz, 1H), 3.59 (dd, J=13.2, 6.4 Hz, 2H), 3.43 (dd, J=13.3, 6.5 Hz, 1H), 3.28 (t, J=6.9 Hz, 2H), 1.13 (d, J=6.5 Hz, 6H).

Example 5: N-(3-bromo-4-fluorophenyl)-N'-hydroxyl-4-((2-(N-(2-hydroxylethyl)sulfamoyl)ethyl)amino)-1,2,5-oxadiazol-3-formamidine(5)

Compound 5 was prepared by a synthetic method similar to Example 1 using SM1-1 and SM2-5 as starting materials.

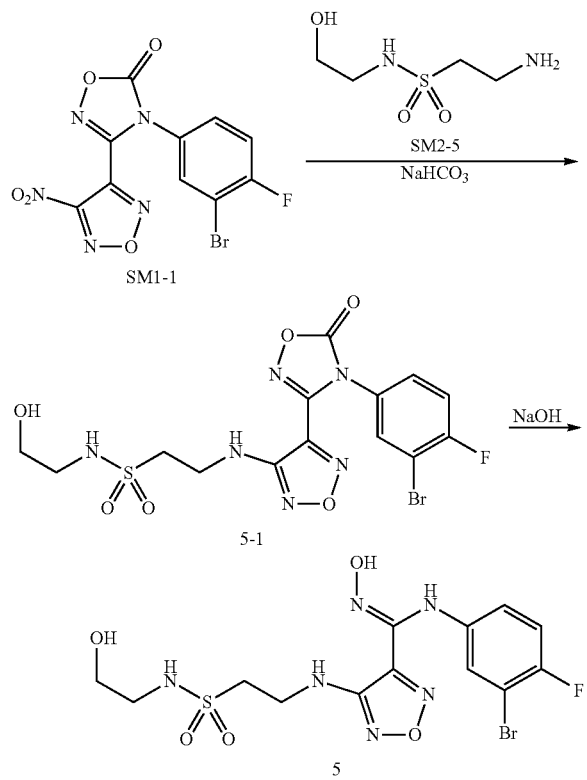

Step 1: Synthesis of SM2-5

2-Phthalimidoethanesulfonyl chloride (273 mg, 1.0 mmol) was dissolved in 3 mL DCM, to which were sequentially added ethanolamine (61 mg, 1.0 mmol) under stirring and triethylamine (202 mg, 2.0 mmol), and the mixture was allowed to react at room temperature for 30 min. The reaction was monitored by TLC until the starting material disappeared. The reactions were directly concentrated to dryness under reduced pressure, and purified by thin layer chromatography (DCM/MeOH=10:1), to provide 192 mg product as white solid, with a yield of 64.4%.

The white solid (100 mg, 0.335 mmol) was dissolved in 5 mL ethanol, to which was added hydrazine hydrate (21 mg, 0.35 mmol), and the mixture was stirred under reflux for 3 h till white solid precipitated out. The reactions were naturally cooled to room temperature, filtered, and the filtrate was concentrated to dryness under reduced pressure, to provide 35 mg white solid (SM2-5), with a yield of 62.1%.

Step 2: Synthesis of Intermediate 5-1

SM1-1 (38 mg, 0.104 mmol) was dissolved in 5 mL tetrahydrofuran, to which were sequentially added SM2-5 (35 mg, 0.208 mmol) and 2N NaOH aqueous solution (0.2 mL) under stirring, then the reaction was further stirred at room temperature for 30 min. TLC was used to monitor the reaction until the starting material disappeared. 10 mL water was added, and extracted with 10 mL ethyl acetate. The organic layer was washed twice with saturated brine, concentrated under reduced pressure to dryness, and purified by thin layer chromatography (PE/Ea=1:3), to provide 33 mg white solid (intermediate 5-1), with a yield of 65%.

Step 3: Synthesis of Compound 5

Intermediate 5-1 (33 mg, 0.067 mmol) was dissolved in 1 mL THF, then 2 N NaOH (0.3 ml, 0.6 mmol) was added, and the reaction was stirred at room temperature for 30 minutes. TLC was used to monitor the complete reaction of starting materials. 10 mL water was added, and the reaction mixture was extracted with 10 mL ethyl acetate. The organic layer was washed with saturated brine twice, dried with anhydrous sodium sulfate, and concentrated under reduced pressure to dry, to provide 23 mg target compound 5 as white solid, with a yield of 73.5%.

MS (ESI) m/z 467 (M+H)$^+$.

$^1$H NMR (400 MHz, DMSO) δ 11.48 (s, 1H), 8.90 (s, 1H), 7.26 (t, J=5.8 Hz, 1H), 7.18 (t, J=8.8 Hz, 1H), 7.11 (dd, J=6.1, 2.7 Hz, 1H), 6.76 (ddd, J=8.8, 4.0, 2.8 Hz, 1H), 6.43 (t, J=6.0 Hz, 1H), 4.84-4.74 (m, 1H), 3.60 (dd, J=13.0, 6.5 Hz, 2H), 3.45 (q, J=6.0 Hz, 2H), 3.36-3.30 (q, 2H), 3.02 (q, J=6.0 Hz, 2H).

Example 6: N-(3-bromo-4-fluorophenyl)-4-((2-(N-(2,2-difluoroethylsulfamoyl)ethyl)amino)-N'-hydroxyl-1,2,5-oxadiazol-3-formamidine(11)

Compound 11 was prepared by a synthetic method similar to Example 1 using SM1-1 and SM2-11 as starting materials.

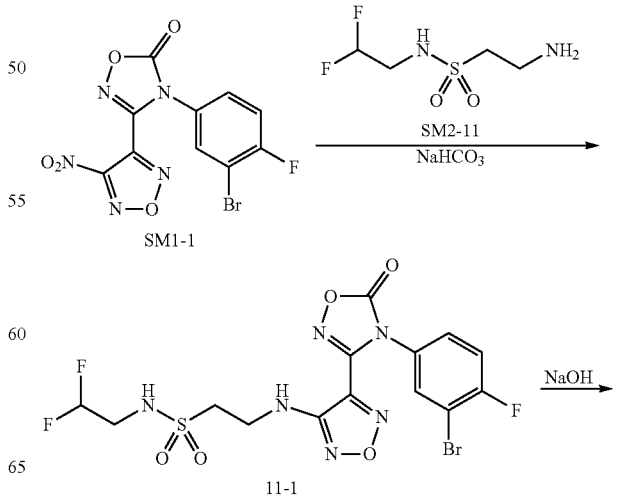

41

-continued

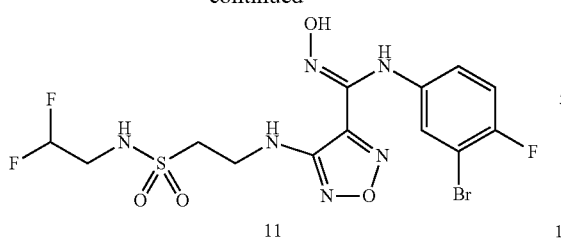

11

Step 1: Synthesis of SM2-11

2,2-difluoroethylamine (96 mg, 1.2 mmol) was dissolved in 1 mL DCM, then 2-phthalimidoethanesulfonyl chloride (273 mg, 1.0 mmol) was slowly added on ice bath, followed by addition of triethylamine (202 mg, 2.0 mmol) under stirring. The mixture was allowed to react for 1 h. TLC was used to monitor the reaction until the starting material disappeared. 10 mL water was added, then extracted with 10 mL DCM. DCM layer was washed with saturated brine, dried over anhydrous sodium sulfate, and concentrated to dryness, to obtain 260 mg product as white solid, with a yield of 82%.

The white solid product (100 mg, 0.33 mmol) was dissolved in 5 mL ethanol, to which was added hydrazine hydrate (21 mg, 0.36 mmol), and the mixture was stirred under reflux for 3 h till white solid precipitated out. The reactions were naturally cooled to room temperature, filtered, and the filtrate was concentrated to dryness under reduced pressure, to provide 41 mg white solid (SM2-11), with a yield of 67%.

Step 2: Synthesis of Intermediate 11-1

SM1-1 (41 mg, 0.11 mmol) was dissolved in 5 mL tetrahydrofuran, to which were sequentially added SM2-11 (41 mg, 0.22 mmol) and 2N NaOH aqueous solution (1.0 mL) under stirring, then the reaction was further stirred at room temperature for 2 h. TLC was used to monitor the reaction until the starting material disappeared. 10 mL water was added, and extracted with 10 mL ethyl acetate. The organic layer was washed twice with saturated brine, concentrated under reduced pressure to dryness, and purified by thin layer chromatography (PE/Ea=1:1), to provide 18 mg white solid (intermediate 11-1), with a yield of 32%.

Step 3: Synthesis of Compound 11

Intermediate 11-1 (18 mg, 0.035 mmol) was dissolved in 1 mL THF, then 2 N NaOH (0.2 ml, 0.4 mmol) was added, and the reaction was stirred at room temperature for 30 minutes. TLC was used to monitor the complete reaction of starting materials. 10 mL water was added, and the reaction mixture was extracted with 10 mL ethyl acetate. The organic layer was washed with saturated brine twice, dried with anhydrous sodium sulfate, and concentrated under reduced pressure to dry, to provide 10 mg target compound (compound 11) as white solid, with a yield of 59%.

MS (ESI) m/z 487 [M+H]$^+$.

42

Example 7: N-(3-bromo-4-fluorophenyl)-N'-hydroxyl-4-((2-N,N-dimethylsulfamoylethyl)amino)-1,2,5-oxadiazol-3-formamidine(15)

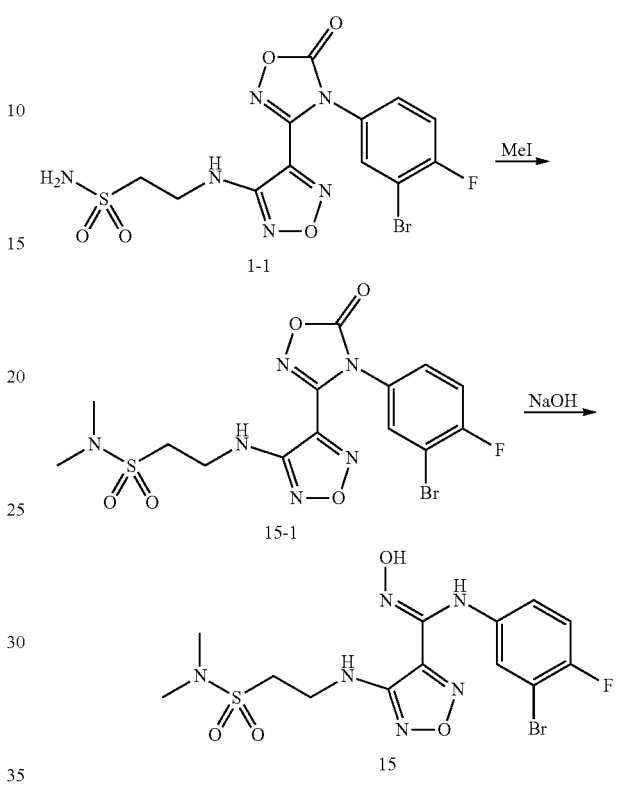

Step 1: Synthesis of Intermediate 15-1

The intermediate 1-1 (44.9 mg, 0.1 mmol) was dissolved in 3 mLDMF, to which were sequentially added CH$_3$I (42.6 mg, 0.3 mmol) under stirring and K$_2$CO$_3$ (69 mg, 0.5 mmol), then the reaction was allowed to react overnight at room temperature. TLC was used to monitor the reaction until the starting material disappeared. 5 mL water was added, and extracted with 5 mL ethyl acetate. The ethyl acetate layer was washed twice with water, then washed with saturated brine once, dried over anhydrous sodium sulfate, concentrated under reduced pressure to dryness, and purified by thin layer chromatography (PE/Ea=1:1), to provide 42 mg white solid (intermediate 15-1), with a yield of 88%.

Step 2: Synthesis of Compound 15

Intermediate 15-1 (42 mg, 0.088 mmol) was dissolved in 3 mL THF, then 2 N NaOH (0.45 ml, 0.9 mmol) was added, and the reaction was stirred at room temperature for 30 min. TLC was used to monitor the complete reaction of starting materials. 10 mL water was added, and the reaction mixture was extracted with 10 mL ethyl acetate. The organic layer was washed with saturated brine twice, dried with anhydrous sodium sulfate, and concentrated under reduced pressure to dry, to provide 35 mg target compound (compound 15) as white solid, with a yield of 88%.

MS (ESI) m/z 451 [M+H]$^+$.
$^1$H NMR (400 MHz, DMSO) δ 11.49 (s, 1H), 8.91 (s, 1H), 7.19 (t, J=8.8 Hz, 1H), 7.11 (dd, J=6.1, 2.7 Hz, 1H), 6.76

(ddd, J=8.8, 4.1, 2.8 Hz, 1H), 6.44 (t, J=6.1 Hz, 1H), 3.69-3.58 (m, 2H), 3.38-3.29 (m, 2H), 2.82-2.76 (m, 6H).

Example 8: N-(3-bromo-4-fluorophenyl)-N'-hydroxyl-4-((2-(pyrrolidin-1-ylsulfamoyl)ethyl)amino)-1,2,5-oxadiazol-3-formamidine(17)

Compound 17 was prepared by a synthetic method similar to Example 1 using SM1-1 and SM2-17 as starting materials.

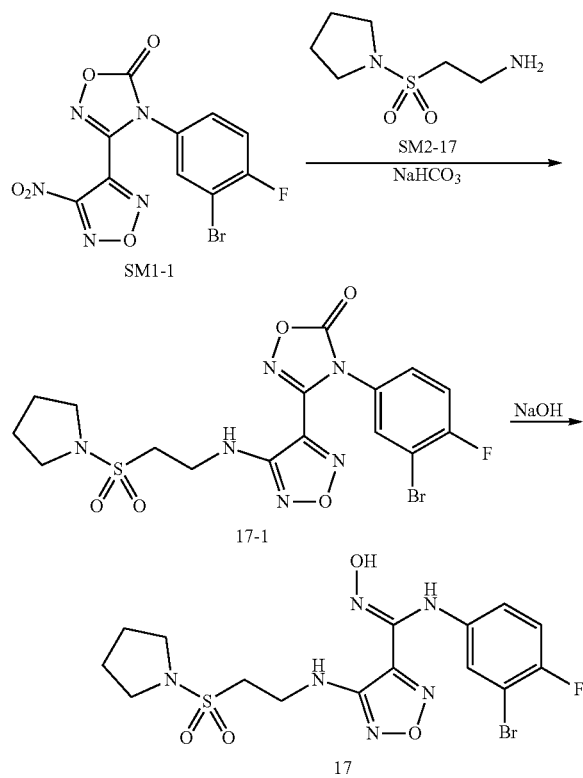

Step 1: Synthesis of SM2-17

2-Phthalimidoethanesulfonyl chloride (273 mg, 1.0 mmol) was dissolved in 3 mL DCM, to which were sequentially added tetrahydropyrrole (72 mg, 1.0 mmol) under stirring and triethylamine (202 mg, 2.0 mmol), and the mixture was allowed to react at room temperature for 30 min. The reaction was monitored by TLC until the starting material disappeared. 10 mL water was added, then extracted with 10 mL DCM. DCM layer was washed with saturated brine, dried over anhydrous sodium sulfate, and concentrated to dryness, to obtain 262 mg white solid, with a yield of 85%.

The white solid (262 mg, 0.85 mmol) was dissolved in 5 mL ethanol, to which was added hydrazine hydrate (57 mg, 0.94 mmol), and the mixture was stirred under reflux for 3 h till white solid precipitated out. The reactions were naturally cooled to room temperature, filtered, and the filtrate was concentrated to dryness under reduced pressure, to provide 71.2 mg product as white solid (SM2-17), with a yield of 47.6%.

Step 2: Synthesis of Intermediate 17-1

SM1-1 (74 mg, 0.2 mmol) was dissolved in 5 mL tetrahydrofuran, to which were sequentially added SM2-17 (71.2 mg, 0.4 mmol) and 2N NaOH aqueous solution (0.2 mL) under stirring, then the reaction was further stirred at room temperature for 30 min. TLC was used to monitor the reaction until the starting material disappeared. 10 mL water was added to the reaction solution, and extracted with 10 mL ethyl acetate. The organic layer was washed twice with saturated brine, concentrated under reduced pressure to dryness, and purified by thin layer chromatography (PE/Ea=1:1), to provide 68 mg white solid (intermediate 17-1), with a yield of 67.5%.

Step 3: Synthesis of Compound 17

Intermediate 17-1 (68 mg, 0.135 mmol) was dissolved in 1 mL THF, then 2 N NaOH (0.7 ml, 1.4 mmol) was added, and the reaction was stirred at room temperature for 30 minutes. TLC was used to monitor the complete reaction of starting materials. 10 mL water was added, and the reaction mixture was extracted with 10 mL ethyl acetate. The organic layer was washed with saturated brine twice, dried with anhydrous sodium sulfate, and concentrated under reduced pressure to dry, to provide 40 mg target compound (compound 17) as white solid, with a yield of 62%.

MS (ESI) m/z 477 [M+H]$^+$.

$^1$H NMR (400 MHz, DMSO) δ 11.50 (s, 1H), 8.91 (s, 1H), 7.19 (t, J=8.8 Hz, 1H), 7.10 (dd, J=6.1, 2.7 Hz, 1H), 6.80-6.73 (m, 1H), 6.43 (t, J=6.0 Hz, 1H), 3.63 (dd, J=13.0, 6.5 Hz, 2H), 3.37 (t, J=6.7 Hz, 2H), 3.25 (t, J=6.6 Hz, 4H), 1.87-1.82 (m, 4H).

Example 9: N-(3-bromo-4-fluorophenyl)-N'-hydroxyl-4-((2-(morpholinylsulfamoyl)ethyl)amino)-1,2,5-oxadiazol-3-formamidine(18)

Compound 18 was prepared by a synthetic method similar to Example 1 using SM1-1 and SM2-18 as starting materials.

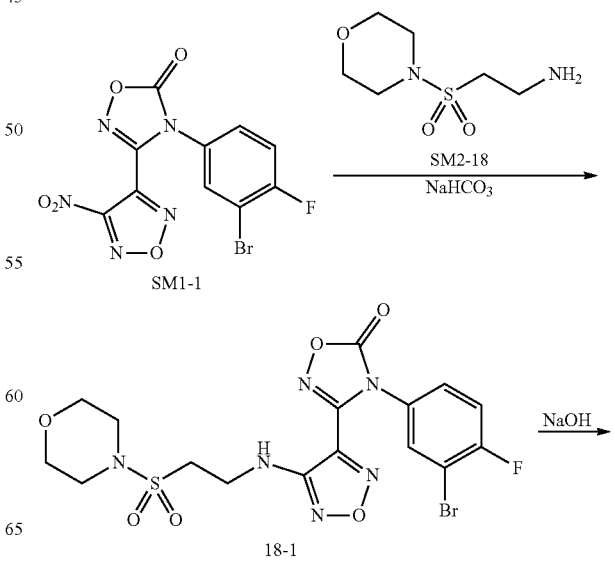

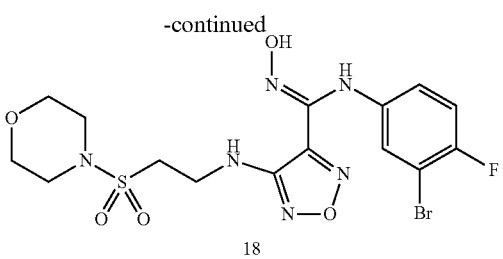

Step 1: Synthesis of SM2-18

2-Phthalimidoethanesulfonyl chloride (273 mg, 1.0 mmol) was dissolved in 3 mL DCM, to which was added morpholine (174 mg, 2.0 mmol) under stirring, and the mixture was allowed to react at room temperature for 30 min. The reaction was monitored by TLC until the starting material disappeared. 10 mL water was added, then extracted with 10 mL DCM. DCM layer was washed with saturated brine, dried over anhydrous sodium sulfate, and concentrated to dryness, to obtain 259 mg white solid, with a yield of 80%.

The white solid (259 mg, 0.8 mmol) was dissolved in 5 mL ethanol, to which was added hydrazine hydrate (53.7 mg, 0.88 mmol), and the mixture was stirred under reflux for 3 h till white solid precipitated out. The reactions were naturally cooled to room temperature, filtered, and the filtrate was concentrated to dryness under reduced pressure, to provide 85 mg product as white solid (SM2-18), with a yield of 50%.

Step 2: Synthesis of Intermediate 18-1

SM1-1 (82 mg, 0.22 mmol) was dissolved in 5 mL tetrahydrofuran, to which were sequentially added SM2-18 (85 mg, 0.44 mmol) and 2N NaOH aqueous solution (0.22 mL) under stirring, then the reaction was further stirred at room temperature for 30 min. TLC was used to monitor the reaction until the starting material almost disappeared. 10 mL water was added, and extracted with 10 mL ethyl acetate. The organic layer was washed twice with saturated brine, concentrated under reduced pressure to dryness, and purified by thin layer chromatography (PE/Ea=1:1), to provide 65 mg white solid (intermediate 18-1), with a yield of 57%.

Step 3: Synthesis of Compound 18

Intermediate 18-1 (65 mg, 0.125 mmol) was dissolved in 5 mL THF, then 2 N NaOH (0.6 ml, 1.2 mmol) was added, and the reaction was stirred at room temperature for 30 minutes. TLC was used to monitor the complete reaction of starting materials. 10 mL water was added, and the reaction mixture was extracted with 10 mL ethyl acetate. The organic layer was washed with saturated brine twice, dried with anhydrous sodium sulfate, and concentrated under reduced pressure to dry, to provide 35 mg target compound (compound 18) as white solid, with a yield of 56%.

MS (ESI) m/z 493 [M+H]$^+$ $^1$H NMR (400 MHz, DMSO-d$_6$) δ 11.50 (s, 1H), 8.92 (s, 1H), 7.19 (t, J=8.8 Hz, 1H), 7.11 (dd, J=6.0, 2.7 Hz, 1H), 6.80-6.73 (m, 1H), 6.45 (t, J=6.0 Hz, 1H), 3.65 (dd, J=10.7, 5.7 Hz, 6H), 3.38 (t, J=6.7 Hz, 2H), 3.20-3.13 (m, 4H).

Example 10: N-(3-bromo-4-fluorophenyl)-N'-hydroxyl-4-((2-sulfamoylpropyl)amino)-1,2,5-oxadiazol-3-formamidine(21)

Compound 21 was prepared by a synthetic method similar to Example 1 using SM1-1 and SM2-21 as starting materials.

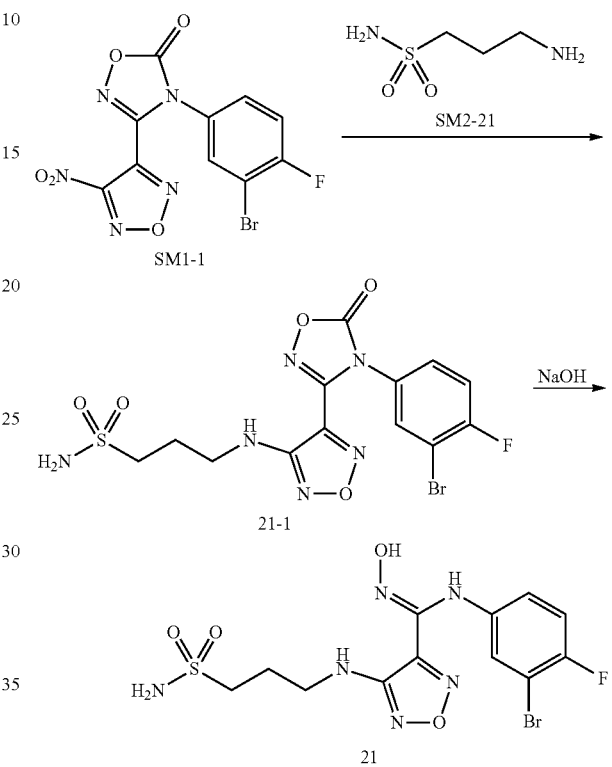

Step 1: Synthesis of Intermediate 21-1

Starting material SM1-1 (0.4 mmol, 149 mg) and compound SM2-21 (0.6 mmol, it can be prepared according to the document US20080146642) were dissolved in 4 mL THF, to which was added saturated sodium bicarbonate solution (1 ml), and the mixture was allowed to react overnight at room temperature. The reaction solution was extracted with ethyl acetate, and then the organic phase was washed successively with 0.5N hydrochloric acid and saturated brine. The organic layer was separated and concentrated under reduced pressure, and the crude product was purified by thin-layer chromatography to obtain off-white solid (intermediate 21-1) (60 mg, yield 32%).

Step 2: Synthesis of Compound 21

Intermediate 21-1 (60 mg, 0.13 mmol) was dissolved in 4 mL THF, then 2 N NaOH (1 ml) was added, and the reaction was stirred at room temperature for 0.5 h. The reaction solution was extracted with ethyl acetate. The organic layer was sequentially washed with water and saturated brine. The organic layer was separated and dried by rotatory evaporator under reduced pressure, to provide compound 21 as white solid (45 mg, yield 80%).

MS m/z(ESI): 437.0 [M+H]$^+$ $^1$H NMR (400 MHz, DMSO-d$_6$) δ 11.49 (s, 1H), 8.91 (s, 1H), 7.19 (t, J=8.8 Hz, 1H), 7.12 (dd, J=6.1, 2.7 Hz, 1H), 6.81 (d, J=8.7 Hz, 2H), 6.79-6.74 (m, 1H), 6.31 (t, J=5.9 Hz, 1H), 3.40-3.34 (m, 2H), 3.02 (dd, J=9.0, 6.5 Hz, 2H), 2.01 (dd, J=13.0, 5.3 Hz, 2H).

Example 11: N-(3-bromo-4-fluorophenyl)-N'-hydroxyl-4-((3-(N-methylsulfamoyl)propyl)amino)-1,2,5-oxadiazol-3-formamidine(22)

Compound 22 was prepared by a synthetic method similar to Example 1 using SM1-1 and SM2-22 as starting materials. SM2-22 was prepared according to the literature method (Biooranic & Medicinal Chemistry 2001, 9, 2709; Journal of Medicinal Chemistry, 2010, 53, 2390).

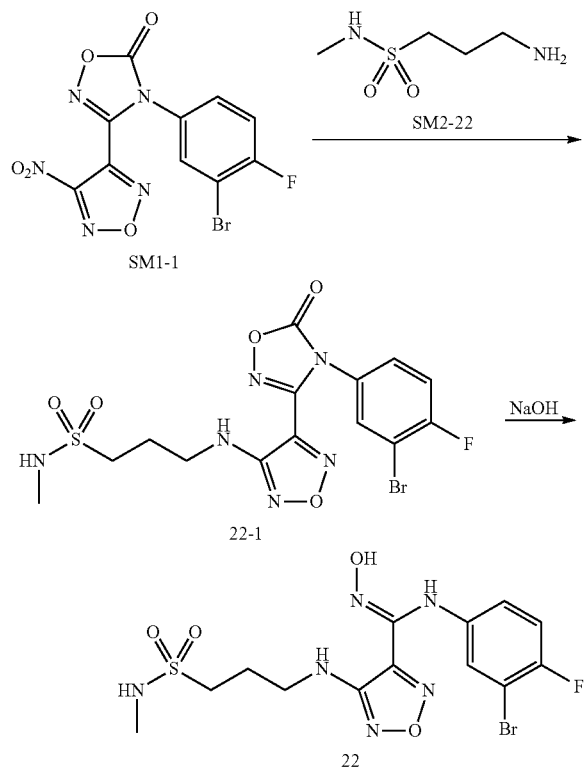

Step 1: Synthesis of Intermediate 22-1

Starting material SM1-1 (0.4 mmol, 149 mg) and compound SM2-22 (0.6 mmol) were dissolved in 4 mL THF, to which was added saturated sodium bicarbonate solution (1 ml), and the mixture was allowed to react overnight at room temperature. The reaction solution was extracted with ethyl acetate, and then the organic phase was washed successively with 0.5 N hydrochloric acid and saturated brine. The organic layer was concentrated and purified by prep-TLC to obtain off-white solid (intermediate 22-1) (70 mg, yield 37%).

Step 2: Synthesis of Compound 22

Intermediate 22-1 (70 mg, 0.15 mmol) was dissolved in 4 mL THF, then 2 N NaOH (1 ml) was added, and the reaction was stirred at room temperature for 0.5 h. The reaction solution was extracted with ethyl acetate. The organic phase was sequentially washed with water and saturated brine. The organic layer was separated and dried by rotatory evaporator under reduced pressure, to provide compound 22 as off-white solid (60 mg, yield 90%).

MS m/z(ESI): 451.0 [M+H]$^+$ $^1$H NMR (400 MHz, CD$_3$OD) δ 7.03 (dd, J=6.0, 2.7 Hz, 1H), 6.95 (t, J=8.7 Hz, 1H), 6.74 (ddd, J=8.8, 4.1, 2.7 Hz, 1H), 3.35 (t, J=6.7 Hz, 2H), 3.04-2.96 (m, 2H), 2.59 (s, 3H), 1.99 (dt, J=9.6, 6.8 Hz, 2H).

Example 12: N-(3-bromo-4-fluorophenyl)-N'-hydroxyl-4-((3-(N-ethylsulfamoyl)propyl)amino)-1,2,5-oxadiazol-3-formamidine(23)

Compound 23 was prepared by a synthetic method similar to Example 1 using SM1-1 and SM2-23 as starting materials. SM2-23 was prepared according to the literature method (Biooranic& Medicinal Chemistry 2001, 9, 2709).

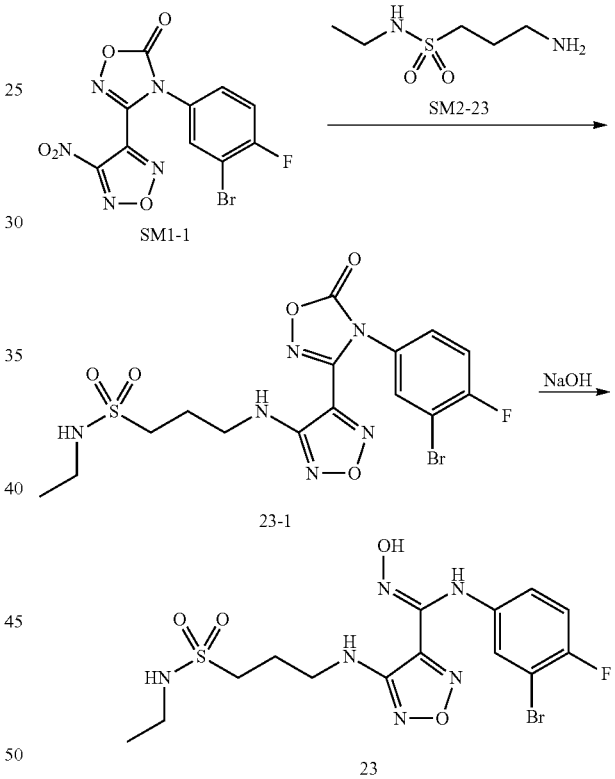

Step 1: Synthesis of Intermediate 23-1

Starting material SM1-1 (0.2 mmol, 74 mg) and compound SM2-23 (0.3 mmol) were dissolved in 4 mL THF, to which was added saturated sodium bicarbonate solution (1 ml), and the mixture was allowed to react overnight at room temperature. The reaction solution was extracted with ethyl acetate, and then the organic phase was washed successively with water and saturated brine. The organic layer was separated and rotatory evaporated to dry under reduced pressure. The crude product was purified by thin-layer chromatography to obtain off-white solid (intermediate 23-1) (15 mg, yield 15%).

Step 2: Synthesis of Compound 23

Intermediate 23-1 (15 mg) was dissolved in 4 mL THF, then 2 N NaOH (1 ml) was added, and the reaction was stirred at room temperature for 0.5 h. The reaction solution was extracted with ethyl acetate. The organic phase was sequentially washed with water and saturated brine. The organic layer was separated and dried by rotary evaporator under reduced pressure, to provide compound 23 as off-white solid (12 mg, yield 86%).

MS m/z(ESI): 465.0 [M+H]$^+$.

$^1$H NMR (400 MHz, CD$_3$OD) δ 7.03 (dd, J=6.0, 2.7 Hz, 1H), 6.95 (t, J=8.7 Hz, 1H), 6.74 (ddd, J=8.8, 4.1, 2.7 Hz, 1H), 3.34 (t, J=6.7 Hz, 2H), 2.98 (ddd, J=14.4, 9.5, 6.3 Hz, 4H), 2.05-1.95 (m, 2H), 1.06 (t, J=7.2 Hz, 3H).

Example 13: N-(3-bromo-4-fluorophenyl)-N'-hydroxyl-4-((3-(N-isopropylsulfamoyl)propyl)amino)-1,2,5-oxadiazol-3-formamidine(24)

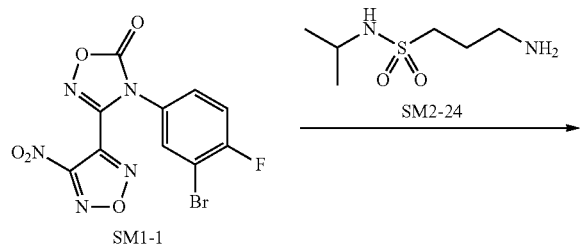

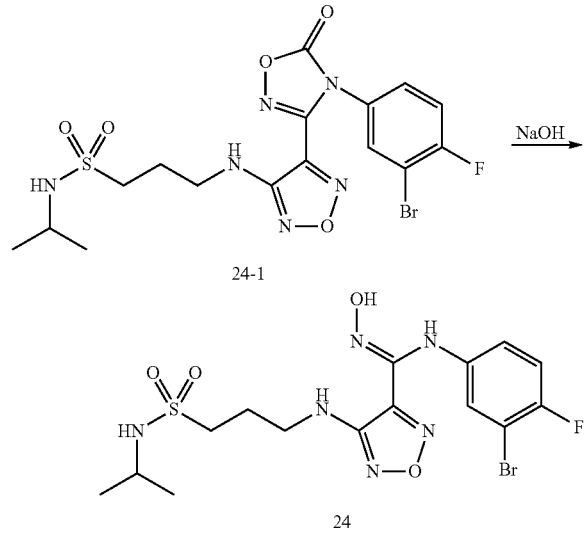

Compound 24 was prepared by a synthetic method similar to Example 1 using SM1-1 and SM2-24 as starting materials. SM2-24 was prepared by the method similar to that of compound SM2-23.

Step 1: Synthesis of Intermediate 24-1

Starting material SM1-1 (0.4 mmol, 149 mg) and compound SM2-24 (0.7 mmol) were dissolved in 4 mL THF, to which was added saturated sodium bicarbonate solution (1 ml), and the mixture was allowed to react overnight at room temperature. The reaction solution was extracted with ethyl acetate, and then the organic phase was washed successively with water and saturated brine. The organic layer was separated and rotatory evaporated to dry under reduced pressure. The crude product was purified by thin-layer chromatography to obtain yellowy solid (intermediate 24-1) (135 mg, yield 67%).

Step 2: Synthesis of Compound 24

Intermediate 24-1 (135 mg, 0.27 mmol) was dissolved in 4 mL THF, then 2 N NaOH (1 ml) was added, and the reaction was stirred at room temperature for 0.5 h. The reaction solution was extracted with ethyl acetate. The organic phase was sequentially washed with water and saturated brine. The organic layer was separated and dried by rotatory evaporator under reduced pressure, to provide yellowy solid (compound 23) (107 mg, yield 83%).

MS m/z(ESI): 479.0 [M+H]$^+$ $^1$H NMR (400 MHz, MeOD) δ 7.14 (dd, J=6.0, 2.7 Hz, 1H), 7.07 (t, J=8.7 Hz, 1H), 6.86 (ddd, J=8.8, 4.1, 2.7 Hz, 1H), 3.53 (s, 1H), 3.46 (t, J=6.7 Hz, 2H), 3.14-3.06 (m, 2H), 2.13 (dd, J=8.7, 6.6 Hz, 2H), 1.20 (d, J=6.6 Hz, 6H).

Example 14: N-(3-bromo-4-fluorophenyl)-N'-hydroxyl-4-((3-(N-cyclopropylsulfamoyl)propyl)amino)-1,2, 5-oxadiazol-3-formamidine(25)

Compound 25 was prepared by synthetic method B using SM1-1 and 3-aminopropanesulfonic acid as starting materials.

Method B:

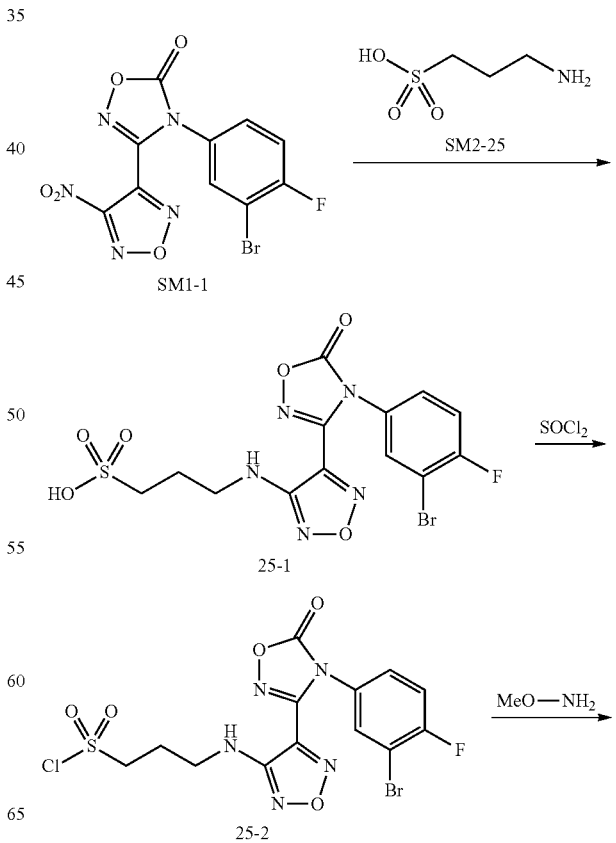

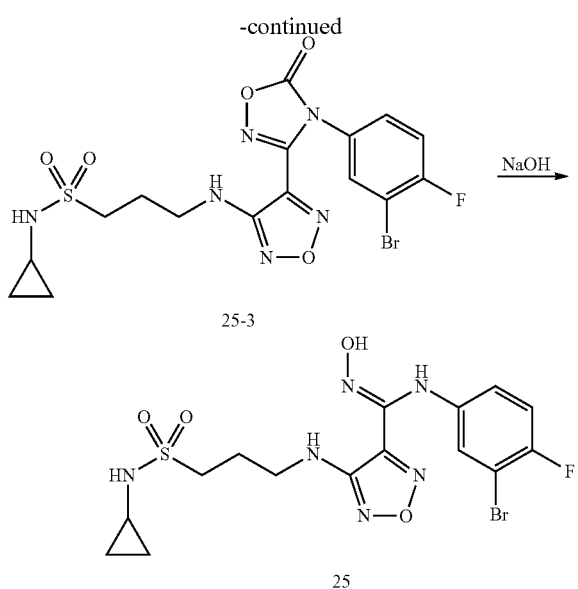

Step 1: Synthesis of Intermediate 25-1

Starting material SM1-1 (2 mmol, 744 mg) and 3-aminopropanesulfonic acid (4 mmol, 556 mg, commercially available) were dissolved in 20 ml THF, and 4 ml saturated sodium bicarbonate solution was added. After reacting overnight at room temperature, the reaction solution was neutralized with 0.5N hydrochloric acid and extracted with ethyl acetate. The organic phase was washed successively with 0.5N hydrochloric acid, water, and saturated brine. After the organic layer was separated, it was concentrated under reduced pressure and slurried with DCM to obtain the crude product intermediate 25-1 (490 mg, yield 53%).

Step 2: Synthesis of Intermediate 25-2

The crude product intermediate 25-1 (0.1 mmol, 50 mg) was placed in a 50 ml three-necked flask, and the flask was purged with nitrogen, to which were successively added 1 ml dichloromethane and 1 drop DMF, thenthionyl chloride (0.1 ml) was dropwise added under stirring. The mixture was allowed to react at 40° C. for 3 h, monitored by TLC, and directly rotatory evaporated to obtain the crude product intermediate 25-2 for use.

Step 3: Synthesis of Intermediate 25-3

Into a 25 ml round bottom flask, were add 1 ml DCM and cyclopropylamine (1 mmol, 57 mg). The solution of intermediate 25-2 (the product of above step) in DCM (0.5 ml) was drop added under stirring at 0° C. After stirring for 3 h at room temperature, the reaction was extracted with ethyl acetate, and the organic phase was sequentially washed with 0.5N hydrochloric acid and saturated brine. The organic layer was rotatory evaporated and slurried with DCM, to obtain 25 mg pale yellow solid (intermediate 25-3), with a yield of 50%.

Step 4: Synthesis of Compound 25

The product of the previous step intermediate 25-3 was dissolved in 2 ml THF, to which was added 2N NaOH (0.5 ml), and the mixture was stirred at room temperature for 0.25 h. After that, the reaction solution was extracted with ethyl acetate, and the organic phase was washed with water, and then with saturated brine. The organic layer was separated and then rotatory evaporated under reduced pressure, to obtain compound 25 (23 mg, yield 96%) as a pale yellow solid.

MS m/z(ESI): 477.0 [M+H]$^+$.

$^1$H NMR (400 MHz, MeOD) δ 7.03 (dd, J=6.0, 2.7 Hz, 1H), 6.95 (t, J=8.7 Hz, 1H), 6.75 (ddd, J=8.8, 4.1, 2.7 Hz, 1H), 3.36 (t, J=6.7 Hz, 2H), 3.13-3.00 (m, 2H), 2.39 (dq, J=6.8, 3.6 Hz, 1H), 2.08-1.94 (m, 2H), 0.60-0.52 (m, 2H), 0.52-0.46 (m, 2H).

Example 15: N-(3-bromo-4-fluorophenyl)-N'-hydroxyl-4-((3-(N-cyclopentylsulfamoyl)propyl)amino)-1,2, 5-oxadiazol-3-formamidine(27)

Compound 27 was prepared by a synthetic method similar to Example 1 using SM1-1 and SM2-27 as starting materials. SM2-27 was prepared by the method similar to that of compound SM2-23.

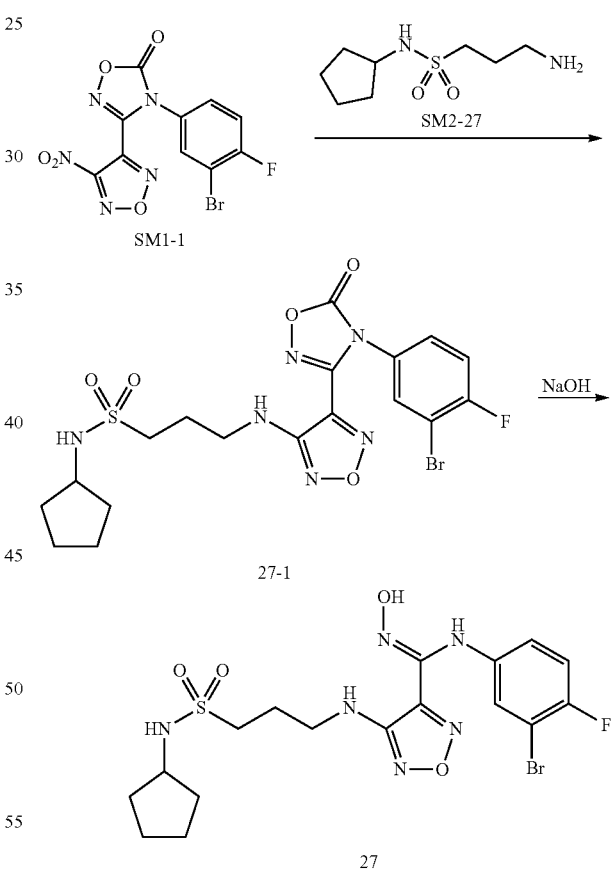

Step 1: Synthesis of Intermediate 27-1

Starting material SM1-1 (0.4 mmol, 149 mg) and compound SM227 (067 mmol) were dissolved in 4 mL THF, to which was added saturated sodium bicarbonate solution (1 ml), and the mixture was allowed to react overnight at room temperature. The reaction solution was extracted with ethyl acetate, and then the organic phase was washed successively with water and saturated brine. The organic layer was separated and rotatory evaporated to dry under reduced pressure. The crude product was purified by thin-layer chromatography to obtain intermediate 27-1 as yellowy solid (125 mg, yield 59%).

Step 2: Synthesis of Compound 27

Intermediate 27-1 (125 mg, 0.24 mmol) was dissolved in 4 mL THF, then 2N NaOH (1 ml) was added, and the reaction was stirred at room temperature for 0.5 h. The reaction solution was extracted with ethyl acetate. The organic phase was sequentially washed with water and saturated brine. The organic layer was separated and dried by rotatory evaporator under reduced pressure, to provide compound 27 as yellowy solid (105 mg, yield 89%).

MS m/z(ESI): 505.0 [M+H]$^+$ $^1$H NMR (400 MHz, CD$_3$OD) δ 7.03 (dd, J=6.0, 2.7 Hz, 1H), 6.95 (t, J=8.7 Hz, 1H), 6.77-6.72 (m, 1H), 3.62-3.51 (m, 1H), 3.35 (t, J=6.7 Hz, 2H), 3.08-2.91 (m, 2H), 2.00 (dd, J=9.8, 5.4 Hz, 2H), 1.82 (dd, J=12.2, 5.4 Hz, 2H), 1.59 (dd, J=9.3, 2.9 Hz, 2H), 1.45 (td, J=7.5, 3.9 Hz, 2H), 1.42-1.32 (m, 2H).

Example 16: N-(3-bromo-4-fluorophenyl)-N'-hydroxyl-4-((3-(N-(2-hydroxyethyl)sulfamoyl)propyl)amino)-1,2,5-oxadiazol-3-formamidine(29)

Compound 29 was prepared by a synthetic method similar to Example 1 using SM1-1 and SM2-29 as starting materials. SM2-29 was prepared by the method similar to that of compound SM2-23.

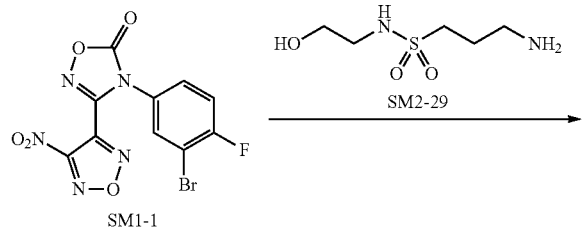

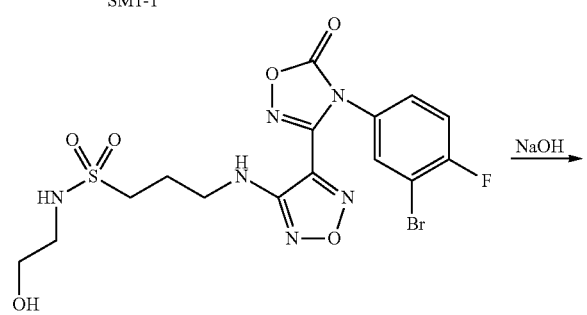

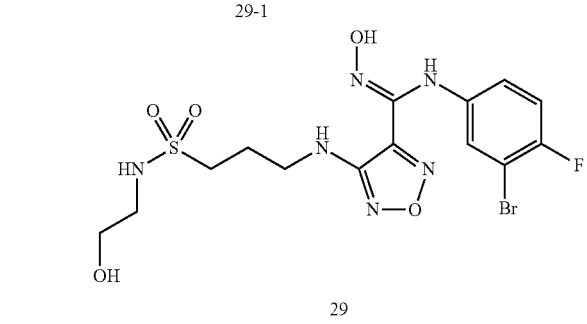

Step 1: Synthesis of Intermediate 29-1

SM1-1 (29.7 mg, 0.08 mmol) was dissolved in 5 mL THF, to which were successively added intermediate SM2-29 (29 mg, 0.16 mmol) and 2N NaOH aqueous solution (0.2 mL) under stirring, then the reaction was further stirred at room temperature for 30 min. TLC was used to monitor the reaction until the starting material almost disappeared. 10 mL water was added, and extracted with 10 mL ethyl acetate. The organic layer was washed twice with saturated brine, concentrated under reduced pressure to dryness, and purified by thin layer chromatography (PE/EtOAc=1:3), to provide 30 mg intermediate 29-1 as white solid, with a yield of 75%.

Step 2: Synthesis of Compound 29

Intermediate 29-1 (30 mg, 0.06 mmol) was dissolved in 2 mL THF, then 2 N NaOH (0.06 ml, 0.12 mmol) was added, and the reaction was stirred at room temperature for 30 minutes. TLC was used to monitor the complete reaction of starting materials. 10 mL water was added, and the reaction mixture was extracted with 10 mL ethyl acetate. The organic layer was washed with saturated brine twice, dried with anhydrous sodium sulfate, and concentrated under reduced pressure to dry, to provide 23 mg target compound 29 as white solid, with a yield of 80.8%.

MS (ESI) m/z 481 [M+H]$^+$.

$^1$H NMR (400 MHz, DMSO) δ 11.46 (s, 1H), 8.90 (s, 1H), 7.18 (t, J=8.8 Hz, 1H), 7.12 (dd, J=6.1, 2.7 Hz, 1H), 7.07 (t, J=5.9 Hz, 1H), 6.77 (ddd, J=8.9, 4.1, 2.8 Hz, 1H), 6.29 (t, J=5.9 Hz, 1H), 4.74 (t, J=5.5 Hz, 1H), 3.43 (dd, J=11.7, 6.0 Hz, 2H), 3.37-3.27 (m, 6H), 3.11-3.03 (m, 2H), 2.98 (q, J=6.1 Hz, 2H), 2.00-1.89 (m, 3H).

Example 17: N-(3-bromo-4-fluorophenyl)-N'-hydroxyl-4-((3-(N-ethylsulfamoyl)propyl)amino)-1,2,5-oxadiazol-3-formamidine(36)

Compound 36 was prepared by a synthetic method similar to Example 1 using SM1-1 and SM2-36 as starting materials. SM2-36 was prepared by the method similar to that of compound SM2-23.

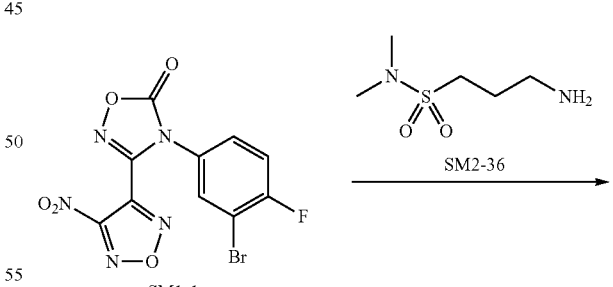

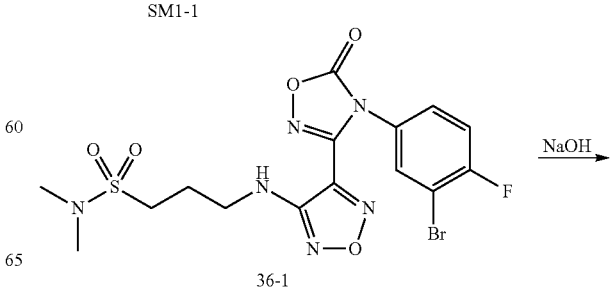

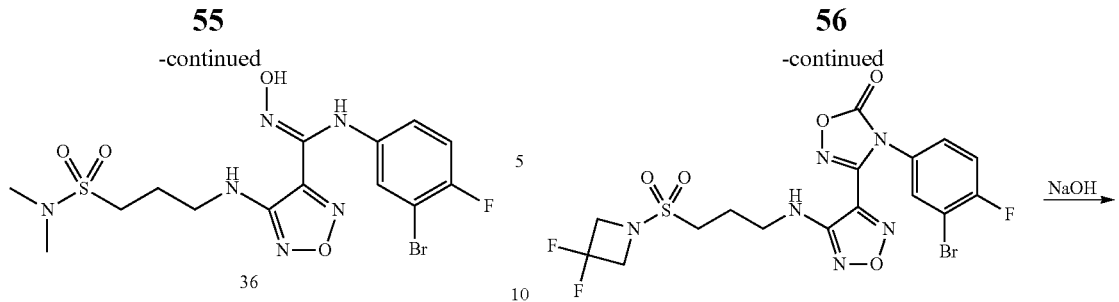

36

Step 1: Synthesis of Intermediate 36-1

Starting material SM1-1 (0.4 mmol, 149 mg) and compound SM2-36 (0.56 mmol) were dissolved in 4 mL THF, to which was added saturated sodium bicarbonate solution (1 ml), and the mixture was allowed to react overnight at room temperature. The reaction solution was extracted with ethyl acetate, and then the organic phase was washed successively with water and saturated brine. The organic layer was separated and rotatory evaporated to dry under reduced pressure. The crude product was purified by thin-layer chromatography to obtain intermediate 36-1 as yellowy solid (100 mg, yield 51%).

Step 2: Synthesis of Compound 36

Intermediate 36-1 (100 mg, 0.2 mmol) was dissolved in 4 mL THF, then 2 N NaOH (1 ml) was added, and the reaction was stirred at room temperature for 0.5 h. The reaction solution was extracted with ethyl acetate. The organic phase was sequentially washed with water and saturated brine. The organic layer was separated and dried by rotatory evaporator under reduced pressure, to provide compound 36 as yellowy solid (90 mg, yield 96%).

MS m/z(ESI): 465.0 [M+H]$^+$

1H NMR (400 MHz, MeOD) δ 7.03 (dd, J=6.0, 2.7 Hz, 1H), 6.95 (t, J=8.7 Hz, 1H), 6.74 (ddd, J=8.8, 4.1, 2.7 Hz, 1H), 3.34 (t, J=6.7 Hz, 2H), 2.98 (ddd, J=14.4, 9.5, 6.3 Hz, 4H), 2.05-1.95 (m, 2H), 1.06 (t, J=7.2 Hz, 3H).

Example 18: N-(3-bromo-4-fluorophenyl)-4-((3-((3, 3-difluoroacridin-1-yl)sulfamoyl)propyl)amino)-N'-hydroxyl-1,2,5-oxadiazol-3-formamidine(40)

Compound 40 was prepared by a synthetic method similar to Example 1 using SM1-1 and SM2-40 as starting materials. SM2-40 was prepared by the method similar to that of compound SM2-23.

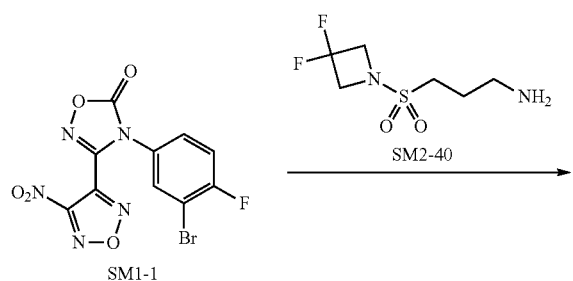

Compound 3,3-difluorotrimethyleneimine hydrochloride (216.0 mg, 1.7 mmol) and triethylamine (703.4 mg, 7.0 mmol) were added to 10 mL dichloromethane, and 3-(1,3-oxoisoindol-2-yl)propyl-1-sulfonyl chloride (400.0 mg, 1.4 mmol) was added to the reaction solution in batches. The mixture was stirred at room temperature for 2 hours. 30 mL dichloromethane was added, and the organic layer was washed twice with 1N HCl, then washed with saturated brine, dried over anhydrous sodium sulfate, rotatory evaporated, and purified by silica gel column chromatography. The white solid compound 2-(3-(3,3-difluoroazetidinyl)sulfonamide)propyl)isoindol-1,3-dione (420.0 mg, 1.2 mmol) was obtained, with a yield of 87.7%.

Compound 2-(3-(3,3-difluoroazetidinyl)sulfonamide)propyl)isoindol-1,3-dione (420.0 mg, 1.2 mmol) was dissolved in 10 mL ethanol, to which was added 0.4 mL hydrazine hydrate (80%). After stirring for 1 hour at room temperature, a large amount of white solid precipitated. The solution was suction filtered through a pad of celite, and the filter cake was washed with ethyl acetate. The filtrate was extracted with water and ethyl acetate, and the organic layer was washed 3 times with brine, dried over anhydrous sodium sulfate, and rotatory evaporated. The crude compound 3-((3, 3-difluoroazetidinyl)sulfonamide)propyl)-1-amine (249.0 mg, 1.7 mmol) SM2-40 was obtained, and without purification, it was directly used to the next step of reaction. Yield: 100%.

Compound 4-(3-bromo-4-fluorophenyl)-3-(4-nitro-1,2,5-oxazol-3-yl)-1,2,4-oxazol-5(4H)-one SM1-1 (150.0 mg, 0.4 mmol) and the crude compound 3-((3,3-difluoroazetidinyl)sulfonamide)propyl)-1-amine SM2-40 (249.0 mg, 1.7 mmol,) were added into 16 mLTHF and 3 mL 2N sodium hydroxide, and the mixture was stirred at room temperature for 3 h. Ethyl acetate and water was added, extracted, dried, rotatory evaporated, and purified by silica gel column chromatography. Compound N-(3-bromo-4-fluorophenyl)-4-((3-(3,3-difluoroazetidinyl)sulfonyl)propyl)amino)-N'-hydroxyl-1,2,5-oxadiazol-3-amidine 40 (95.0 mg, 0.18 mmol) was obtained. Yield: 45.9%.

MS (ESI) m/z 513 [M+H]$^+$.

$^1$H NMR (400 MHz, DMSO-d$_6$) δ 11.42 (s, 1H), 8.90 (s, 1H), 7.18 (t, J=8.8 Hz, 1H), 7.12 (dd, J=6.1, 2.7 Hz, 1H), 6.77 (ddd, J=8.8, 4.0, 2.9 Hz, 1H), 6.33 (t, J=5.9 Hz, 1H), 4.45-4.34 (m, 4H), 3.39-3.29 (m, 6H), 2.07-1.90 (m, 2H).

Example 19: N-(3-bromo-4-fluorophenyl)-N'-hydroxyl-4-((3-(pyrrolidin-1-ylsulfamoyl)propyl)amino)-1,2,5-oxadiazol-3-formamidine(41)

Compound 41 was prepared by a synthetic method similar to Example 1 using SM1-1 and SM2-41 as starting materials. SM2-41 was prepared by the method similar to that of compound SM2-23.

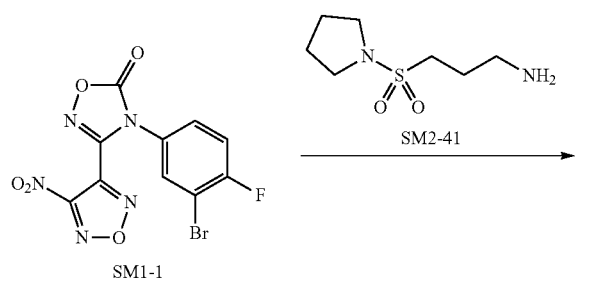

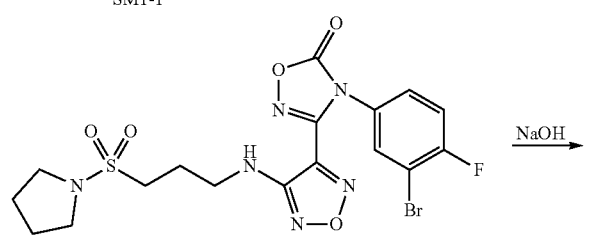

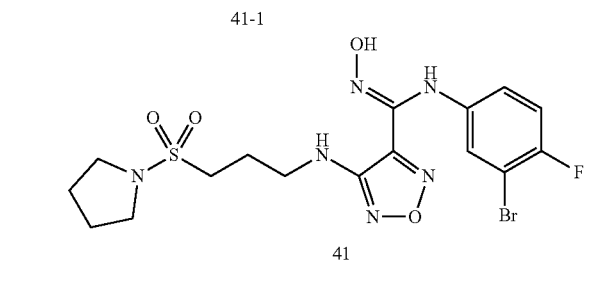

Step 1: Synthesis of Intermediate 41-1

SM1-1 (37 mg, 0.1 mmol) was dissolved in 5 mL THF, to which were successively added intermediate SM2-41 (38.4 mg, 0.2 mmol) and 2N NaOH aqueous solution (0.1 mL) under stirring, then the reaction was further stirred at room temperature for 30 min. TLC was used to monitor the reaction until the starting material almost disappeared. 10 mL water was added, and extracted with 10 mL ethyl acetate. The organic layer was washed twice with saturated brine, concentrated under reduced pressure to dryness, and purified by thin layer chromatography (PE/EtOAc=1:1), to provide 35 mg intermediate 41-1 as white solid, with a yield of 67%.

Step 2: Synthesis of Compound 41

Intermediate 41-1 (35 mg, 0.067 mmol) was dissolved in 2 mL THF, then 2 N NaOH (0.3 ml, 0.6 mmol) was added, and the reaction was stirred at room temperature for 30 minutes. TLC was used to monitor the complete reaction of starting materials. 10 mL water was added, and the reaction mixture was extracted with 10 mL ethyl acetate. The organic layer was washed with saturated brine twice, dried over anhydrous sodium sulfate, and concentrated under reduced pressure to dry, to provide 18 mg target compound 41 as white solid, with a yield of 54%.

MS (ESI) m/z 491 [M+H]$^+$

1H NMR (400 MHz, DMSO) δ 11.44 (s, 1H), 8.90 (s, 1H), 7.18 (t, J=8.8 Hz, 1H), 7.12 (dd, J=6.1, 2.7 Hz, 1H), 6.80-6.73 (m, 1H), 6.32 (t, J=5.9 Hz, 1H), 3.60 (s, 1H), 3.30 (d, J=6.7 Hz, 1H), 3.23 (t, J=6.7 Hz, 4H), 3.15-3.08 (m, 2H), 2.01-1.92 (m, 3H), 1.86-1.80 (m, 4H).

Example 20: N-(3-bromo-4-fluorophenyl)-N'-hydroxyl-4-((3-(N-methoxylsulfamoyl)propyl)amino)-1,2,5-oxadiazol-3-formamidine(45)

Compound 45 was prepared by synthetic method B using SM1-1 and SM2-45 as starting materials.

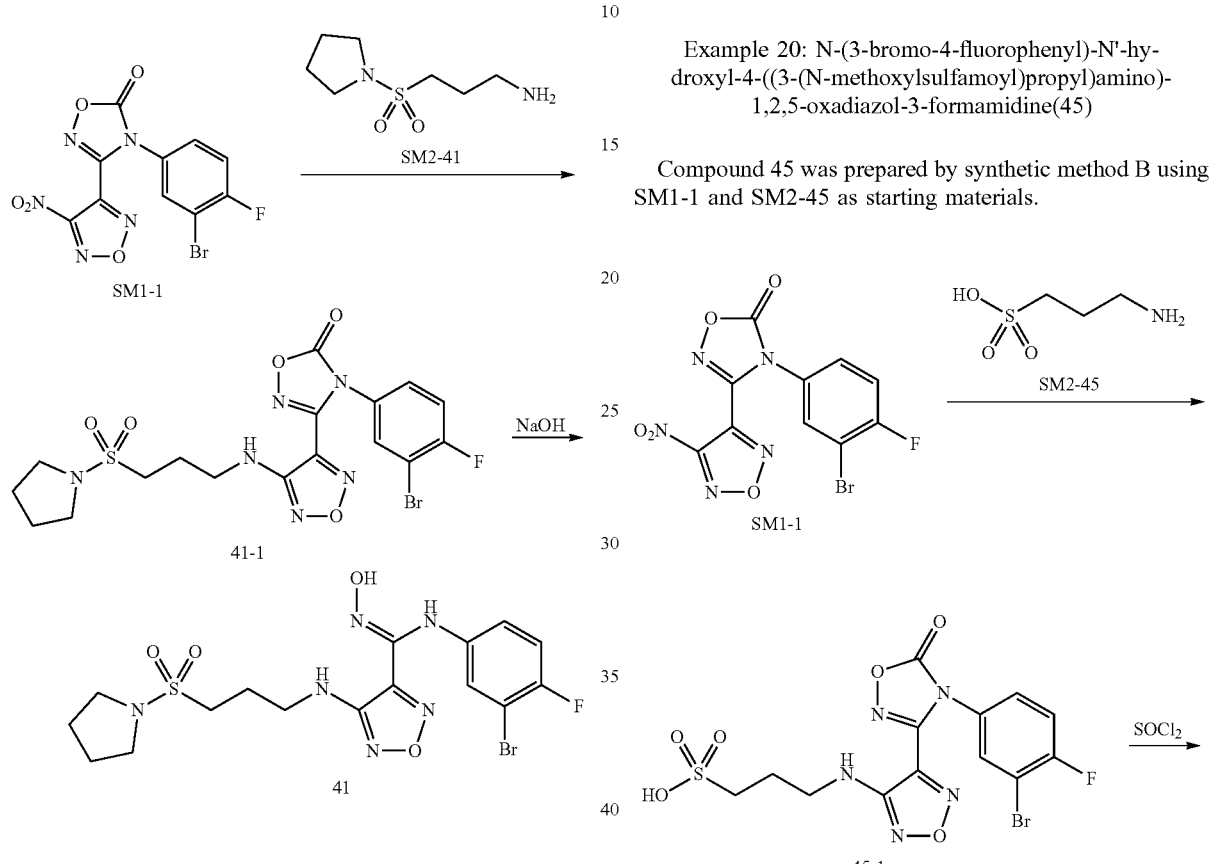

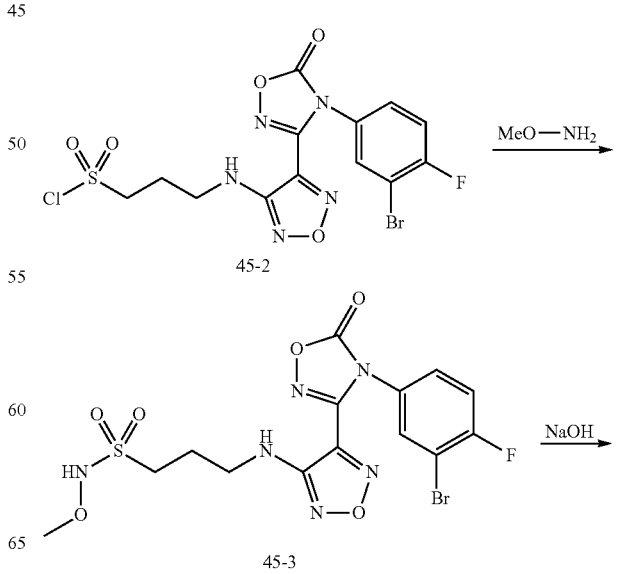

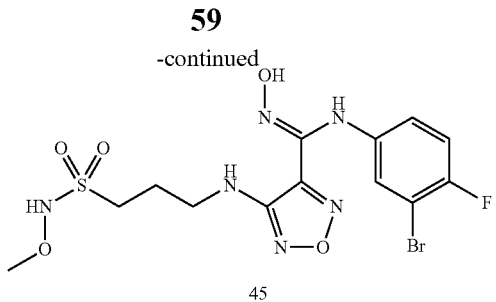

45

Step 1: Synthesis of Intermediate 45-1

Starting material SM1-1 (2 mmol, 744 mg) and 3-aminopropanesulfonic acid (4 mmol, 556 mg) were dissolved in 20 ml THF, and 4 ml saturated sodium bicarbonate solution was added. After reacting overnight at room temperature, the reaction solution was neutralized with 0.5 N hydrochloric acid and extracted with ethyl acetate. The organic phase was washed successively with 0.5 N hydrochloric acid, water, and saturated brine. After the organic layer was separated, it was concentrated under reduced pressure and slurried with DCM to obtain the crude product intermediate 45-1 (490 mg, yield 53%).

Step 2: Synthesis of Intermediate 45-2

The crude product intermediate 45-1 (0.1 mmol, 50 mg) was placed in a 50 ml three-necked flask, and the flask was purged with nitrogen, to which were successively added 1 ml dichloromethane and 1 drop DMF, then thionyl chloride (0.1 ml) was drop added under stirring. The mixture was allowed to react at 40° C. for 3 h, monitored by TLC, and directly rotary evaporated to obtain the crude product intermediate 45-2 for use.

Step 3: Synthesis of Intermediate 45-3

Into a 25 ml round bottom flask, were add 1 ml THF/0.1 ml water, methoxamine hydrochloride (0.3 mmol, 25 mg), and potassium carbonate (0.3 mmol, 42 mg). The solution of intermediate 45-2 (the product of above step) in DCM (0.5 ml) was drop added under stirring. After stirring for 2 h at room temperature, the reaction was extracted with ethyl acetate, and the organic phase was sequentially washed with water and saturated brine. The organic layer was separated and rotatory evaporated, to obtain intermediate 45-3, that was directly used to the next step of reaction.

Step 4: Synthesis of Compound 45

The product of the previous step intermediate 45-3 was dissolved in 4 ml THF, to which was added 2N NaOH (1 ml), and the mixture was stirred at room temperature for 0.25 h. After that, the reaction solution was extracted with ethyl acetate, and the organic phase was washed with water, and then with saturated brine. The organic layer was separated and then rotatory evaporated under reduced pressure, to obtain compound 45 (10 mg, yield 20%) as white solid.

MS m/z (ESI): 467.0 [M+H]$^+$.

$^1$H NMR (400 MHz, CD$_3$OD) δ 7.03 (dd, J=6.0, 2.7 Hz, 1H), 6.95 (t, J=8.7 Hz, 1H), 6.74 (ddd, J=8.8, 4.0, 2.8 Hz, 1H), 3.64 (s, 3H), 3.35 (t, J=6.7 Hz, 2H), 3.15 (dd, J=8.6, 6.8 Hz, 2H), 2.10-1.95 (m, 2H).

Example 21: N-(3-bromo-4-fluorophenyl)-N'-hydroxyl-4-((3-(N-hydroxylsulfamoyl)propyl)amino)-1,2,5-oxadiazol-3-formamidine(46)

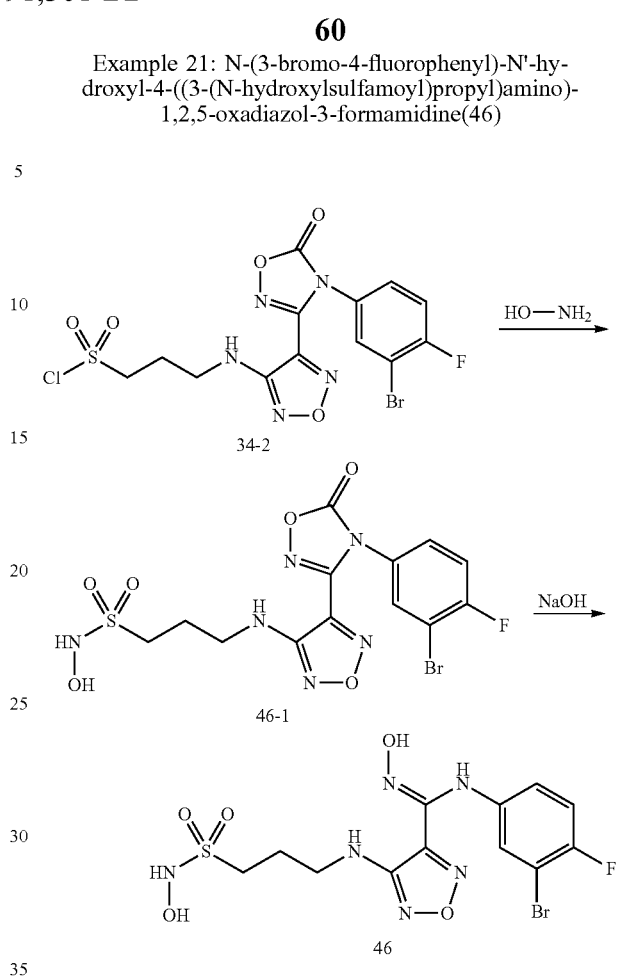

Compound 46 was prepared by synthetic method B using 46-1 and hydroxylamine as starting materials.

Into a 25 ml round bottom flask, were add 2 ml THF/0.2 ml water, hydroxylamine hydrochloride (2 mmol, 139 mg), and potassium carbonate (2 mmol, 139 mg). Under stirring, 1 ml solution of 34-2 in DCM was added dropwise, and the mixture was stirred at room temperature for 3 h. Ethyl acetate was added for extraction, and the organic phase was washed with 0.5N hydrochloric acid, and then with saturated brine. The organic layer was rotatory evaporated under reduced pressure and used directly in the next reaction.

Products from the previous step was dissolved in 2 mL THF, then 1 N NaOH (0.5 ml) was added, and the reaction was stirred at room temperature for 0.25 h. The reaction solution was extracted with ethyl acetate. The organic phase was sequentially washed with 0.5N hydrochloric acid, and then with saturated brine. The organic layer was separated and dried by rotatory evaporator under reduced pressure. The crude product was purified by TLC to provide compound 46 as off-white solid (10 mg, yield 10%).

MS m/z(ESI): 453.0 [M+H]$^+$

1H NMR (400 MHz, MeOD) δ 7.03 (dd, J=5.9, 2.7 Hz, 1H), 6.95 (t, J=8.7 Hz, 1H), 6.74 (ddd, J=8.8, 4.0, 2.8 Hz, 1H), 3.37 (t, J=6.7 Hz, 2H), 3.19-3.13 (m, 2H), 2.05 (dd, J=14.8, 7.1 Hz, 2H).

Example 22: N-(3-bromo-4-fluorophenyl)-N'-hydroxyl-4-((4-sulfamoylbutyl)amino)-1,2,5-oxadiazol-3-formamidine(98)

Compound 98 was prepared by a synthetic method similar to Example 1 using SM1-1 and SM2-98 as starting materials.

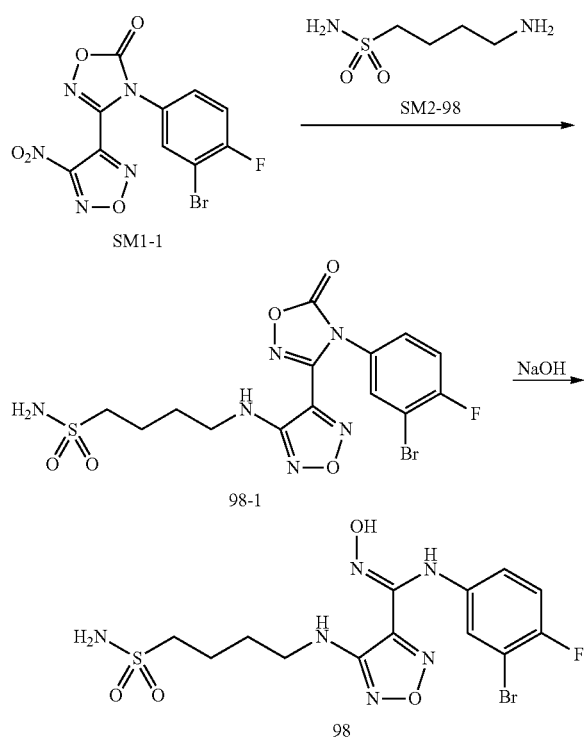

Sodium azide (650 mg, 10 mmol) was weighed and dissolved in 5 mL water, and then was slowly added to the solution of starting material 1,4-butanesultone (2.72 g, 20 mmol) in acetone (5 mL). The mixture was stirred overnight at room temperature. The reaction solution was concentrated under reduced pressure and extracted with ethyl acetate (2*20 mL). After the aqueous phase was concentrated to dryness, it was slurried with acetone/methyl tert-butyl ether=1/1 (10 mL), filtered, and rinsed with methyl tert-butyl ether. The solid was dried, and 1.36 g product was obtained with a yield of 76%.

Phosphorus pentachloride (1.7 g, 8 mmol) was added to 20 mL toluene solution of the reaction product (1.36 g, 7.6 mmol) from the previous step, and the mixture was heated to reflux and reacted for 3 hours. TLC was used to monitor the disappearance of the reaction materials, and the reaction solution was concentrated under reduced pressure, to provide 1.49 g product that was directly used in the next step, with a yield of 100%.

10 mL ammonia water was slowly added to 10 mL ethanol solution of the product from the previous step (1.49 g, 7.6 mmol), and the reaction was stirred at room temperature for 2 h. TLC was used to monitor the disappearance of the reaction materials. The reaction solution was concentrated under reduced pressure, and 10 mL ethyl acetate was added to make a slurry, filtered, rinsed with ethyl acetate, and the organic phases were combined and concentrated, to obtain 850 mg product as colorless oil with a yield of 63%.

The product from the previous step (300 mg, 1.68 mmol) was dissolved in a mixed solution of water/ethanol (3 mL/3 mL), to which was added 0.2 g (10%) palladium-carbon catalyst. Hydrogen was purged and exchanged for three times. The reaction was stirred overnight at room temperature, and TLC was used to monitor the disappearance of reaction materials. The reaction solution was filtered, rinsed with ethanol, and the organic phases were combined and concentrated, to obtain 248 mg SM2-98 as colorless oil, with a yield of 97%.

Compound SM2-98 (248 mg, 1.32 mmol) and starting material SM1-1 (245 mg, 0.66 mmol) were sequentially added to 10 mL THF, to which was added saturated sodium bicarbonate solution (2 ml), and the mixture was allowed to react overnight under stirring at room temperature. TLC was used to monitor the reaction until the starting material almost disappeared. 10 mL water was added, and extracted with 10 mL ethyl acetate. The organic layer was washed twice with saturated brine and dried over anhydrous sodium sulfate. The organic phase was concentrated under reduced pressure, to provide 266 mg intermediate 98-1, with a yield of 84%.

Intermediate 98-1 (103 mg, 0.22 mmol) was dissolved in 5 mL THF, then 2 N NaOH (1.5 ml) was added, and the reaction was stirred at room temperature for 30 minutes. TLC was used to monitor the complete reaction of starting materials. 10 mL water was added, and the reaction mixture was extracted with 10 mL ethyl acetate. The organic layer was washed with saturated brine and dried over anhydrous sodium sulfate. The organic phase was concentrated under reduced pressure, to provide 80 mg target compound 98 as white solid, with a yield of 81%.

MS (ESI) m/z 451.0 [M+H]$^+$.

$^1$HNMR (DMSO-$d_6$, 400 MHz) δ 11.46 (1H, s), 8.89 (1H, s), 7.19 (1H, t), 7.11 (1H, dd), 6.77 (3H, m), 6.19 (1H, t), 3.24-3.22 (2H, m), 3.02-2.98 (2H, m), 1.73-1.68 (4H, m).

Example 23: N-(3-bromo-4-fluorophenyl)-4-((3-((3-fluoropyrrolidin-1-yl)sulfonyl)propyl)amino)-N'-hydroxyl-1,2,5-oxadiazol-3-formamidine (Compound 39)

Compound 39 was prepared by a method similar to the synthesis of compound 40.

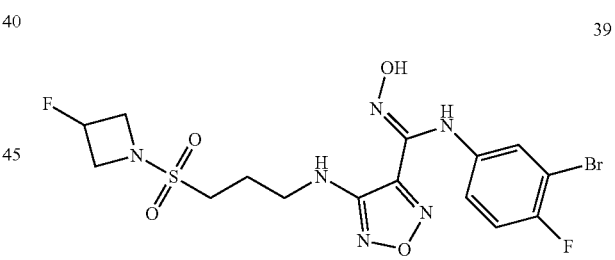

MS (ESI$^+$) m/z 497 [M+H]$^+$.

$^1$H NMR (400 MHz, DMSO) δ 11.45 (s, 1H), 8.92 (s, 1H), 7.18 (t, J=8.8 Hz, 1H), 7.12 (dd, J=6.0, 2.7 Hz, 1H), 6.80-6.73 (m, 1H), 6.34 (t, J=5.9 Hz, 1H), 5.38 (dddd, J=57.2, 9.7, 6.0, 3.8 Hz, 1H), 4.17 (ddd, J=20.2, 10.8, 6.0 Hz, 2H), 4.01 (dd, J=10.8, 3.7 Hz, 1H), 3.95 (dd, J=10.8, 3.7 Hz, 1H), 3.31 (d, J=6.6 Hz, 2H), 3.26-3.17 (m, 2H), 1.97 (dt, J=14.5, 7.1 Hz, 2H).

Example 24: N-(3-bromo-4-fluorophenyl)-N'-hydroxyl-4-((3-(morpholino)propyl)amino)-1,2,5-oxadiazol-3-formamidine (Compound 43)

Compound 43 was prepared by a method similar to the synthesis of compound 18.

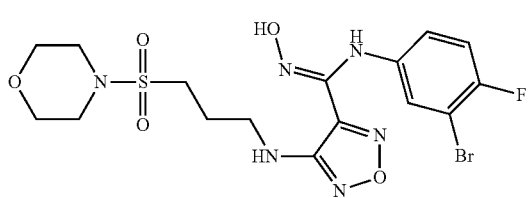

43

LC/MS (ESI⁺) m/z 493 (M+H⁺).
¹H NMR (400 MHz, DMSO-d₆) δ 11.45 (s, 1H), 8.91 (s, 1H), 7.18 (t, J=8.8 Hz, 1H), 7.11 (dd, J=6.1, 2.7 Hz, 1H), 6.79-6.73 (m, 1H), 6.33 (d, J=5.7 Hz, 1H), 3.66-3.60 (m, 6H), 3.16-3.12 (m, 6H), 1.97 (d, J=7.2 Hz, 2H).

Example 25: 4-((4-(azetidin-1-ylsulfonyl)butyl)amino)-N-(3-bromo-4-fluorophenyl)-N'-hydroxyl-1,2,5-diazol-3-formamidine (Compound 117)

Compound 117 was prepared by a method similar to the synthesis of compound 40.

117

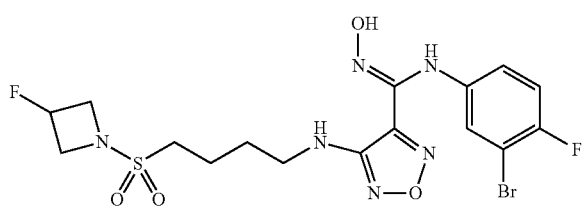

MS (ESI+) m/z 493 (M+H⁺).
¹H NMR (400 MHz, DMSO-d₆) δ 11.48 (s, 1H), 8.92 (s, 1H), 7.19 (t, J=8.8 Hz, 1H), 7.12 (dd, J=6.0, 2.6 Hz, 1H), 6.81-6.70 (m, 1H), 6.24 (t, J=5.8 Hz, 1H), 3.83 (q, J=7.2 Hz, 4H), 3.25 (d, J=5.8 Hz, 2H), 3.14 (t, J=7.1 Hz, 2H), 2.21-2.12 (m, 2H), 1.70 (d, J=3.2 Hz, 4H).

Example 26: N-(3-bromo-4-fluorophenyl)-4-((4-((3-fluorazetidin-1-yl)sulfonyl)butyl)amino)-N'-hydroxyl-1,2,5-oxadiazol-3-amide (Compound 121)

Compound 121 was prepared by a method similar to the synthesis of compound 40.

121

MS (ESI+) m/z 509 [M+Na]⁺.
¹H NMR (400 MHz, DMSO-d₆) δ 11.48 (s, 1H), 8.92 (s, 1H), 7.22 (t, J=8.8 Hz, 1H), 7.12 (dd, J=6.1, 2.7 Hz, 1H), 6.77 (ddd, J=8.8, 4.0, 2.9 Hz, 1H), 6.25 (t, J=5.9 Hz, 1H), 5.45-5.32 (m, 1H), 4.20-3.94 (m, 4H), 3.26-3.21 (m, 4H), 1.71-1.70 (m, 4H).

Example 27: N-(3-bromo-4-fluorophenyl)-N'-hydroxyl-4-((3-(N-(methyl-d₃)sulfonyl)propyl)amino)-1,2,5-oxadiazol-3-oximecarboxamide (Compound 127)

Using deuterated methylamine hydrochloride as starting material, SM2-127 was prepared by a method similar to that of SM2-22, and compound 127 was prepared by a method similar to the synthesis of compound 22.

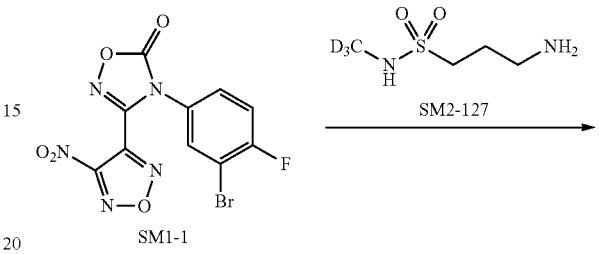

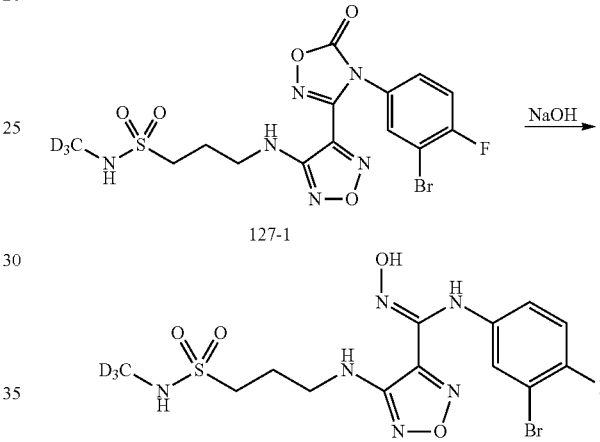

127

MS (ESI⁺) m/z 454 [M+H]⁺.
¹H NMR (400 MHz, DMSO-d₆) δ 12.32-10.61 (m, 2H), 9.02-8.54 (m, 1H), 7.19 (t, J=8.8 Hz, 1H), 7.12 (d, J=3.4 Hz, 1H), 6.83-6.73 (m, 1H), 6.40 (s, 1H), 3.30-3.21 (m, 2H), 3.14-2.99 (m, 2H), 2.06-1.88 (m, 2H).

Example 28: N-(3-bromo-4-fluorophenyl)-4-((3-(N,N-bis(tri-deuterated methyl)amino)propyl)amino)-N'-hydroxyl-1,2,5-diazol-3-formamidine (Compound 128)

SM2-128 was prepared using deuterated dimethylamine hydrochloride as starting material, and compound 128 was prepared by a method similar to the synthesis of compound 36.

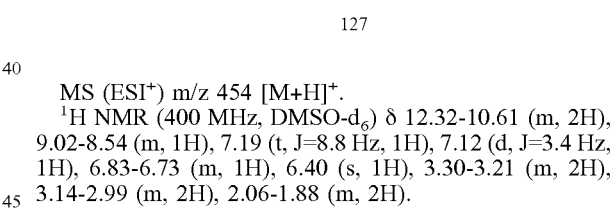

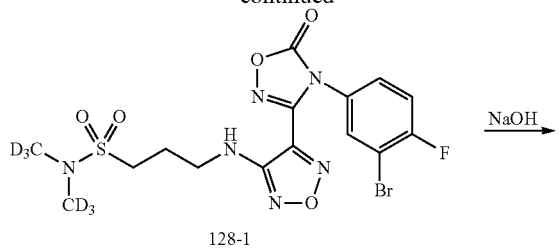

128-1

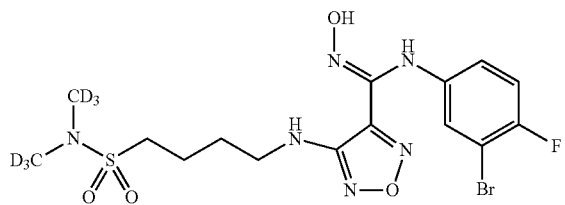 [SMILES: [2H]C([2H])([2H])N(C([2H])([2H])[2H])S(=O)(=O)CCCCNc1nonc1/C(=N/O)Nc1ccc(F)c(Br)c1]

MS (ESI+) m/z 485 [M+H]+.

¹H NMR (400 MHz, MeOD) δ 7.15 (dd, J=6.0, 2.7 Hz, 1H), 7.07 (t, J=8.7 Hz, 1H), 6.86 (ddd, J=8.8, 4.1, 2.7 Hz, 1H), 3.37 (d, J=6.5 Hz, 2H), 3.13-3.04 (m, 2H), 1.84 (ddd, J=18.1, 11.3, 5.2 Hz, 4H).

Example 31: N-(3-bromo-4-fluorophenyl)-N'-hydroxyl-4-(2-(2-aminosulfonylethoxyl)-ethylamine)-1,2,5-diazol-3-formamidine (Compound 136)

Compound 136 was prepared by a method similar to that of compound 127.

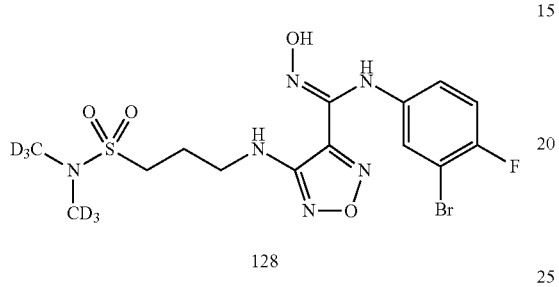

128

LC/MS (ESI+) m/z 471.2 [M+H]+.

¹H NMR (400 MHz, DMSO-d₆) δ 11.44 (s, 1H), 8.90 (s, 1H), 7.18 (t, J=8.8 Hz, 1H), 7.11 (dd, J=6.0, 2.7 Hz, 1H), 6.82-6.72 (m, 1H), 6.32 (t, J=5.8 Hz, 1H), 3.36-3.25 (m, 2H), 3.12-3.03 (m, 2H), 2.03-1.88 (m, 2H).

Example 29: N-(3-bromo-4-fluorophenyl)-N'-hydroxyl-4-((4-(N-deuterated methylsulfamoyl)butyl)amino)-1,2,5-oxadiazol-3-formamidine (Compound 134)

Compound 134 was prepared by a method similar to that of compound 127.

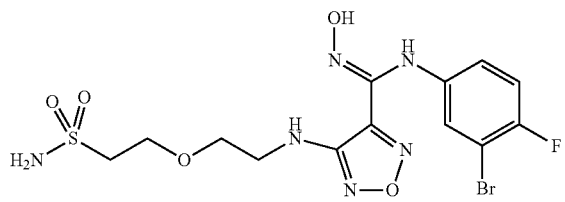 [SMILES: NS(=O)(=O)CCOCCNc1nonc1/C(=N/O)Nc1ccc(F)c(Br)c1]

MS (ESI+) m/z 467 [M+H]+.

¹H NMR (400 MHz, DMSO-d₆) δ 11.52 (s, 1H), 8.90 (s, 1H), 7.19 (t, J=8.8 Hz, 1H), 7.12 (dd, J=6.0, 2.8 Hz, 1H), 6.84 (s, 2H), 6.78 (m, 1H), 6.21 (t, J=6.0 Hz, 1H), 3.78 (t, J=6.8 Hz, 2H), 3.61 (t, J=5.6 Hz, 2H), 3.39 (m, 2H), 3.30 (t, J=6.8 Hz, 2H).

Example 32: N-(3-bromo-4-fluorophenyl)-N'-hydroxyl-4-((3-(N-((methyl-d₃)sulfamoyl)propyl)sulfur)-1,2, 5-oxadiazol-3-oximecarboxamide (Compound 152)

Using synthetic method B, similar to the method of compound 45, compound 152 was prepared with SM152-1 (purchased).

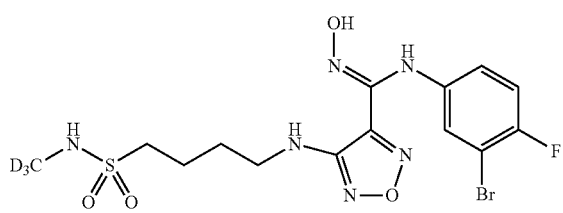

MS (ESI+) m/z 468 [M+H]+.

¹H NMR (400 MHz, CD₃OD) δ 7.14 (dd, J=6.0, 2.7 Hz, 1H), 7.07 (t, J=8.7 Hz, 1H), 6.86 (ddd, J=8.8, 4.1, 2.7 Hz, 1H), 3.37 (d, J=6.5 Hz, 2H), 3.14-3.06 (m, 2H), 2.71 (d, J=4.2 Hz, 3H), 1.94-1.76 (m, 4H).

Example 30: N-(3-bromo-4-fluorophenyl)-4-((4-(N,N-bis(trideuteratedmethyl)amino)butyl)amino)-N'-hydroxyl-1,2,5-diazol-3-formamidine (Compound 135)

Compound 135 was prepared by a method similar to that of compound 127.

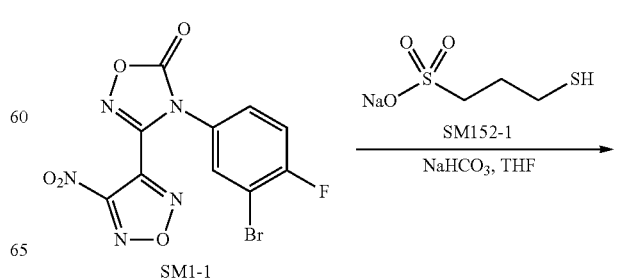

SM1-1

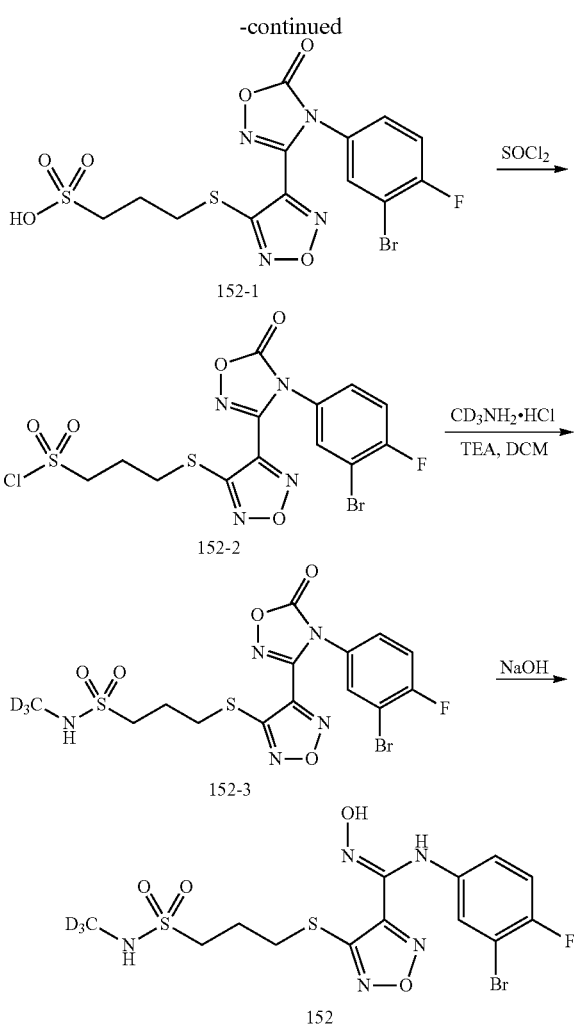

MS (ESI⁺) m/z 471 [M+H]⁺.

$^1$H NMR (400 MHz, CDCl$_3$) δ 8.43 (s, 1H), 7.17 (dd, J=5.8, 2.5 Hz, 1H), 7.13 (s, 1H), 7.01 (t, J=8.4 Hz, 1H), 6.86-6.77 (m, 1H), 4.48 (s, 1H), 3.33 (t, J=6.9 Hz, 2H), 3.19 (t, J=7.1 Hz, 2H), 2.30 (dd, J=15.3, 8.5 Hz, 2H).

Example 33

N-(3-bromo-2-fluorophenyl)-N'-hydroxyl-4-((3-(N-trideuteratedmethylsulfamoyl)propyl)sulfur)-1,2,5-oxadiazol-3-formamidine (Compound 153)

Compound 153 was prepared by a method similar to that of compound 152.

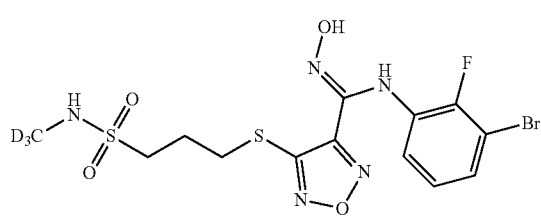 [SMILES: [2H]C([2H])([2H])NS(=O)(=O)CCCSc1nonc1/C(=N/O)Nc1cccc(Br)c1F]

MS (ESI⁺) m/z 472 M+H⁺.

$^1$H NMR (400 MHz, DMSO-d$_6$) δ 11.64 (s, 1H), 8.92 (s, 1H), 7.34 (dd, J=8.4, 5.0 Hz, 1H), 7.09-6.94 (m, 3H), 3.29 (t, J=7.2 Hz, 2H), 3.15 (dd, J=9.9, 5.4 Hz, 2H), 2.10 (dt, J=15.0, 7.5 Hz, 2H).

The beneficial effect of the present invention is elucidated by the following experimental examples: The use of the present invention will be further illustrated by the following biological experimental examples, but that does not mean to limit the application scope of the present invention.

Experimental Example 1: Determination of the Inhibitory Activity of the Compound According to the Present Invention Against Human IDO1 Protease 1) Experimental Materials and Apparatus:

IDO1 (His-tag) enzyme(BPS Bioscience), L-tryptophan (Sigma), methylene blue (Sigma), Catalase originated from the liver of cattle (Sigma), L-ascorbic acid (Sigma), glycerol (Sigma), potassium dihydrogen phosphate solution (Sigma), Tween 20 (Sigma), automatic sampling platformLiquid handler (Bravo & Echo), microplate ReaderSpectraMax M5e (Molecular Devices).

2) Test Method of Compounds: The Compounds are Determined by Absorbance Test Method:

The tested compounds are dissolved in DMSO to prepare a high concentration of storage solution. The stock solution of reference compound was diluted with DMSO to prepare a 100× solution. In the first column of the working plate, 8 µL above tested compounds and 8 µL 100× reference compound were respectively added as the highest concentration, and then the highest concentrations were subjected to three times dilution to obtain 11 concentrations and prepare 100× solution. 0.5 µL solution was transferred from the above plate to the detection plate. To each well was added 0.5 µL 100× compound solution. For HPE and ZPE control wells, 0.5 µL 100% DMSO was added. 25 µL 2×IDO1 (His-tag) enzyme solution (containing L-ascorbic acid, methylene blue, and catalase) was added to each well. 25 µL reaction solution without IDO1 (His-tag) enzyme was added into HPE control well. The test plate was centrifugated at 1000 rpm for 1 minute to mix well. Then, the test plate was incubated at room temperature for 30 minutes. 25 µL above 2× substrate (L-tryptophan) solution was added to each well. The test plate was centrifugated at 1000 rpm for 1 minute to mix well. The detection plate was placed on ELISA (SpectraMax M5e), the temperature was set at 25° C., and the absorbance (OD value) was measured at 320 nm every 10 minutes till 60 minutes.

Calculating the increase ratio of absorbance: the slope of the absorbance increase curve from 10 min to 60 min is derived from SpectralMax M5e. The inhibition coefficient of compound was calculated: the inhibition ratio of compound=(the absorbance increase ratio of ZPE control well−the absorbance increase ratio of compound well)/(the absorbance increase ratio of ZPE control well−the absorbance increase ratio of HPE control well)×100. Results was analyzed by Prism 5.0.

3) Results: IC$_{50}$ values of the compounds according to the present invention against the activity of human IDO1 protease are shown in Table 1.

TABLE 1

The inhibitory activity of compounds of the present invention against human IDO1 protease.

| Compound No. | IC$_{50}$ (nM) |
|---|---|
| 1 | 19 |
| 2 | 54 |
| 3 | 74 |
| 4 | 185 |
| 5 | 49 |
| 6 | 87 |
| 7 | 115 |
| 8 | 168 |
| 9 | 162 |
| 10 | 51 |
| 11 | 44 |
| 12 | 47 |
| 13 | 63 |
| 14 | 99 |
| 15 | 158 |
| 16 | 51 |
| 17 | 58 |
| 18 | 94 |
| 19 | 87 |
| 20 | 99 |
| 21 | 99 |
| 22 | 49 |
| 23 | 172 |
| 24 | 281 |
| 28 | 106 |

Conclusion: the compound of the present invention has obvious inhibitory effect on the activity of human IDO1 protease.

Experimental Example 2: Determination of Inhibition of Compounds According to the Present Invention on IDO Protease in HeLa Cells 1) Experimental Materials and Apparatus

| Experimental materials and apparatus | Manufacturer | No. |
|---|---|---|
| MEM | Gibco | 41090-036 |
| Penicillin-Streptomycin | Gibco | 15140-122 |
| Fetal bovine serum | Gibco | 10091-148 |
| Phosphate buffer solution(PBS) | Gibco | 10010-031 |
| Pancreatin substitute | Gibco | 12604-021 |
| DMSO | Sigma | D8418-1L |
| IFN-γ | R&D system | 285-IF-100/CF |
| CCl$_3$COOH | Sigma-aldrich | T0699 |
| P-dimethylaminobenzaldehyde | Sigma-aldrich | 15647-7 |
| Positive control compound INCB024360 | ChemExpress | HY-15683 |
| 96-well plate | Corning | 3599 |
| Apparatus | Manufacturer | Application |
| Centrifugal machine | Eppendorf | Centrifuge reaction mixture |
| Carbon dioxide incubator | Thermo Scientific | Cell culture |
| Enspire plate reader | PerkinElmer | Read 480 nm Signal |

2) Experimental Method for Compound Assay 2.1 Seeding HeLa Cells into 96 Well Plate The medium was taken out from the flask and the cells were washed with PBS. TrypLE solution was added to the flask to make the cells separate. The cells were further washed once with fresh medium containing 10% FBS, and then re-suspended in the medium until the final concentration was 2.3×10$^6$/mL. Only cells with activity greater than 90% can be used for detection. HeLa cells were planted into 100 μL suitable growth median 96 well plate at 3000 cells/well. The cells were incubated at 37° C. under 5% CO$_2$ overnight.

2.2 Preparation and Treatment of Compounds

The compound was diluted to the concentration of 10 mM with DMSO, that was then continuously diluted 3 times to get 9 concentrations. 5 μL compound was added into 45 μL media as the median dilution (10 times dilution, containing 10% DMSO). 96 μL fresh growth media were added to each well to reach the total volume of 196 μL. 2 μL compound solution was taken from the mid-diluted solution and added to the cells in the wells of the assay plate, and then incubated in a 5% CO$_2$ incubator at 37° C. for 30 minutes. 2 μL human IFN-γ solution was added to reach a total volume of 200 μL, with the final concentration of 10 ng/mL, and the final concentration is 0.1%. The cells were incubated in 5% CO$_2$ incubator at 37° C. for 48 h.

2.3 IDO/Kynurenine Experiment and Data Analysis

After incubating for another 48 hours in a 5% CO$_2$ incubator at 37° C., 140 μL supernatant was added to each well and transferred to a new 96-well plate. 10 μL of 6.1N CCl$_3$COOH was further added to each well, and incubated at 50° C. for 30 min after sealing. The plate was then centrifuged at 2500 rpm for 10 minutes. 100 μL supernatant in each well was transferred to another 96-well assay plate and mixed with 100 μL of 6% (w/v) p-dimethylaminobenzaldehyde. EnSpire was used to read the plate at OD480 nm.

The average data of HC (high control: 10 ng/mL IFN-γ) and LC (low control: no IFN-γ) were calculated for each screening plate. Percent inhibition of compound well (% inh)=100*(aveHC−cpd well)/(aveHC−ave LC). Finally, GraphPad Prism 6 software was used to calculate the IC$_{50}$ values of compounds and draw the effect-concentration curve.

1) Results: IC$_{50}$ values for compound of the present invention inhibiting IDO1 protease activity in Hela cells were shown in Table 2.

TABLE 2

Inhibitory activity against IDO1 protease activity in Hela cells(IC$_{50}$)

| Example No. | IC$_{50}$ (nM) |
|---|---|
| 2 | 19 |
| 3 | 35 |
| 5 | 15 |
| 10 | 9 |
| 11 | 8 |
| 12 | 12 |
| 13 | 30 |
| 14 | 37 |
| 16 | 32 |
| 17 | 10 |
| 22 | 12 |
| 25 | 93 |
| 26 | 113 |
| 27 | 10 |
| 28 | 16 |
| 29 | 20 |
| 30 | 24 |
| 31 | 68 |
| 32 | 17 |
| 33 | 69 |

The test results indicated that the compound of the present invention had an inhibitory effect on the IDO protease activity in Hela cells.

Experimental Example 3: Metabolic Stability Experiment on the Compound of the Present Invention in Liver Microsomes Step 1: the mother liquor is prepared according to the composition ratio in Table 3 below:

TABLE 3

Preparation of mother liquor

| Reagents | Concentration | Volume | Final concentration |
|---|---|---|---|
| Phosphate buffer | 200 mM | 200 μL | 100 mM |
| High purity water | — | 106 μL | — |
| MgCl₂ solution | 50 mM | 40 μL | 5 mM |

Step 2: two experiments were respectively carried out as follows:

A) Adding NADPH:10 μL of liver microsomes at a concentration of 20 mg/mL and 40 μL of NADPH at a concentration of 10 mM were added to the incubation test. The final concentrations of liver microsomes and NADPH were 0.5 mg/mL and 1 mM, respectively.

B) Without addition of NADPH:10 μL of liver microsomes at a concentration of 20 mg/mL and 40 μL of high purity water were added to the incubation test. The final concentration of liver microsome was 0.5 mg/mL.

Step 3: 4 μL of 200 M positive control or test compound was added and then the reaction was carried out. The positive control in this experiment was Verapamil. The final concentration of test compound was 2 M.

Step 4: 50 μL was respectively taken out from the reaction solutions at the time points of 0, 15, 30, 45 and 60 min. 4× volumes of acetonitrile and IS (alprazolam at the concentration of 100 nM, labetalol at the concentration of 200 nM, caffeine at the concentration of 200 nM and ketoprofen at the concentration of 2 μM) were added to the reaction solution. The sample was centrifuged at 3,220 gram gravity for 40 minutes. 100 μL high-purity water was added to 100 μL supernatant and then analyzed by LC-MS/MS.

Step 5: Data analysis: the peak area was determined from the extracted ion chromatogram. The slope value k was determined by linear regression of the natural logarithm from the curve produced by the remaining percentage of the parent drug vs the incubation time.

In vitro half-life (in vitro $t_{1/2}$) is determined by the slope value: in vitro $t_{1/2} = -(0.693/k)$ The in vitro$CL_{int}$ (in vitro$CL_{int}$, in unit of μL/min/mg) is converted from the in vitro half-life $t_{1/2}$ (min) using the following equation (average of repeated determinations):

$$\text{in vitro } CL_{int} = \frac{0.693}{t_{1/2}} \times \frac{\text{volume of incubation (μL)}}{\text{amount of proteins (mg)}}$$

Scale up $CL_{int}$ (in mL/min/kg) is converted from in vitro $t_{1/2}$ (min) by using the following formula (the average of repeated determinations):

$$\text{Scale up } CL_{int} = \frac{0.693}{t_{1/2}} \times \frac{\text{volume of incubation (μL)}}{\text{amount of proteins (mg)}} \times \text{Scaling Factor}$$

The experimental results for metabolic stability in liver microsomes of mice, rats and humans are listed in Table 4.

TABLE 4

The experimental results for metabolic stability in liver microsomes of mice, rats and humans

| Compound | Mouse liver microsomes Half-life $t_{1/2}$ (min) | Rat liver microsomes Half-life $t_{1/2}$ (min) | Human liver microsomes Half-life $t_{1/2}$ (min) |
|---|---|---|---|
| INCB024360 | 78 | 146 | 157 |
| Compound 1 | 48 | 104 | 447 |
| Compound 21 | 117 | 1092 | 216 |
| Compound 22 | 10 | 24 | 93 |
| Compound 23 | 23 | 19 | 164 |
| Compound 127 | 21 | 38 | 343 |
| Compound 98 | 87 | 73 | 1762 |

INCB024360 is an IDO inhibitor developed by Incyte, USA, and has entered clinical phase III. The data in Table 4 show that the metabolic stability of the compound of the present invention in human liver microsomes is significantly improved compared to the reference compound INCB024360, indicating that the compound of the present invention is likely to have better clinical pharmacokinetics.

Experimental Example 4: Pharmacokinetics of the Compounds According to the Present Invention in Mouse 1) Experimental Materials and Apparatus 1) LC-20AD high performance liquid chromatography system (SHIMADZU company, Japan)

API4000 triple quadrupole mass spectrometer (Applied Biosystem company, U.S.)

PhenixWinnolin pharmacokinetic software (Version 6.3, Certara company, U.S.)

High-speed refrigerated centrifuge (Thermo Fisher Scientific)

Analytical balance (Sartorius, SECURA225D-1CN)

Experimental animals: ICR mice (Chengdu Dashuo Experimental Animal Co., Ltd.)

DMA (Sigma)

CMC-Na (Chengdu Kelong Chemical)

Heparin (Chengdu Kelong Chemical)

2) Experimental Methods and Results 5 mg of compound (compound 4 of the present invention, using similar compound INCB-24360 in clinical Phase III as reference compound) was accurately weighed, and the corresponding vehicle was added to a final volume of 10 ml, then mixed by ultrasonic vortexing. The solution at the concentration of 0.5 mg/ml was prepared. The final solution (0.2 ml) prepared was stored at −20° C. for concentration determination. 9 healthy adult ICR mice (20-30 g) were fasted overnight (free access to water), and received the administration volume of 0.2 ml/10 g by gavage; just prior to administration and 0.5, 1, 2, 4, 6, 8, 12, and 24 h after administration, 0.1 ml blood was collected from the retroorbital venous plexus, centrifuged at 4° C. for 5 min to separate the plasma, and stored at −20° C. for testing. Then the concentration of test compound in plasma was measured by LC/MS/MS method.

TABLE 5

Pharmacokinetic parameters of the compounds of the present invention

| Compounds | Pharmacokinetic experiment in mice (PO, 10 mpk) | | | |
|---|---|---|---|---|
| | Peak hour $t_{max}$ (h) | Blood concentration $C_{max}$ (ng/mL) | Curve area AUC (ng * h/mL) | Half life $t_{1/2}$ (h) |
| Compound 1 | 0.67 | 555 | 1322 | 1.28 |
| Compound 22 | 0.5 | 687 | 845 | 1.15 |
| Compound 23 | 0.5 | 704 | 1079 | 2.87 |
| Compound 127 | 0.5 | 469 | 1048 | 2.5 |

The compounds of the present invention show good pharmacokinetics.

In summary, the compounds prepared in the present invention have significant inhibitory activity against IDO protease, and the in vivo metabolism is stable, showing good pharmacokinetics. Especially, the metabolic stability via human liver microsomes is better than that of the similar compound INCB024360, which has entered the clinic, indicating that the compound of the present invention may have better clinical pharmacokinetics. The compound of the present invention or the pharmaceutical composition can be used to prepare IDO inhibitory drugs, and can also be used to prepare drugs for preventing and/or treating diseases with pathological characteristics of IDO-mediated tryptophan metabolism pathway, with wide application value.

The invention claimed is:

1. A compound of formula (I), or an optical isomer thereof, or a cis- and trans-isomer thereof, or an isotope compound thereof, or a solvate thereof, or a pharmaceutically acceptable salt thereof, or a pro-drug thereof, or a tautomer thereof, or a mesomer thereof, or a racemate thereof, or an enantiomer thereof, or a diastereoisomer thereof, or a mixture thereof:

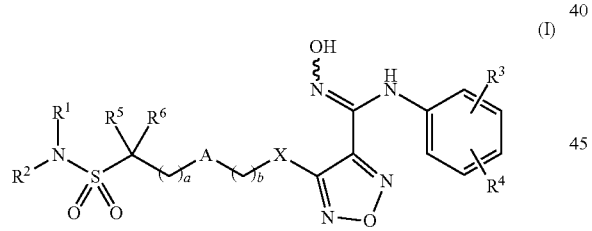

wherein, a and b are independently selected from an integer of 0-5;

X is selected from O, S, —O—NH—, —NH—, and —NH—O—;

A is selected from none, O, S,

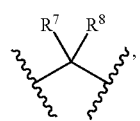

sulfuryl, sulfoxide, $C_3$-$C_7$ cycloalkyl, substituted $C_3$-$C_7$ cycloalkyl, $C_3$-$C_7$oxacycloalkyl, substituted $C_3$-$C_7$oxacycloalkyl, $C_3$-$C_7$azacycloalkyl, substituted $C_3$-$C_7$ azacycloalkyl,

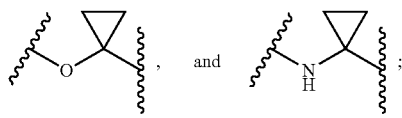 [SMILES: *OC1(*)CC1 ; *NC1(*)CC1]

$R^1$ and $R^2$ are independently selected from H, hydroxyl, amino, aryl, $C_1$-$C_6$ alkyl, substituted $C_1$-$C_6$ alkyl, $C_3$-$C_7$ cycloalkyl, substituted $C_3$-$C_7$ cycloalkyl, $C_3$-$C_7$heterocyclyl, substituted $C_3$-$C_7$heterocyclyl, $C_1$-$C_6$ alkoxyl, substituted $C_1$-$C_6$ alkoxyl, $C_1$-$C_6$ alkylamino, and substituted $C_1$-$C_6$ alkylamino; or $R^1$ and $R^2$ are linked to form a 3-8 membered heterocycle; or $R^1$ and $R^2$ are linked to form a substituted 3-8 membered heterocycle;

$R^3$ and $R^4$ are independently selected from H, halogen, cyano, trifluoromethyl, sulfuryl, sulfoxide, $C_1$-$C_6$ alkyl, substituted $C_1$-$C_6$ alkyl, $C_3$-$C_7$ cycloalkyl, substituted $C_3$-$C_7$ cycloalkyl, $C_1$-$C_6$ alkoxyl, and substituted $C_1$-$C_6$ alkoxyl; and $R^5$, $R^6$, $R^7$, $R^8$ are independently selected from H, deuterium, halogen, hydroxyl, amino, $C_1$-$C_6$ alkyl, $C_3$-$C_6$ cycloalkyl, $C_1$-$C_6$ alkoxyl, and $C_1$-$C_6$ alkylamino; or any two of $R^5$, $R^6$, $R^7$, and $R^8$ are linked to form a 3-8 membered carbocyclic ring.

2. The compound, or optical isomer thereof, or cis- and trans-isomer thereof, or isotope compound thereof, or solvate thereof, or pharmaceutically acceptable salt thereof, or pro-drug thereof, or tautomer thereof, or 3esomere thereof, or racemate thereof, or enantiomer thereof, or diastereoisomer thereof, or mixture thereof according to claim 1, wherein:

a and b are independently selected from integers of 0-5;

X is S or —NH—;

A is selected from none, O, sulfuryl,

$C_3$ cycloalkyl,

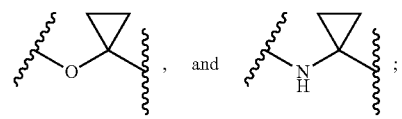

$R^1$ and $R^2$ are independently selected from H, hydroxyl, $C_1$-$C_3$ alkyl, substituted $C_1$-$C_3$ alkyl, $C_3$-$C_6$ cycloalkyl, methoxyl, and substituted $C_1$ alkylamino; or $R^1$ and $R^2$ are linked to form a 4-6 membered heterocycle; or $R^1$ and $R^2$ are linked to form a substituted 4-6 membered heterocycle;

substituents in said substituted $C_1$-$C_3$ alkyl are one or more selected from deuterium, hydroxyl, methyl-substituted $C_1$ alkylamino, amino, and halogen; the substituent in said substituted $C_1$ alkylamino is methyl; the heteroatoms in said substituted 4-6 membered heterocycle contains one or two heteroatoms selected from N and O; said substituted 4-6 membered heterocycle contains one or two N atoms; and said substituted 4-6 membered heterocycle is substituted by one or more selected from methyl, hydroxyl, and halogen;

R³ and R⁴ are halogen; and

R⁵, R⁶, R⁷, R⁸ are independently selected from H, deuterium, halogen, hydroxyl, and amino; or any two of R⁵, R⁶, R⁷, and R⁸ are linked to form a 3-4 membered carbocyclic ring.

3. The compound, or optical isomer thereof, or cis- and trans-isomer thereof, or isotope compound thereof, or solvate thereof, or pharmaceutically acceptable salt thereof, or pro-drug thereof, or tautomer thereof, or mesomer thereof, or racemate thereof, or enantiomer thereof, or diastereoisomer thereof, or mixture thereof according to claim 1, wherein said compound of formula (I) has the structure of formula (II):

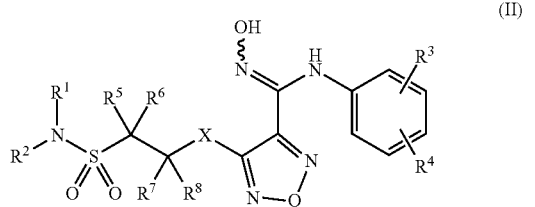
(II)

wherein, X is S or —NH—;

R¹ and R² are independently selected from H, hydroxyl, C₁-C₃ alkyl, substituted C₁-C₃ alkyl, C₃-C₆ cycloalkyl, methoxyl, and substituted C₁ alkylamino; or R¹ and R² are linked to form a 4-6 membered heterocycle; or R¹ and R² are linked to form a substituted 4-6 membered heterocycle;

substituents in said substituted C₁-C₃ alkyl are independently selected from deuterium, hydroxyl, methyl-substituted C₁ alkylamino, amino, and halogen; the substituent in said substituted C₁ alkylamino is methyl; said 4-6 membered heterocycle contains one or two heteroatoms selected from N and O; said substituted 4-6 membered heterocycle contains one or two N atoms; and substituents in said substituted 4-6 membered heterocycle are one or more selected from methyl, hydroxyl, and halogen;

R³ and R⁴ are halogen; and

R⁵, R⁶, R⁷, and R⁸ are independently selected from H, deuterium, halogen, hydroxyl, and amino; or any two of R⁵, R⁶, R⁷, and R⁸ are linked to form a 3-4 membered carbocyclic ring.

4. The compound, or optical isomer thereof, or cis- and trans-isomer thereof, or isotope compound thereof, or solvate thereof, or pharmaceutically acceptable salt thereof, or pro-drug thereof, or tautomer thereof, or mesomer thereof, or racemate thereof, or enantiomer thereof, or diastereoisomer thereof, or mixture thereof according to claim 2, wherein said compound of formula (I) has the structure of formula (III):

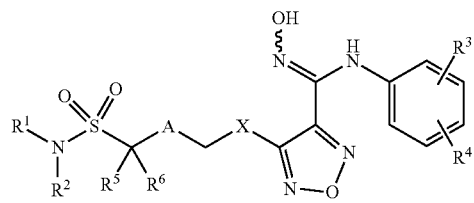
(III)

wherein, X is S or —NH—;

R¹ and R² are independently selected from H, hydroxyl, C₁-C₃ alkyl, substituted C₁-C₃ alkyl, C₃-C₆ cycloalkyl, methoxyl, and substituted C₁ alkylamino; or R¹ and R² are linked to form a 4-6 membered heterocycle; or R¹ and R² are linked to form a substituted 4-6 membered heterocycle;

the substituents in said substituted C₁-C₃ alkyl are one or more selected from deuterium, hydroxyl, methyl-substituted C₁ alkylamino, amino, and halogen; the substituent in said substituted C₁ alkylamino is methyl; said 4-6 membered heterocycle contains one or more heteroatoms selected from N and O; said substituted 4-6 membered heterocycle contains one or two N atoms; and substituents in said substituted 4-6 membered heterocycle are one or more selected from methyl, hydroxyl, and halogen;

R³ and R⁴ are halogen;

A is selected from none, O, sulfuryl,

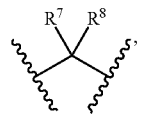

C₃ cycloalkyl,

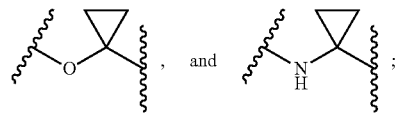 [SMILES: *OC1(*)CC1 ; *NC1(*)CC1], and

R⁵, R⁶, R⁷, R⁸ are independently selected from H, deuterium, halogen, hydroxyl, and amino; or any two of R⁵, R⁶, R⁷, and R⁸ are linked to form a 3-4 membered carbocyclic ring.

5. The compound, or optical isomer thereof, or cis- and trans-isomer thereof, or isotope compound thereof, or solvate thereof, or pharmaceutically acceptable salt thereof, or pro-drug thereof, or tautomer thereof, or mesomer thereof, or racemate thereof, or enantiomer thereof, or diastereoisomer thereof, or mixture thereof according to claim 2, wherein said compound of formula (I) has the structure of formula (IV):

(IV)

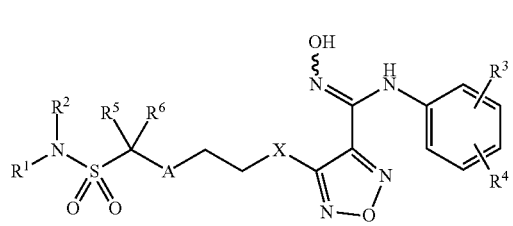

wherein, X is S or —NH—;

R$^1$ and R$^2$ are independently selected from H, hydroxyl, C$_1$-C$_3$ alkyl, substituted C$_1$-C$_3$ alkyl, C$_3$-C$_6$ cycloalkyl, methoxyl, and substituted C$_1$ alkylamino; or R$^1$ and R$^2$ are linked to form a 4-6 membered heterocycle; or R$^1$ and R$^2$ are linked to form a substituted 4-6 membered heterocycle;

substituents in said substituted C$_1$-C$_3$ alkyl are selected from deuterium, hydroxyl, methyl-substituted C$_1$ alkylamino, amino, and halogen; the substituent in said substituted C$_1$ alkylamino is methyl; said 4-6 membered heterocycle contains one or two heteroatoms selected from N and O; said substituted 4-6 membered heterocycle contains one or two N atoms; the substituents in said substituted 4-6 membered heterocycle are one or more selected from methyl, hydroxyl, and halogen;

R$^3$ and R$^4$ are halogen;

A is selected from none, O, sulfuryl,

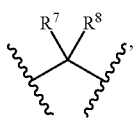

C$_3$ cycloalkyl,

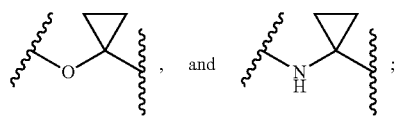

and

R$^5$, R$^6$, R$^7$, R$^8$ are independently selected from the group consisting of H, deuterium, halogen, hydroxyl, and amino; or any two of R$^5$, R$^6$, R$^7$, and R$^8$ are linked to form a 3-4 membered carbocyclic ring.

6. The compound, or optical isomer thereof, or cis- and trans-isomer thereof, or isotope compound thereof, or solvate thereof, or pharmaceutically acceptable salt thereof, or pro-drug thereof, or tautomer thereof, or mesomer thereof, or racemate thereof, or enantiomer thereof, or diastereoisomer thereof, or mixture thereof according to claim 2, wherein said compound of formula (I) has the structure of formula (V):

(V)

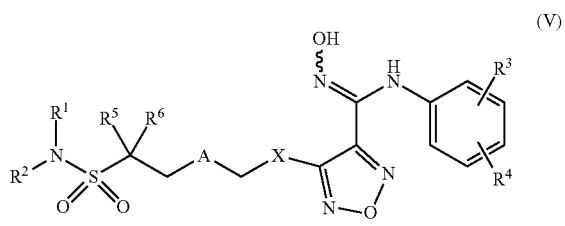

wherein, X is S or —NH—;

R$^1$ and R$^2$ are independently selected from H, hydroxyl, C$_1$-C$_3$ alkyl, substituted C$_1$-C$_3$ alkyl, C$_3$-C$_6$ cycloalkyl, methoxyl, and substituted C$_1$ alkylamino; or R$^1$ and R$^2$ are linked to form a 4-6 membered heterocycle; or R$^1$ and R$^2$ are linked to form a substituted 4-6 membered heterocycle;

substituents in said substituted C$_1$-C$_3$ alkyl are one or more selected from deuterium, hydroxyl, methyl-substituted C$_1$ alkylamino, amino, and halogen; the substituent in said substituted C$_1$ alkylamino is methyl; said 4-6 membered heterocycle contains one or two heteroatoms selected from N and O; said substituted 4-6 membered heterocycle contains one or two N atoms; the substituents in said substituted 4-6 membered heterocycle are selected from methyl, hydroxyl, and halogen;

R$^3$ and R$^4$ are halogen;

A is selected from none, O, sulfuryl,

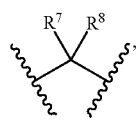

C$_3$ cycloalkyl,

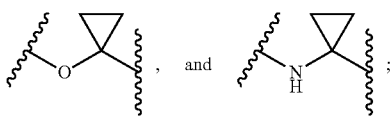

and

R$^5$, R$^6$, R$^7$, R$^8$ are independently selected from H, deuterium, halogen, hydroxyl, and amino; or any two of R$^5$, R$^6$, R$^7$, and R$^8$ are linked to form a 3-4 membered carbocyclic ring.

7. The compound, or optical isomer thereof, or cis- and trans-isomer thereof, or isotope compound thereof, or solvate thereof, or pharmaceutically acceptable salt thereof, or pro-drug thereof, or tautomer thereof, or mesomer thereof, or racemate thereof, or enantiomer thereof, or diastereoisomer thereof, or mixture thereof according to claim 2, wherein said compound of formula (I) has the structure of formula (VI):

(VI)

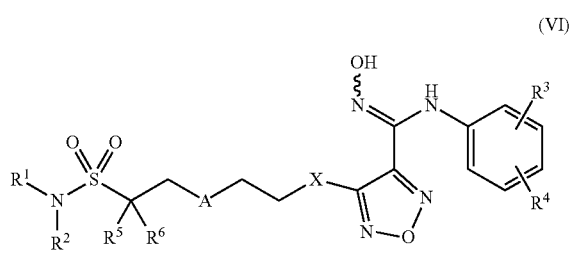

wherein, X is S or —NH—;

R¹ and R² are independently selected from H, hydroxyl, C₁-C₃ alkyl, substituted C₁-C₃ alkyl, C₃-C₆ cycloalkyl, methoxyl, and substituted C₁ alkylamino; or R¹ and R² are linked to form a 4-6 membered heterocycle; or R¹ and R² are linked to form a substituted 4-6 membered heterocycle;

substituents in said substituted C₁-C₃ alkyl are one or more selected from deuterium, hydroxyl, methyl-substituted C₁ alkylamino, amino, and halogen; the substituent in said substituted C₁ alkylamino is methyl; said 4-6 membered heterocycle contains one or more heteroatoms selected from N and O; said substituted 4-6 membered heterocycle contains one or two N atoms; and the substituents in said substituted 4-6 membered heterocycle are selected from methyl, hydroxyl, and halogen;

R³ and R⁴ are halogen;

A is selected from none, O, sulfuryl,

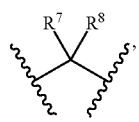

C₃ cycloalkyl,

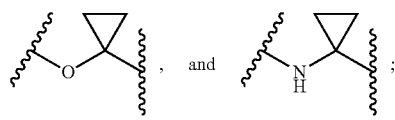

and

R⁵, R⁶, R⁷, R⁸ are independently selected from H, deuterium, halogen, hydroxyl, and amino; or any two of R⁵, R⁶, R⁷, and R⁸ are linked to form a 3-4 membered carbocyclic ring.

8. The compound, or optical isomer thereof, or cis- and trans-isomer thereof, or isotope compound thereof, or solvate thereof, or pharmaceutically acceptable salt thereof, or pro-drug thereof, or tautomer thereof, or mesomer thereof, or racemate thereof, or enantiomer thereof, or diastereoisomer thereof, or mixture thereof according to claim 2, wherein said compound of formula (I) has the structure of formula (VII):

(VII)

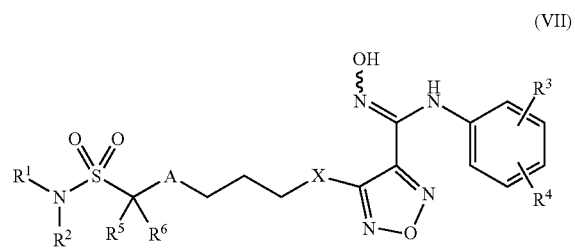

wherein, X is S or —NH—;

R¹ and R² are independently selected from H, hydroxyl, C₁-C₃ alkyl, substituted C₁-C₃ alkyl, C₃-C₆ cycloalkyl, methoxyl, and substituted C₁ alkylamino; or R¹ and R² are linked to form a 4-6 membered heterocycle; or R¹ and R² are linked to form a substituted 4-6 membered heterocycle;

the substituents in said substituted C₁-C₃ alkyl are one or more selected from deuterium, hydroxyl, methyl-substituted C₁ alkylamino, amino, and halogen; the substituent in said substituted C₁ alkylamino is methyl; 4-6 membered heterocycle are one or two heteroatoms selected from N and O; said substituted 4-6 membered heterocycle contains one or two N atoms; and the substituents in said substituted 4-6 membered heterocycle are one or more selected from methyl, hydroxyl, and halogen;

R³ and R⁴ are halogen;

A is selected from none, O, sulfuryl,

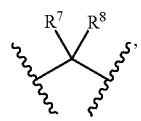

C₃ cycloalkyl,

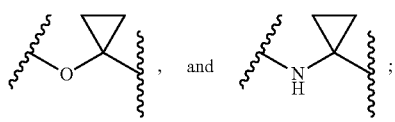 [SMILES: *OC1(*)CC1 ; *NC1(*)CC1]

R⁵, R⁶, R⁷, R⁸ are independently selected from H, deuterium, halogen, hydroxyl, and amino; or any two of R⁵, R⁶, R⁷, and R⁸ are linked to form a 3-4 membered carbocyclic ring.

9. The compound, or optical isomer thereof, or cis- and trans-isomer thereof, or isotope compound thereof, or solvate thereof, or pharmaceutically acceptable salt thereof, or pro-drug thereof, or tautomer thereof, or mesomer thereof, or racemate thereof, or enantiomer thereof, or diastereoisomer thereof, or mixture thereof according to claim 1, wherein said compound of formula (I) is one of the following:

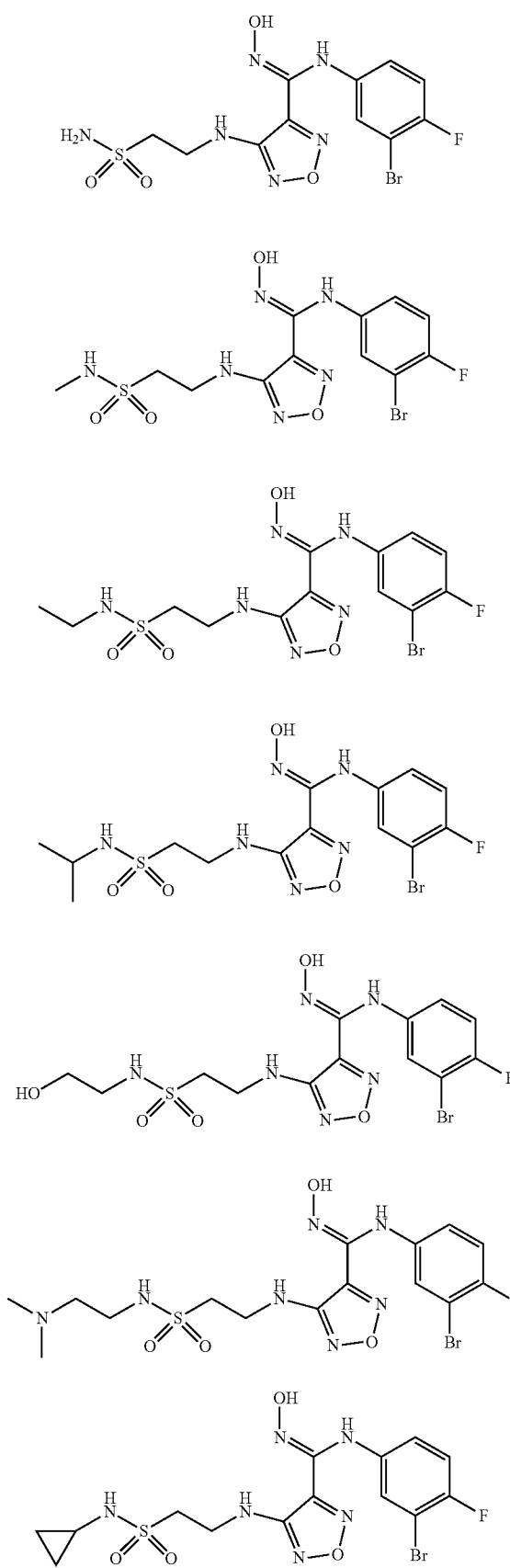
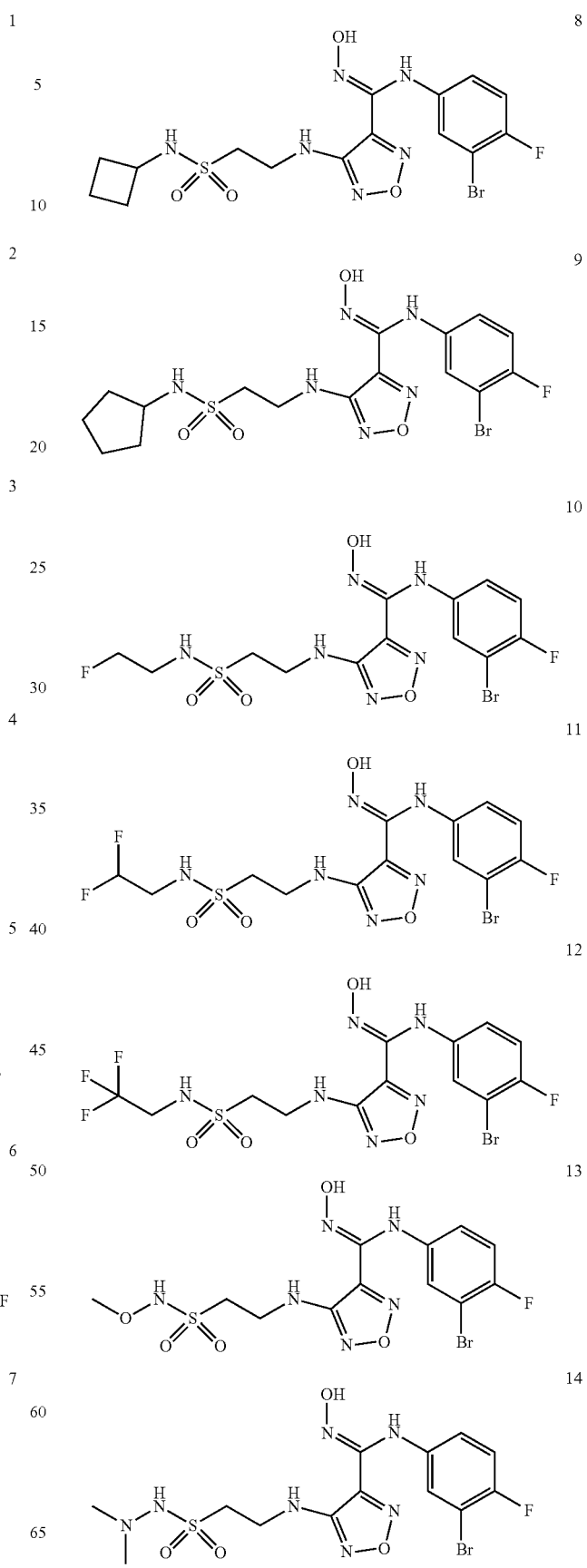

15
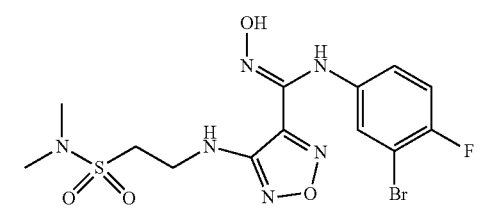
16
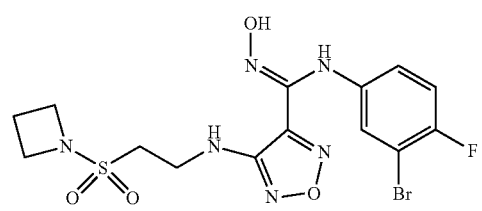
17
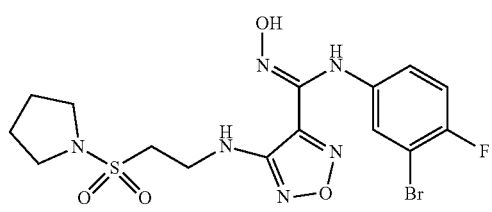
18
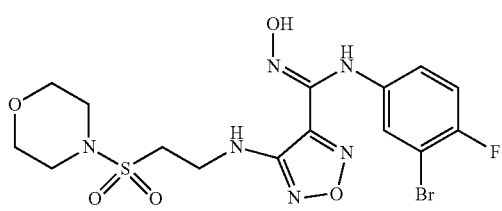
19
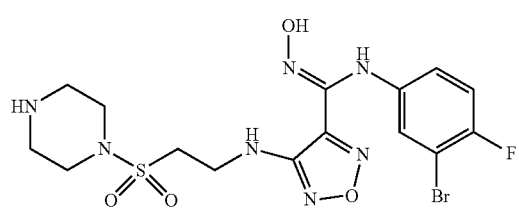
20
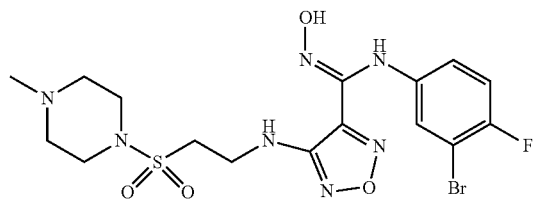
21
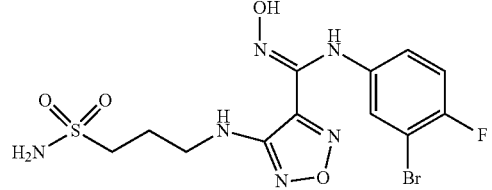
22
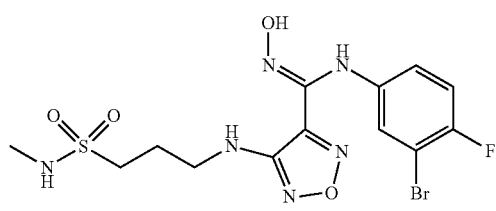
23
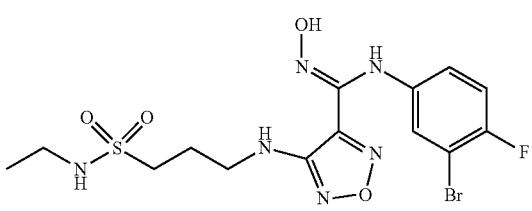
24
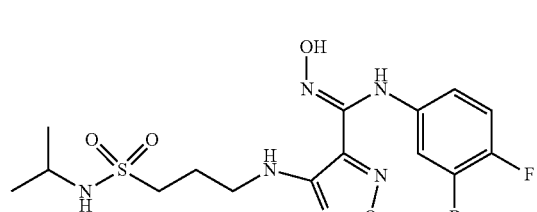
25
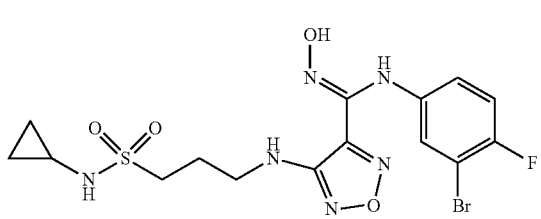
26
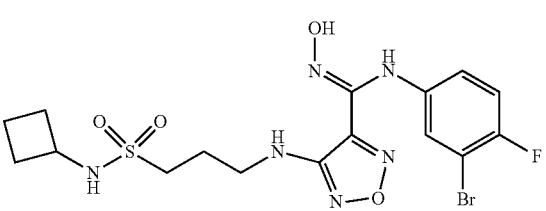
27
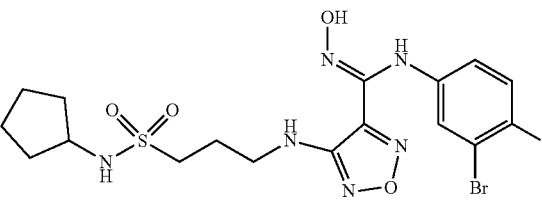
28
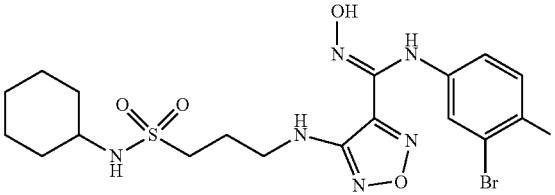

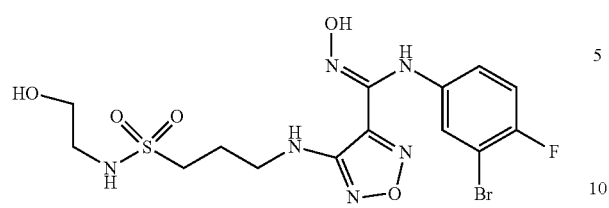
29
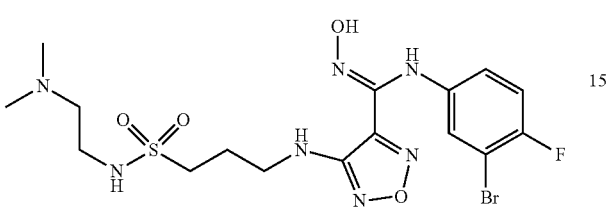
30
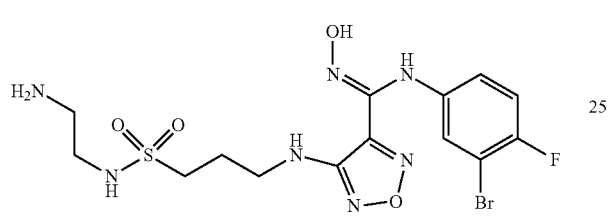
31
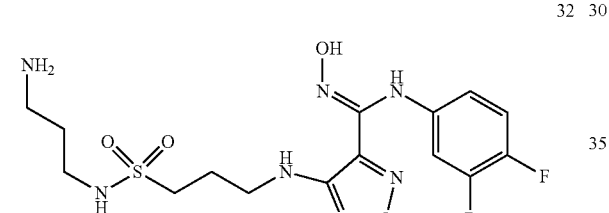
32
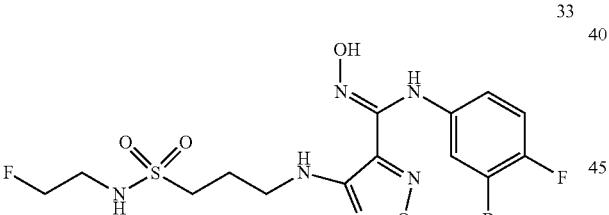
33
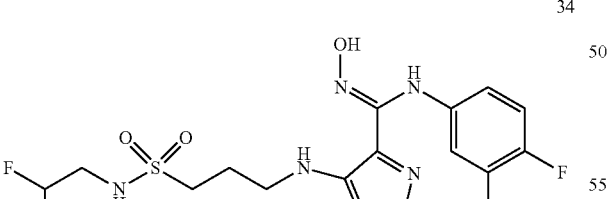
34
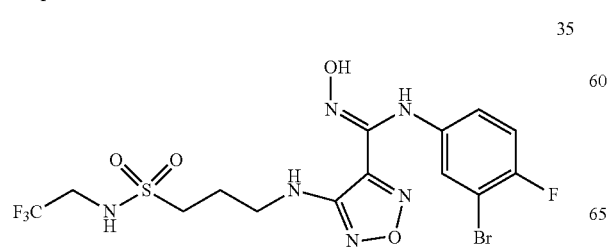
35
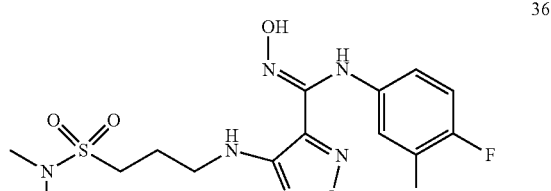
36
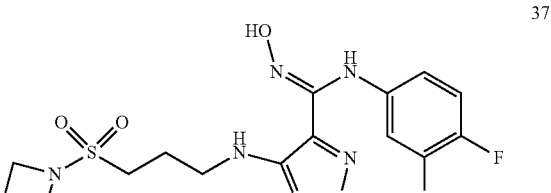
37
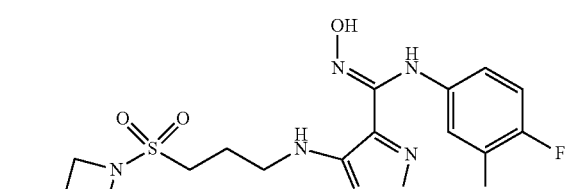
38
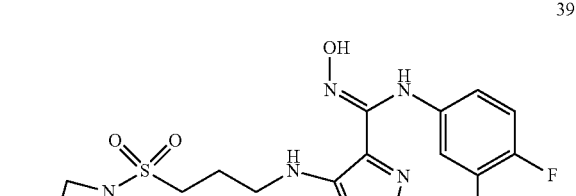
39
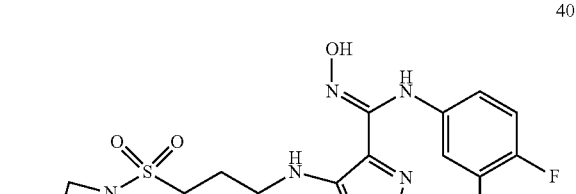
40
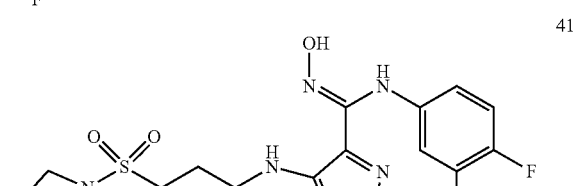
41
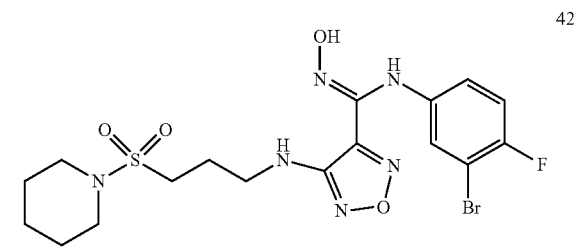
42

43
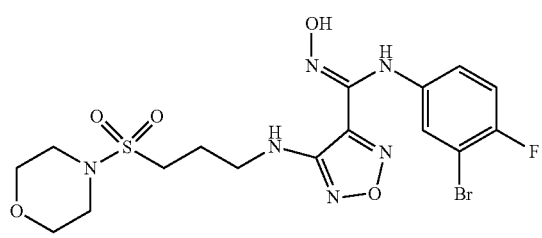
44
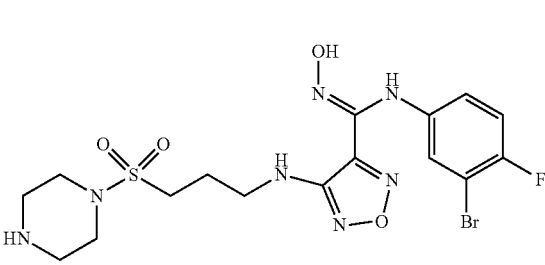
45
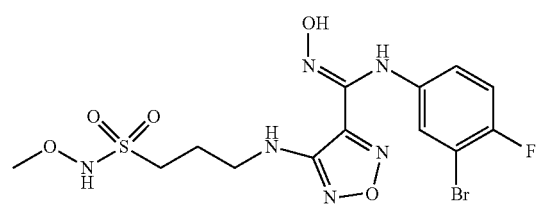
46
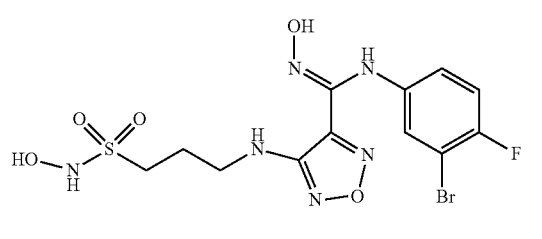
47
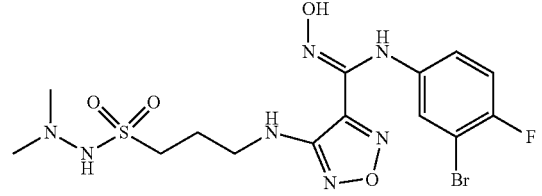
48
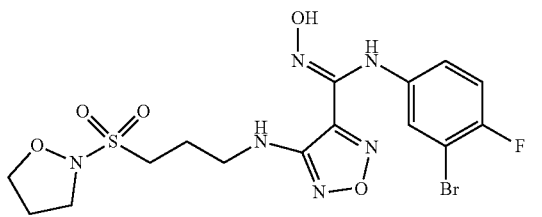
49
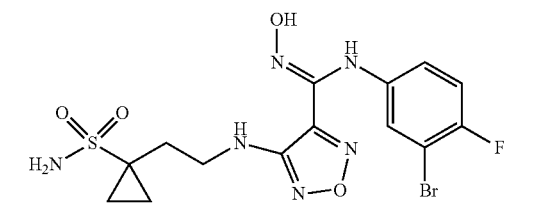
50
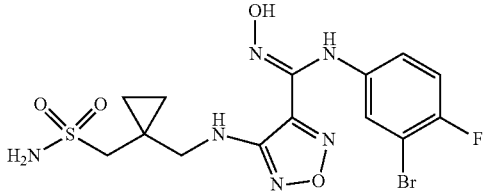
51
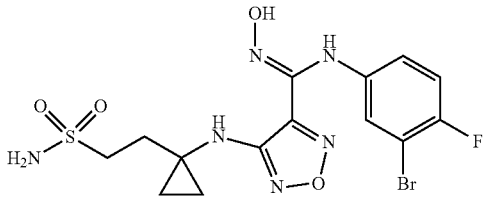
52
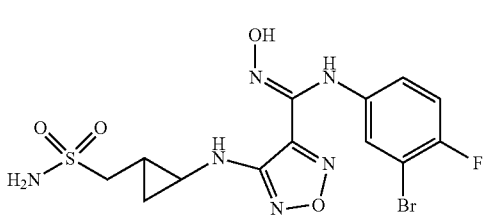
53
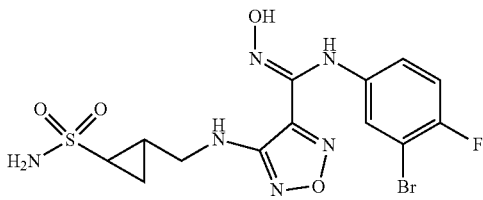
54
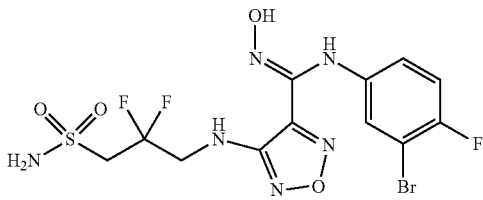
55
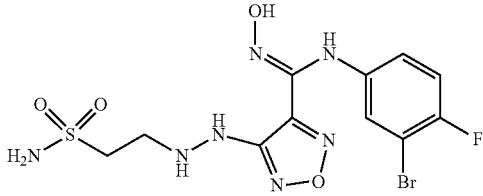
56
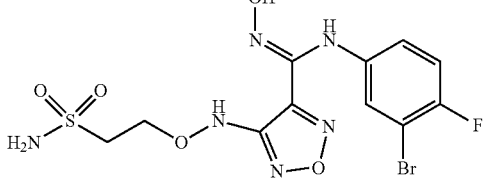

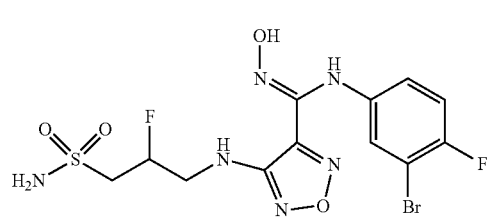
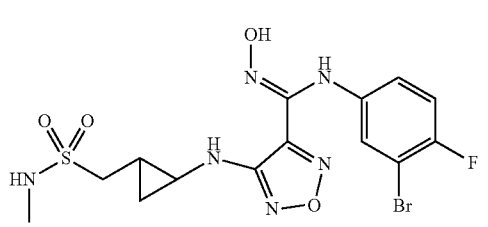
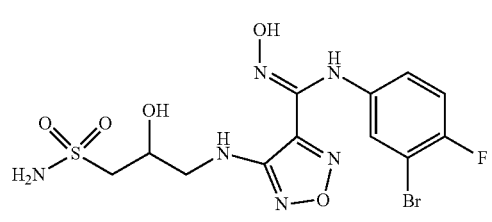
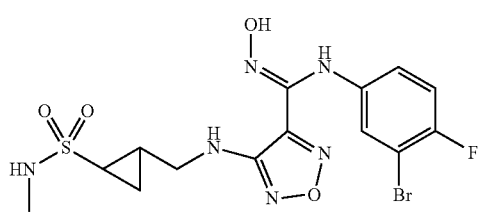
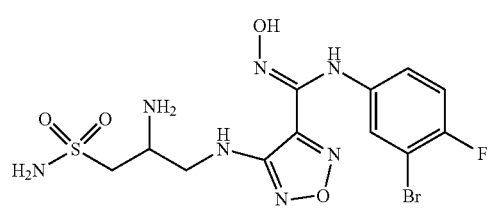
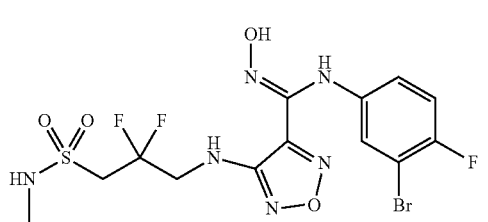
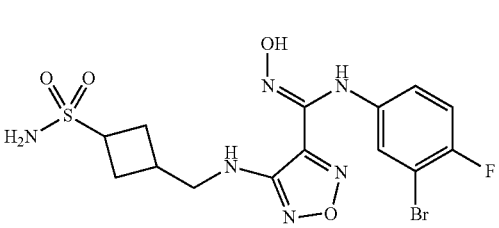
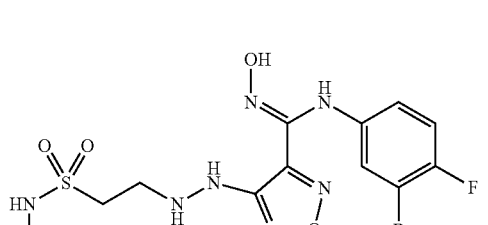
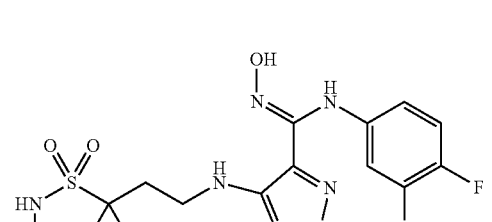
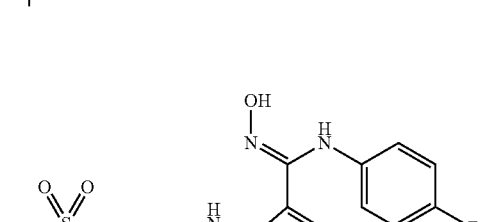
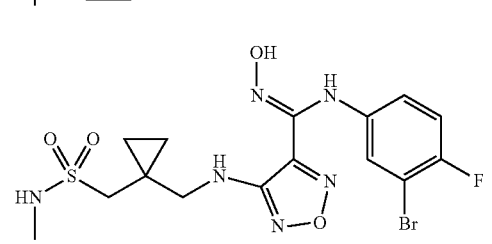
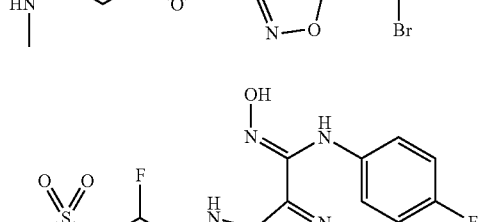
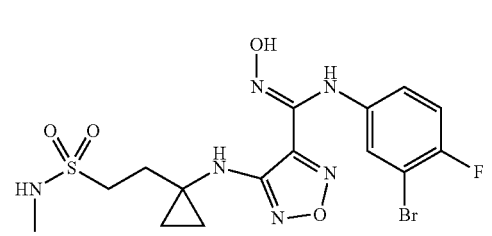
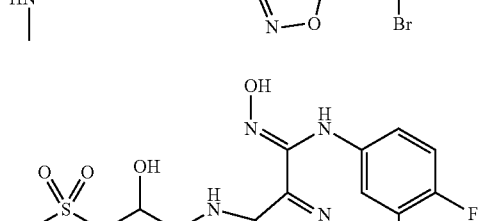

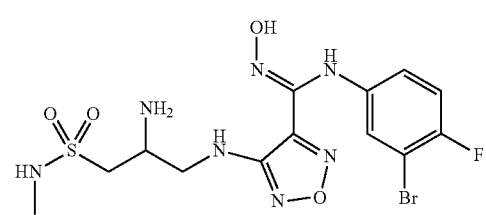
71
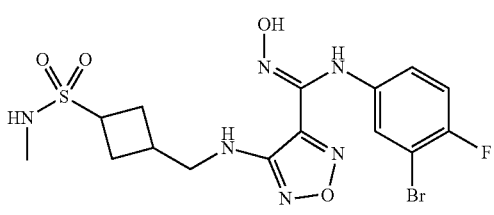
72
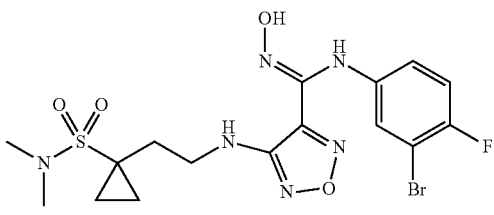
73
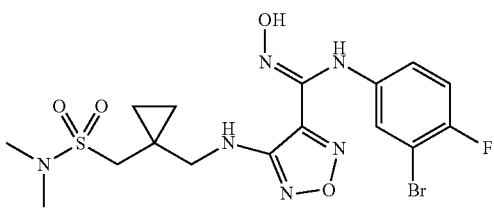
74
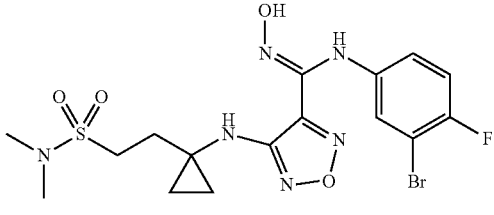
75
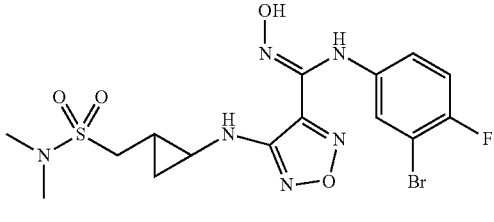
76
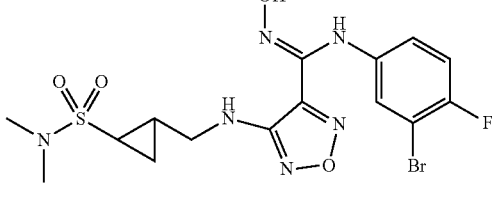
77
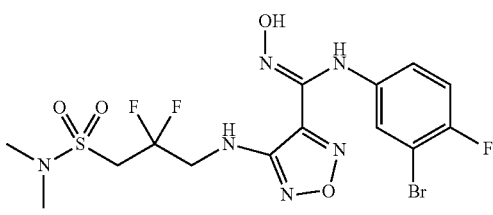
78
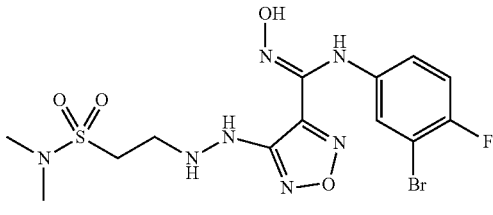
79
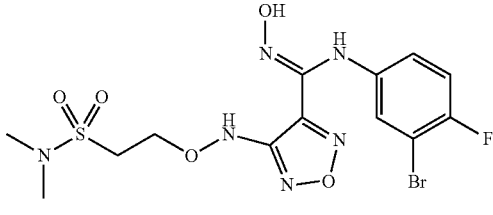
80
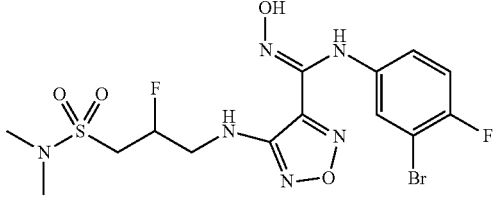
81
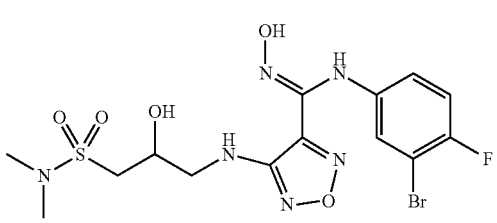
82
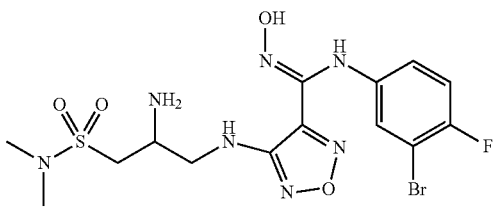
83
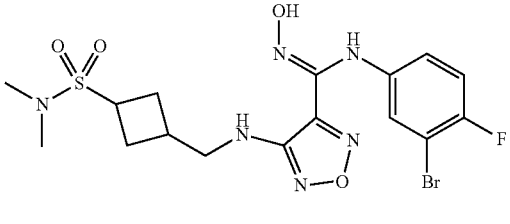
84

85
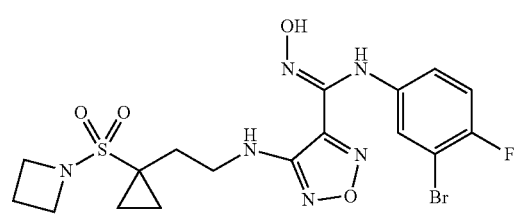
86
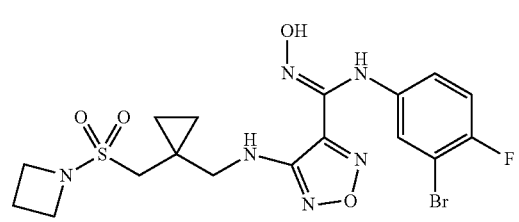
87
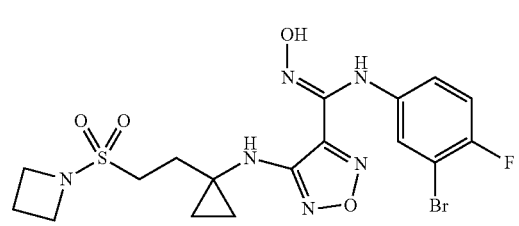
88
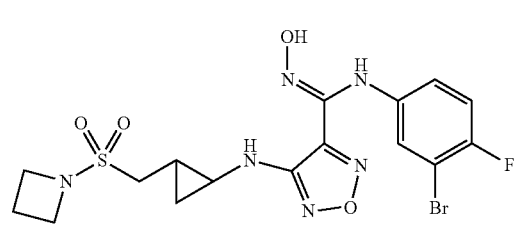
89
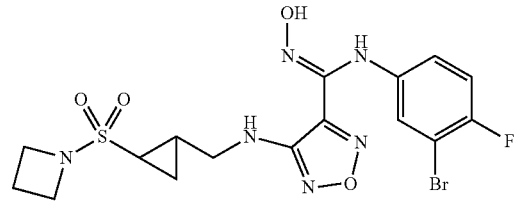
90
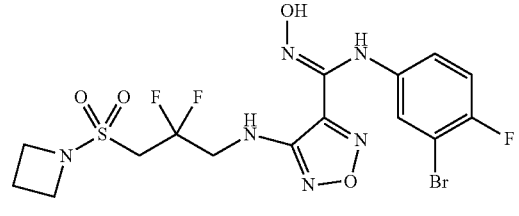
91
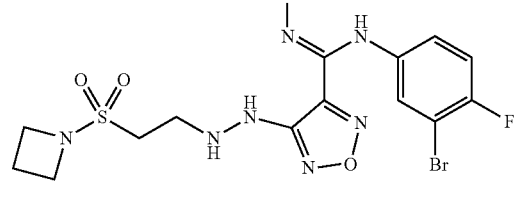
92
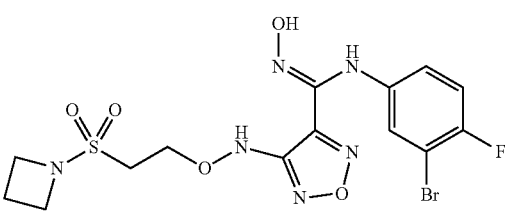
93
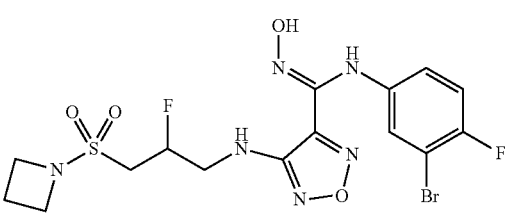
94
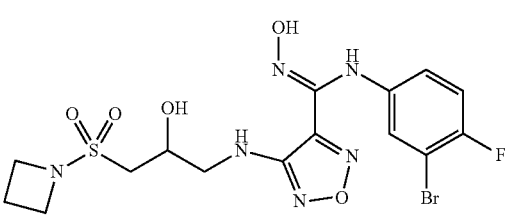
95
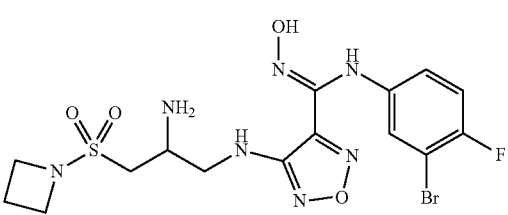
96
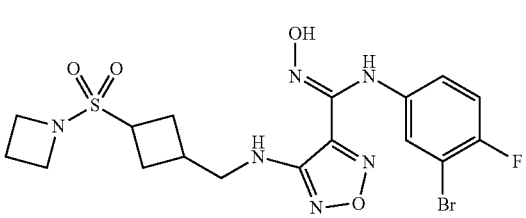
97
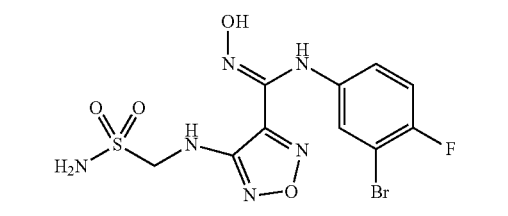
98
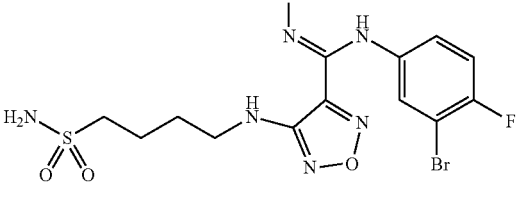

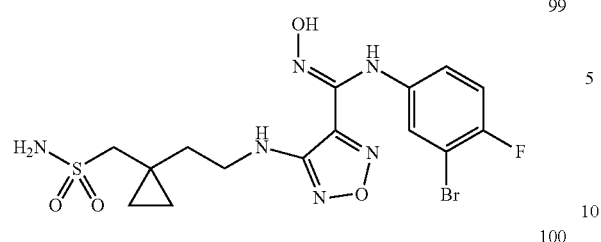
99
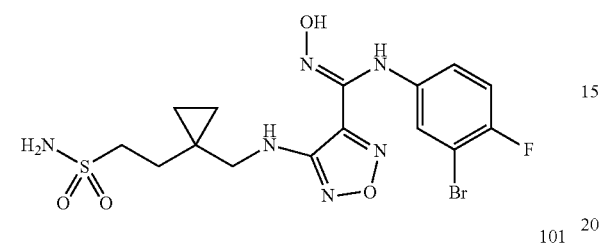
100
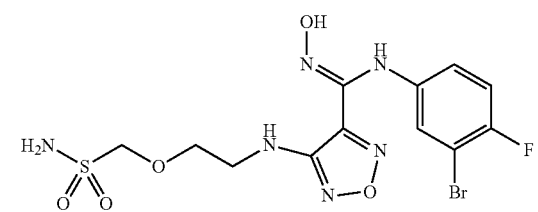
101
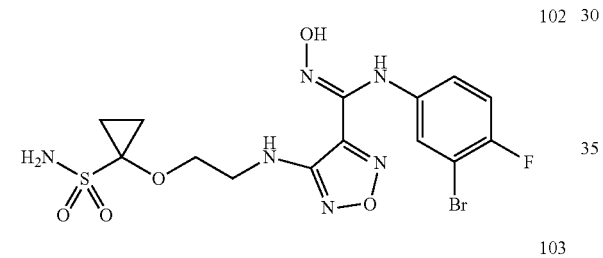
102
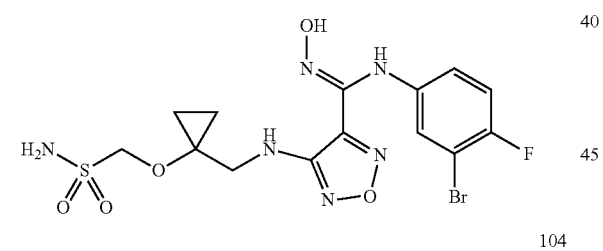
103
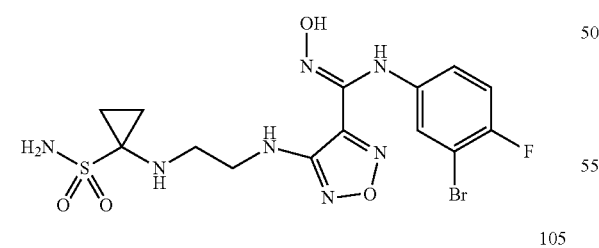
104
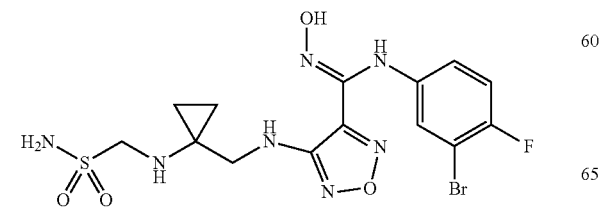
105
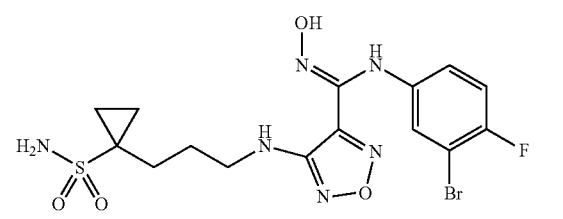
106
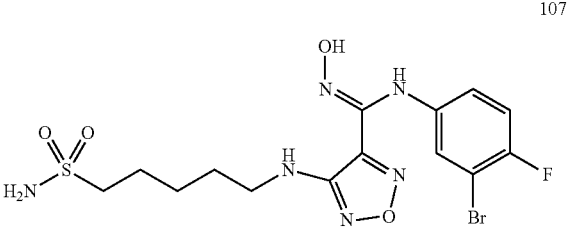
107
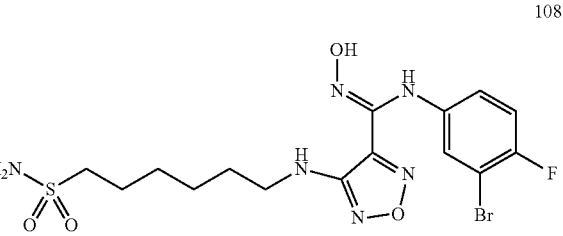
108
109
110
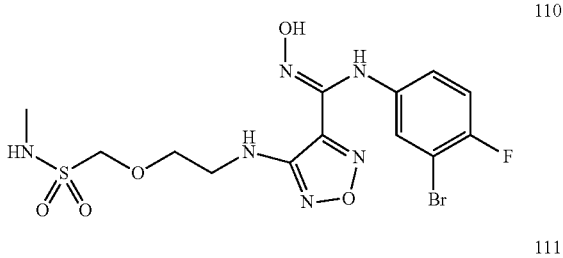
111
112
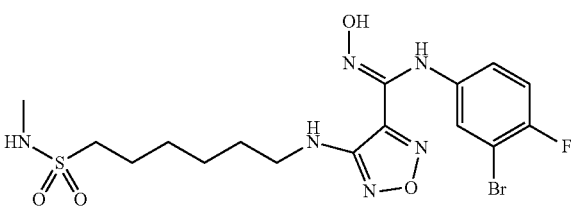

113
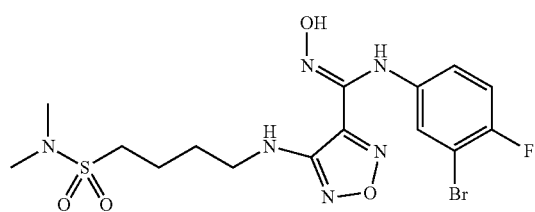
114
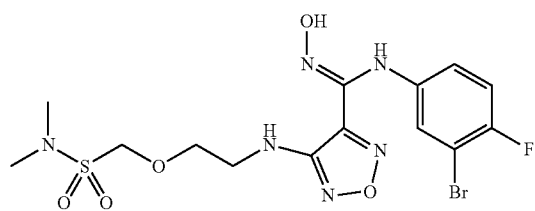
115
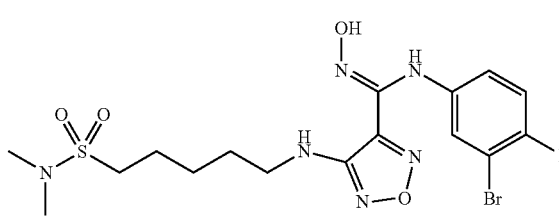
116
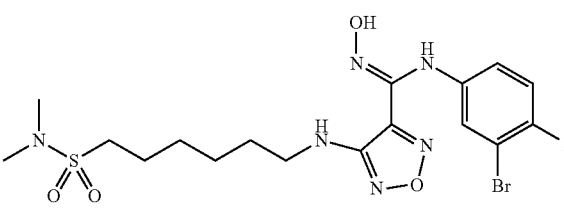
117
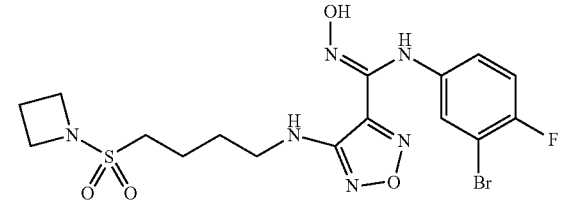
118
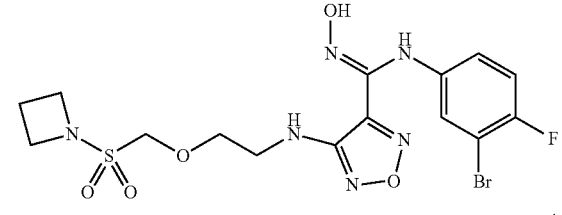
119
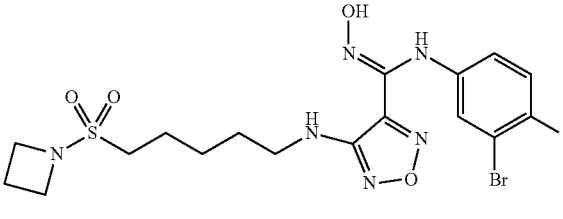
120
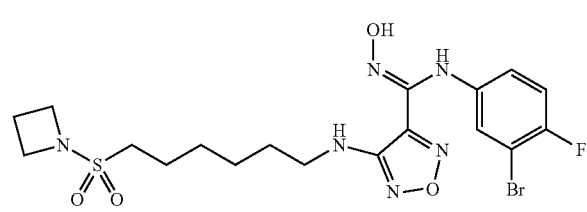
121
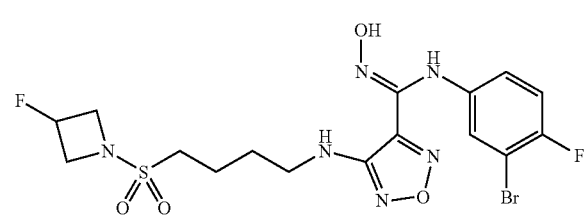
122
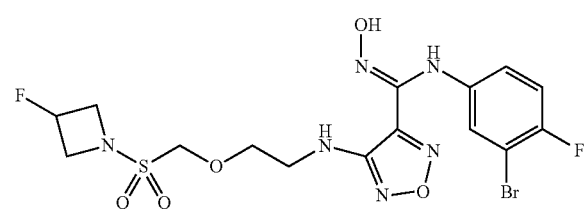
123
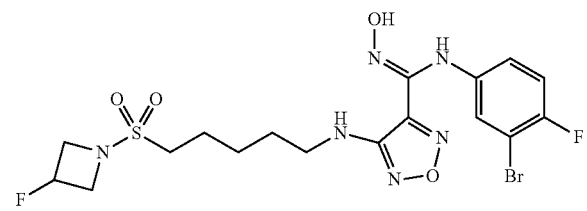
124
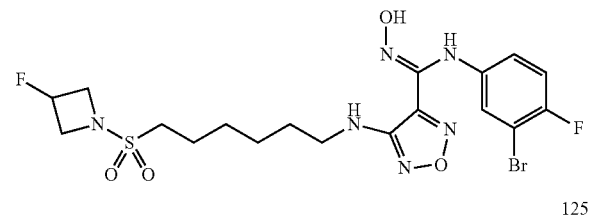
125
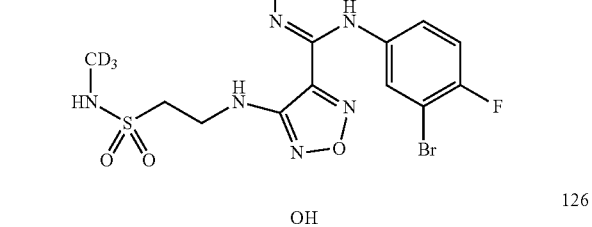
126
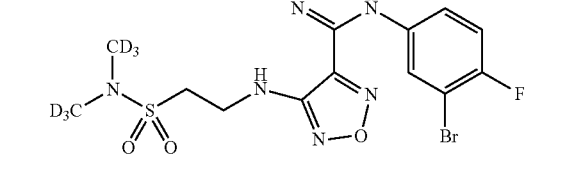

-continued

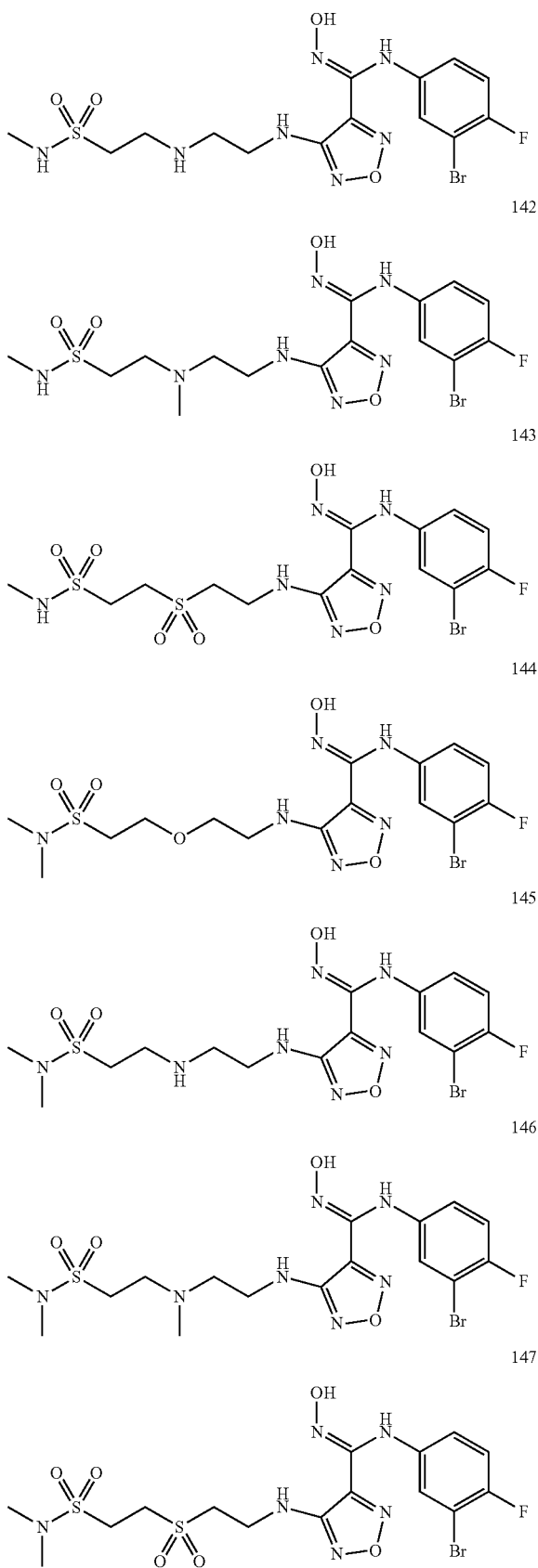

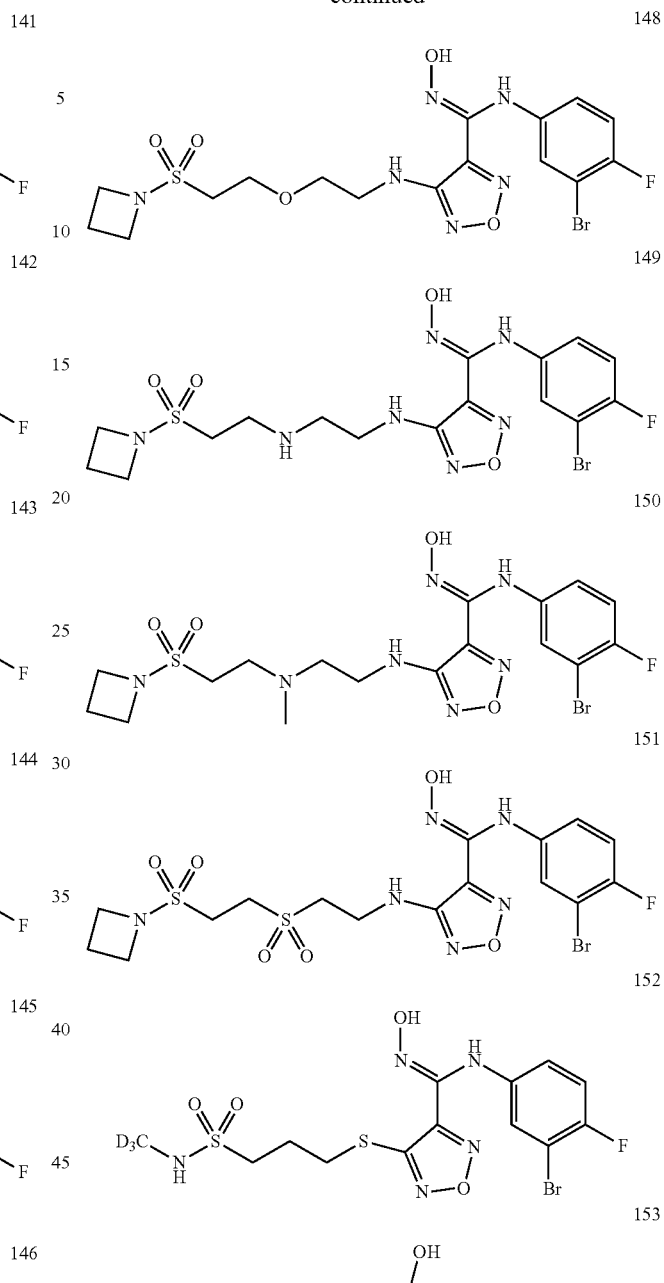

10. A method for treating diseases with pathological characteristics of IDO mediated tryptophan metabolism pathway, comprising administering to a subject in need thereof a suitable amount of a composition comprising the compound, or optical isomer thereof, or cis- and trans-isomer thereof, or isotope compound thereof, or solvate thereof, or pharmaceutically acceptable salt thereof, or pro-drug thereof, or tautomer thereof, or mesomer thereof, or racemate thereof, or enantiomer thereof, or diastereoisomer thereof, or mixture thereof according to claim 1.

11. The method of claim 10, wherein said diseases are selected from cancer, myelodysplastic syndrome, Alzheimer's disease, autoimmune disease, depression, anxiety disorder, cataract, psychological disorder and AIDS; in which said cancer is selected from breast cancer, cervical cancer, colon cancer, lung cancer, gastric cancer, rectal cancer, pancreatic cancer, brain cancer, skin cancer, oral cancer, prostate cancer, bone cancer, kidney cancer, ovarian cancer, bladder cancer, liver cancer, fallopian tube tumor, ovarian tumor, peritoneal tumor, stage IV melanoma, solid tumor, glioma, neuroglioblastoma, hepatocyte cancer, and mastoid nephroma.

12. A drug combination, comprising an active ingredient selected from the compounds, or optical isomers thereof, or cis- and trans-isomers thereof, or isotope compounds thereof, or solvates thereof, or pharmaceutically acceptable salts thereof, or pro-drugs thereof, or tautomers thereof, or mesomers thereof, or racemates thereof, or enantiomers thereof, or diastereoisomers thereof, or mixtures thereof according to claim 1, and one or more pharmaceutically acceptable adjuvants.

13. A drug for the treatment of diseases with pathological characteristics of IDO mediated tryptophan metabolism pathway, prepared using the drug combination of claim 12.

14. A method for treating diseases with pathological characteristics of IDO mediated tryptophan metabolism pathway, comprising administering to a subject in need thereof a suitable amount of a composition comprising a drug according to claim 13, wherein the diseases are selected from cancer, myelodysplastic syndrome, Alzheimer's disease, autoimmune disease, depression, anxiety disorder, cataract, psychological disorder and AIDS; in which said cancer is selected from breast cancer, cervical cancer, colon cancer, lung cancer, gastric cancer, rectal cancer, pancreatic cancer, brain cancer, skin cancer, oral cancer, prostate cancer, bone cancer, kidney cancer, ovarian cancer, bladder cancer, liver cancer, fallopian tube tumor, ovarian tumor, peritoneal tumor, stage IV melanoma, solid tumor, glioma, neuroglioblastoma, hepatocyte cancer, and mastoid nephroma.

* * * * *